(12) United States Patent
Fang et al.

(10) Patent No.: US 8,398,971 B2
(45) Date of Patent: Mar. 19, 2013

(54) METHODS, COMPOUNDS, AND COMPOSITIONS FOR TREATMENT AND PROPHYLAXIS IN THE RESPIRATORY TRACT

(75) Inventors: Fang Fang, Rancho Santa Fe, CA (US); David Wurtman, San Diego, CA (US); Ron Moss, Encinitas, CA (US); Michael P. Malakhov, San Francisco, CA (US)

(73) Assignee: NexBio, Inc., San Diego, CA (US)

( * ) Notice: Subject to any disclaimer, the term of this patent is extended or adjusted under 35 U.S.C. 154(b) by 143 days.

(21) Appl. No.: 12/940,742

(22) Filed: Nov. 5, 2010

(65) Prior Publication Data

US 2011/0171132 A1    Jul. 14, 2011

Related U.S. Application Data

(60) Provisional application No. 61/259,033, filed on Nov. 6, 2009, provisional application No. 61/259,055, filed on Nov. 6, 2009, provisional application No. 61/322,813, filed on Apr. 9, 2010, provisional application No. 61/332,063, filed on May 6, 2010, provisional application No. 61/381,420, filed on Sep. 9, 2010.

(51) Int. Cl.
*A61K 38/46* (2006.01)
(52) U.S. Cl. .................................... 424/94.65
(58) Field of Classification Search ............... 424/94.65
See application file for complete search history.

(56) References Cited

U.S. PATENT DOCUMENTS

| 7,645,448 B2 * | 1/2010 | Fang et al. ............. 424/94.6 |
| 7,807,174 B2 * | 10/2010 | Fang et al. ............. 424/192.1 |
| 2009/0142327 A1 | 6/2009 | Fang et al. |
| 2009/0196930 A1 | 8/2009 | Surber et al. |
| 2009/0220581 A1 | 9/2009 | Li et al. |

OTHER PUBLICATIONS

Blitz et al. 2005; Inhaled magnesium sulfate in the treatment of acute asthma (Review) The Cochrane Database of Systemic Reviews 2005, Issue 4, pp. 1-23.*
WebMD 2005; Histidine. www.swebmd.co/vitamines-supplements/ingredientmono-467-HISTIDINE.*

* cited by examiner

*Primary Examiner* — Karen Cochrane Carlson
(74) *Attorney, Agent, or Firm* — Fish & Richardson P.C.

(57) ABSTRACT

The present invention provides a method of reducing the quanitity of mucus in the respiratory tract of a subject with elevated levels of mucus in said respiratory tract. The method includes administering to the subject a compound or composition containing a therapeutically effective amount of a fusion protein comprising a sialidase or an active portion thereof and an anchoring domain. The therapeutically effective amount comprises an amount of the fusion protein that results in a reduction of the quanitity of mucus in the respiratory tract after administration of the compound or composition when compared to the quantity of mucus present prior to administration of the compound or composition.

57 Claims, 26 Drawing Sheets

PF4 (SEQ ID NO:2): $^{47}$NGRRICLDLQAPLYKKIIKKLLES$^{70}$

IL-8 (SEQ ID NO:3): $^{46}$GRELCLDPKENWVQRVVEKFLKRAENS$^{72}$

ATIII (SEQ ID NO:4): $^{118}$QIHFFFAKLNCRLYRKANKSSKLVSANRLFGDKS$^{151}$

ApoE (SEQ ID NO:5): $^{132}$ELRVRLASHLRKLRKRLLRDADDLQKRLAVYQAG$^{165}$

AAMP (SEQ ID NO:6): $^{17}$RRLRRMESESES$^{25}$

Amphiregulin (SEQ ID NO: 7): $^{125}$KRKKKGGKNGKNRRNRKKKNP$^{145}$

FIG. 1

```
NEU2(SEQ ID NO:8):  1 MASLPVLQKE SVFQSGAHA- -YRIPALLYL PGQQSLLAFA EQRASKKDEH
                                           YR P LL  + P    +LLAF EQR S   D H
NEU4(SEQ ID NO:9):  1 MGVPRTPSRT VLFERERTGL TYRVPSLLPV PPGPTLLAFV EQRLSPDDSH

NEU2:  49 AELIVLRRGD YDAPTHQVQW QAQEVVAQAR LDGHRSMNPC PLYDAQTGTL FLFFIAIPGQ
          A  +V RRG            +W  A  ++  A    HRSMNPC P+ DA TGT+ FLFFIA+ G
NEU4:  51 AHRLVLRRGT LAGGSV--RW GALHVLGTAA LAEHRSMNPC PVHDAGTGTV FLFFIAVLGH

NEU2: 110 VTEQQQLQTR ANVTRLCQVT STDHGRTWSS PRDLTDAAIG PAYREWSTFA VGPGHCLQLN
            E  Q+ T   N  RLC V  S D G +W S  RDLT+ AIG  A  ++W+TFA VGPGH +QL
NEU4: 109 TPEAVQIATG RNAARLCCVA SRDAGLSWGS ARDLTEEAIG GAVQDWATFA VGPGHGVQLP

NEU2: 170 DRARSLVVPA YAYRKLHP-- ---IQRPIPS AFCFLSHDHG RTWARGHPVA QD-TLECQVA
             R L+VPA Y YR            I R P   +F FS DHG RTW  G V     + ECQ+A
NEU4: 169 S-GR-LLVPA YTYRVDRLEC FGKICRTSPH SFAFYSDDHG RTWRCGGLVP NLRSGECQLA

NEU2: 224 EVETGEQRVV TL-NARSHLR ARVQAQSTND GLDFQESQLV KKLVEPPPQG CQGSVISFPS
             V+  G+        NARS L  +RVQA  ST++ G F   ++ V    L E    G CQGS++ FP
NEU4: 227 AVDGGQAGSF LYCNARSPLG SRVQALSTDE GTSFLPAERV ASLPETAW-G CQGSIVGFPA

NEU2: 283 P--------- ---------- ---------- ---------- ---------- ----------

NEU4: 286 PAPNRPRODS WSVGPRSPLQ PPLLGPGVHE PPEEAAVDPR GGQVPGGPFS RLQPRGDGP

NEU2: 284 ---------- ---------- ---RSGPGSP QWLLYTHPTH SWQRADLGAY LNPRPPAPEA
                                         WLLY+HP      R +G  L+  P  P +
NEU4: 346 RQPGPRPGVSG DVGSWTLALP MPFAAPPQSP TWLLYSHPVG RRARLHMGIR LSQSPLDPRS

NEU2: 321 WSEPVLLAKG SCAYSDLQSM GTGPDGSPLF GCLYEANDY- --EEIVFLMF TLKQAFPAEY
          W+EP ++ +      YSDL S+  G  P+G  +F +CLYE              +L++
NEU4: 406 WTEPWVIYEG PSGYSDLASI GPAPEGGLVF ACLYESGART SYDEISFCTF SLREVLENVP

NEU2: 378 LPQ

NEU4: 466 ASPKPPNLGD KPRGCCWPS
```

FIG. 2

Substrate Specificity of Bacteria and Fungal Sialidases

| Substrates | Vibrio Cholerae | Clostridium perfringens (71Kd) | Clostridium perfringens (43Kd) | Arthrobacter ureafaciens | Salmonella typhimurium | Actinomyces viscosus |
|---|---|---|---|---|---|---|
| Oligo- and polysaccharides | | | | | | |
| II$^3$Neu5AcLac | 100 | 100 | 100 | 100 | 100 | 100 |
| II$^6$Neu5AcLac | 53 | 44 | 19 | 157 | 0.4 | 462 |
| Colominic acid (α2-8) | 30 | 33 | 4.0 | 63 | 0.1 | 300 |
| Glycoproteins | | | | | | |
| Fetuin (α2-3>α2-6) | 340 | 272 | 6.6 | 59 | 17 | --- |
| α1-Acid glycoprotein (α2-6>α2-3) | 1000 | 555 | --- | --- | --- | 761 |
| Submandibular gland mucin (α2-6) | 400 | 139 | 5.1 | --- | --- | 123 |
| Submaxillary gland mucin (α2-6) | --- | --- | --- | 56 | --- | --- |
| Gangliosides | | | | | | |
| Gangliosides mixtures | (360) | (350) | 1.6 | 78 | 34 | 285 |
| Synthetic | | | | | | |
| 4MU-Neu5Ac | 1580 | 605 | 58 | --- | 1050 | --- |

*Each value represents a relative sialidase activity when the activity directed toward II$^3$Neu5AcLac is regard as 100

FIG. 3

SEQ ID NOs: 28 & 29

```
ccatggggcatcaccatcaccatcatctagagggagatcatccacaagctacaccagcacct
  M  G  H  H  H  H  H  L  E  G  D  H  P  Q  A  T  P  A  P
gcaccagatgctagcactgagctgccagcaagcatgtctcaggctcagcatcttgcagca
  A  P  D  A  S  T  E  L  P  A  S  M  S  Q  A  Q  H  L  A  A
aatacggctactgataattatcgcattccagcgattacaaccgctccgaatggtgattta
  N  T  A  T  D  N  Y  R  I  P  A  I  T  T  A  P  N  G  D  L
ctgattagctatgatgaacggccgaaggacaatggaaatggtggttccgatgcccctaac
  L  I  S  Y  D  E  R  P  K  D  N  G  N  G  G  S  D  A  P  N
ccgaatcatattgttcagcgtcgctccacagatggcggtaaaacttggagcgcgccaacc
  P  N  H  I  V  Q  R  R  S  T  D  G  G  K  T  W  S  A  P  T
tatattcatcagggtacggagactggcaagaaagtgggatattccgacccctcttatgtg
  Y  I  H  Q  G  T  E  T  G  K  K  V  G  Y  S  D  P  S  Y  V
gtggatcatcaaaccggtacaatcttcaattttcatgtgaaatcatacgatcagggctgg
  V  D  H  Q  T  G  T  I  F  N  F  H  V  K  S  Y  D  Q  G  W
ggaggtagccgtgggggaacagacccggaaaaccgcgggattattcaggcagaggtgtct
  G  G  S  R  G  G  T  D  P  E  N  R  G  I  I  Q  A  E  V  S
acgagcacggataatggatggacgtggacacatcgcaccatcaccgcggatattacgaaa
  T  S  T  D  N  G  W  T  W  T  H  R  T  I  T  A  D  I  T  K
gataaaccgtggaccgcgcgttttgcggcgtccggccaaggcattcagatccagcatggg
  D  K  P  W  T  A  R  F  A  A  S  G  Q  G  I  Q  I  Q  H  G
ccgcatgccggccgtctggtgcaacagtataccattcgtacggccggtggagcggtgcag
  P  H  A  G  R  L  V  Q  Q  Y  T  I  R  T  A  G  G  A  V  Q
gctgtatcggtttattccgatgatcatgggaaaacgtggcaggctggcaccccgattggg
  A  V  S  V  Y  S  D  D  H  G  K  T  W  Q  A  G  T  P  I  G
acgggtatggatgaaaacaaagttgtagagctgtctgacggctctctgatgctgaacagt
  T  G  M  D  E  N  K  V  V  E  L  S  D  G  S  L  M  L  N  S
cgtgcgtcggacgggagcggctttcgtaaggttgcgcatagcactgatggtgggcagacc
  R  A  S  D  G  S  G  F  R  K  V  A  H  S  T  D  G  G  Q  T
tggtccgaaccggtttcggacaaaaatttgccggattcggttgataatgcccagataatt
  W  S  E  P  V  S  D  K  N  L  P  D  S  V  D  N  A  Q  I  I
cgtgcgtttcctaatgctgcccccgatgacccgcgcgcgaaagtacttcttctgagtcat
  R  A  F  P  N  A  A  P  D  D  P  R  A  K  V  L  L  S  H
tccccaaatccacgtccgtggtcccgggatcgtggtacgataagcatgtcatgtgatgac
  S  P  N  P  R  P  W  S  R  D  R  G  T  I  S  M  S  C  D  D
ggggcctcatggaccacttccaaagttttttcacgaaccgtttgtgggctacacgactatt
  G  A  S  W  T  T  S  K  V  F  H  E  P  F  V  G  Y  T  T  I
gcagttcagagtgatggaagcatcggtctgctgtcggaggacgcgcacaatggcgctgat
  A  V  Q  S  D  G  S  I  G  L  L  S  E  D  A  H  N  G  A  D
tatggtggcatctggtatcgtaattttacgatgaactggctgggagaacaatgtggacaa
  Y  G  G  I  W  Y  R  N  F  T  M  N  W  L  G  E  Q  C  G  Q
aaacccgcggaataagctt
  K  P  A  E
```

FIG. 4

SEQ ID NOs: 18 & 19

```
ccatggttaagcgcaaaaaaaaggcggcaaaaacggtaaaaatcgtcgtaaccgtaaga
   M  V  K  R  K  K  G  G  K  N  G  K  N  R  R  N  R  K
aaaaatcctggagatcatccacaagctacaccagcacctgcaccagatgctagcactgag
   K  N  P  G  D  H  P  Q  A  T  P  A  P  A  P  D  A  S  T  E
ctgccagcaagcatgtctcaggctcagcatcttgcagcaaatacggctactgataattat
   L  P  A  S  M  S  Q  A  Q  H  L  A  A  N  T  A  T  D  N  Y
cgcattccagcgattacaaccgctccgaatggtgatttactgattagctatgatgaacgg
   R  I  P  A  I  T  T  A  P  N  G  D  L  L  I  S  Y  D  E  R
ccgaaggacaatggaaatggtggttccgatgcccctaacccgaatcatattgttcagcgt
   P  K  D  N  G  N  G  G  S  D  A  P  N  P  N  H  I  V  Q  R
cgctccacagatggcggtaaaacttggagcgcgccaacctatattcatcagggtacggag
   R  S  T  D  G  G  K  T  W  S  A  P  T  Y  I  H  Q  G  T  E
actggcaagaaagtgggatattccgacccctcttatgtggtggatcatcaaaccggtaca
   T  G  K  K  V  G  Y  S  D  P  S  Y  V  V  D  H  Q  T  G  T
atcttcaattttcatgtgaaatcatacgatcagggctggggaggtagccgtgggggaaca
   I  F  N  F  H  V  K  S  Y  D  Q  G  W  G  G  S  R  G  G  T
gacccggaaaaccgcgggattattcaggcagaggtgtctacgagcacggataatggatgg
   D  P  E  N  R  G  I  I  Q  A  E  V  S  T  S  T  D  N  G  W
acgtggacacatcgcaccatcaccgcggatattacgaaagataaaccgtggaccgcgcgt
   T  W  T  H  R  T  I  T  A  D  I  T  K  D  K  P  W  T  A  R
tttgcggcgtccggccaaggcattcagatccagcatgggccgcatgccggccgtctggtg
   F  A  A  S  G  Q  G  I  Q  I  Q  H  G  P  H  A  G  R  L  V
caacagtataccattcgtacggccggtggagcggtgcaggctgtatcggtttattccgat
   Q  Q  Y  T  I  R  T  A  G  G  A  V  Q  A  V  S  V  Y  S  D
gatcatgggaaaacgtggcaggctggcaccccgattgggacgggtatggatgaaaacaaa
   D  H  G  K  T  W  Q  A  G  T  P  I  G  T  G  M  D  E  N  K
gttgtagagctgtctgacggctctctgatgctgaacagtcgtgcgtcggacgggagcggc
   V  V  E  L  S  D  G  S  L  M  L  N  S  R  A  S  D  G  S  G
tttcgtaaggttgcgcatagcactgatggtgggcagacctggtccgaaccggtttcggac
   F  R  K  V  A  H  S  T  D  G  G  Q  T  W  S  E  P  V  S  D
aaaaatttgccggattcggttgataatgcccagataattcgtgcgtttcctaatgctgcc
   K  N  L  P  D  S  V  D  N  A  Q  I  I  R  A  F  P  N  A  A
cccgatgacccgcgcgcgaaagtacttcttctgagtcattccccaaatccacgtccgtgg
   P  D  D  P  R  A  K  V  L  L  L  S  H  S  P  N  P  R  P  W
tcccgggatcgtggtacgataagcatgtcatgtgatgacggggcctcatggaccacttcc
   S  R  D  R  G  T  I  S  M  S  C  D  D  G  A  S  W  T  T  S
aaagttttccacgaaccgtttgtgggctacacgactattgcagttcagagtgatggaagc
   K  V  F  H  E  P  F  V  G  Y  T  T  I  A  V  Q  S  D  G  S
atcggtctgctgtcggaggacgcgcacaatggcgctgattatggtggcatctggtatcgt
   I  G  L  L  S  E  D  A  H  N  G  A  D  Y  G  G  I  W  Y  R
aattttacgatgaactggctgggagaacaatgtggacaaaaacccgcggaataagctt
   N  F  T  M  N  W  L  G  E  Q  C  G  Q  K  P  A  E  -  A
```

FIG. 5

SEQ ID NO:36 & 37

```
ccatggttaagcgcaaaaaaaaggcggcaaaaacggtaaaaatcgtcgtaaccgtaagaaa
   M  V  K  R  K  K  K  G  G  K  N  G  K  N  R  R  N  R  K  K
aaaaatcctggtggtggtggttctggagatcatccacaagctacaccagcacctgcacca
 K  N  P  G  G  G  S  G  D  H  P  Q  A  T  P  A  P  A  P
gatgctagcactgagctgccagcaagcatgtctcaggctcagcatcttgcagcaaatacg
 D  A  S  T  E  L  P  A  S  M  S  Q  A  Q  H  L  A  A  N  T
gctactgataattatcgcattccagcgattacaaccgctccgaatggtgatttactgatt
 A  T  D  N  Y  R  I  P  A  I  T  T  A  P  N  G  D  L  L  I
agctatgatgaacggccgaaggacaatggaaatggtggttccgatgcccctaacccgaat
 S  Y  D  E  R  P  K  D  N  G  N  G  G  S  D  A  P  N  P  N
catattgttcagcgtcgctccacagatggcggtaaaacttggagcgcgccaacctatatt
 H  I  V  Q  R  R  S  T  D  G  G  K  T  W  S  A  P  T  Y  I
catcagggtacggagactggcaagaaagtgggatattccgacccctcttatgtggtggat
 H  Q  G  T  E  T  G  K  K  V  G  Y  S  D  P  S  Y  V  V  D
catcaaaccggtacaatcttcaattttcatgtgaaatcatacgatcagggctggggaggt
 H  Q  T  G  T  I  F  N  F  H  V  K  S  Y  D  Q  G  W  G  G
agccgtgggggaacagacccggaaaaccgcgggattattcaggcagaggtgtctacgagc
 S  R  G  G  T  D  P  E  N  R  G  I  I  Q  A  E  V  S  T  S
acggataatggatggacgtggacacatcgcaccatcaccgcggatattacgaaagataaa
 T  D  N  G  W  T  W  T  H  R  T  I  T  A  D  I  T  K  D  K
ccgtggaccgcgcgttttgcggcgtccggccaaggcattcagatccagcatgggccgcat
 P  W  T  A  R  F  A  A  S  G  Q  G  I  Q  I  Q  H  G  P  H
gccggccgtctggtgcaacagtataccattcgtacggccggtggagcggtgcaggctgta
 A  G  R  L  V  Q  Q  Y  T  I  R  T  A  G  G  A  V  Q  A  V
tcggtttattccgatgatcatgggaaaacgtggcaggctggcacccgattgggacgggt
 S  V  Y  S  D  D  H  G  K  T  W  Q  A  G  T  P  I  G  T  G
atggatgaaaacaaagttgtagagctgtctgacggctctctgatgctgaacagtcgtgcg
 M  D  E  N  K  V  V  E  L  S  D  G  S  L  M  L  N  S  R  A
tcggacgggagcggctttcgtaaggttgcgcatagcactgatggtgggcagacctggtcc
 S  D  G  S  G  F  R  K  V  A  H  S  T  D  G  G  Q  T  W  S
gaaccggtttcggacaaaaatttgccggattcggttgataatgcccagataattcgtgcg
 E  P  V  S  D  K  N  L  P  D  S  V  D  N  A  Q  I  I  R  A
tttcctaatgctgcccccgatgacccgcgcgcgaaagtacttcttctgagtcattcccca
 F  P  N  A  A  P  D  D  P  R  A  K  V  L  L  L  S  H  S  P
aatccacgtccgtggtcccgggatcgtggtacgataagcatgtcatgtgatgacggggcc
 N  P  R  P  W  S  R  D  R  G  T  I  S  M  S  C  D  D  G  A
tcatggaccacttccaaagttttcacgaaccgtttgtgggctacacgactattgcagtt
 S  W  T  T  S  K  V  F  H  E  P  F  V  G  Y  T  T  I  A  V
cagagtgatggaagcatcggtctgctgtcggaggacgcgcacaatggcgctgattatggt
 Q  S  D  G  S  I  G  L  L  S  E  D  A  H  N  G  A  D  Y  G
ggcatctggtatcgtaatttacgatgaactggctgggagaacaatgtggacaaaaaccc
 G  I  W  Y  R  N  F  T  M  N  W  L  G  E  Q  C  G  Q  K  P
gcggaataagctt
 A  E  -  A
```

FIG. 6

PENH: Enhanced Pause = ((Te/RT)-1).(PEF/PIF)
*BEFORE CHALLENGE*
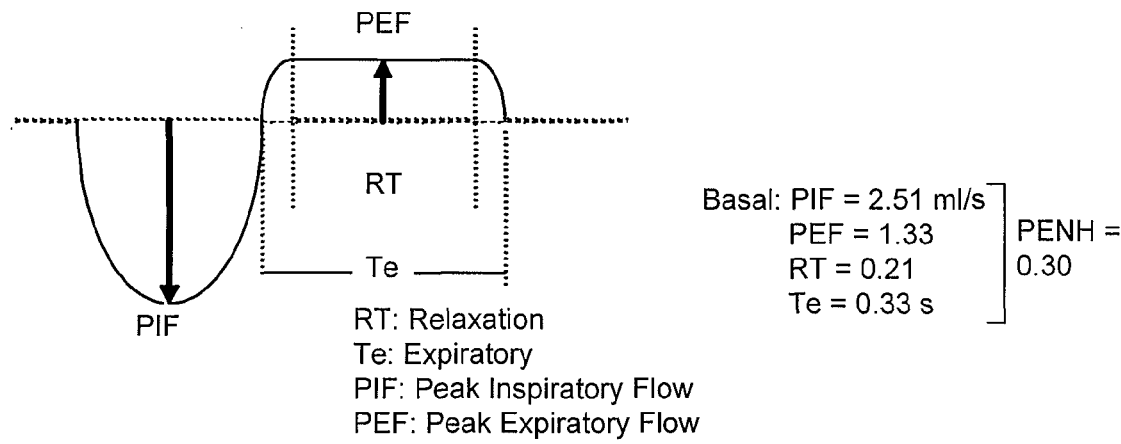
Basal: PIF = 2.51 ml/s
PEF = 1.33
RT = 0.21
Te = 0.33 s
PENH = 0.30
RT: Relaxation
Te: Expiratory
PIF: Peak Inspiratory Flow
PEF: Peak Expiratory Flow
*AFTER CHALLENGE*
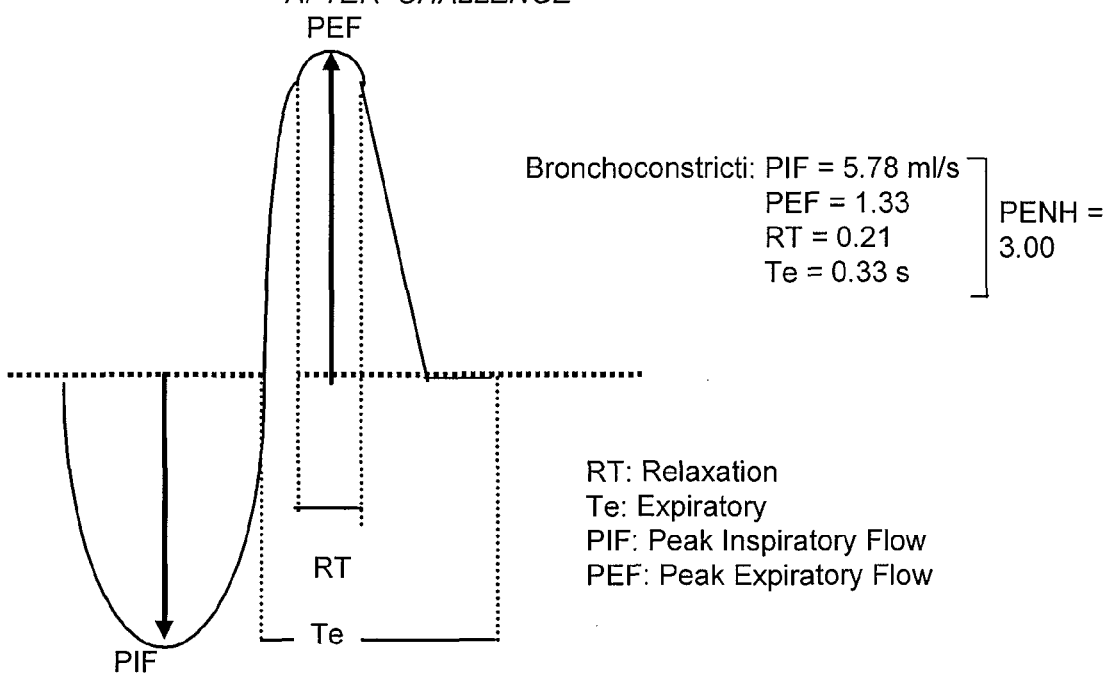
Bronchoconstricti: PIF = 5.78 ml/s
PEF = 1.33
RT = 0.21
Te = 0.33 s
PENH = 3.00
RT: Relaxation
Te: Expiratory
PIF: Peak Inspiratory Flow
PEF: Peak Expiratory Flow
FIG. 8

Lung Section PAS Staining

FIGS. 19A-F

METHODS, COMPOUNDS, AND COMPOSITIONS FOR TREATMENT AND PROPHYLAXIS IN THE RESPIRATORY TRACT

CLAIM OF PRIORITY

This application claims the benefit of U.S. Provisional Patent Application Ser. No. 61/259,033, filed on Nov. 6, 2009, and U.S. Provisional Patent Application Ser. No. 61/259,055, filed on Nov. 6, 2009, U.S. Provisional Patent Application Ser. No. 61/322,813, filed on Apr. 9, 2010, U.S. Provisional Patent Application Ser. No. 61/322,063, filed on May 6, 2010, and U.S. Provisional Patent Application Ser. No. 61/381,420 filed on Sep. 9, 2010, the entire contents of each of which are hereby incorporated by reference.

FEDERALLY SPONSORED RESEARCH OR DEVELOPMENT

This invention was made with Government support under contract number HHSN266200600015C awarded by the United States Department of Health and Human Services, National Institutes of Health. The Government has certain rights in the invention.

BACKGROUND

Respiratory tract infections (RTIs) are among the most common, and potentially most severe, types of infectious diseases. Examples of RTIs include influenza, parainfluenza, RSV, sinusitis, otitis, laryngitis, bronchitis and pneumonia.

One common feature of agents that cause RTIs, such as respiratory pathogenic bacteria, is that they establish commensal colonization on the mucosal surface of the upper airway; such colonization precedes an infection and generally is prerequisite for infections. Bacterial colonization in a neonate occurs shortly after birth. During one's lifetime, the upper airway, specifically the nasopharynx and oropharynx, remains a dynamic ecological reservoir of microbial species with bacteria being acquired, eliminated and re-acquired continually. In most cases, the bacterial flora in the pharynx are harmless. However, when the condition of the host is altered, some microorganisms may invade adjacent tissues or bloodstream to cause diseases.

In addition to serving as the port of entry for mucosal and invasive infections by both bacteria and viruses, the nasopharynx and oropharynx are also the major source of spreading the pathogenic microorganisms between individuals, as well as the reservoir where antibiotic-resistant bacteria are selected (Garcia-Rodriguez and Martinez, *J Antimicrob Chemother*, (2002) 50(Suppl S2), 59-73; Soriano and Rodriguez-Cerrato, *J Antimicrob Chemother*, (2002) 50 Suppl S2, 51-58). It is well established clinically that individuals who are prone to RTIs tend to be persistent and recurrent carriers of pathogenic bacteria (Garcia-Rodriguez and Martinez, *J Antimicrob Chemother*, (2002) 50(Suppl S2), 59-73; Mbaki et al., *Tohoku J. Exp. Med.*, (1987) 153(2), 111-121). For example, *Helicobacter pylori* is a human pathogen implicated in gastritis and peptic ulcer. The bacterium resides in the human stomach and binds to epithelial cells of the gastric antrum.

Other disorders of the respiratory tract (more broadly termed, RTDs) may not be caused by infectious agents, although they could arise as a consequence of infection. Examples of RTDs include a variety of obstructive lung diseases such as allergic and non-allergic asthma, COPD, bronchiectasis, vasculitis, mucous plugging, Wegener's granulomatosis and cystic fibrosis (CF). RTDs can have a genetic basis (for example, CF), can arise due to immunodeficiencies, can arise due to other deficiencies (for example, alpha-1-antitrypsin deficiency can make people more susceptible to bronchiectasis), can be caused by allergens and/or chemical pollutants, or can present as complications of other infectious diseases such as the RTIs described above or inflammatory diseases such as inflammatory bowel syndrome or Crohn's disease.

Common indications of RTIs and RTDs include inflammation and elevated levels of mucous in the respiratory tract. However, currently available drugs that are used to treat RTIs and RTDs often are unable to ameliorate these associated conditions. For example, Relenza® is a well-known treatment for influenza, but it is not recommended for patients who suffer from underlying airway disease, such as asthma and COPD. Thus, in addition to the need for drugs that reduce inflammation and/or reduce mucus in the respiratory tract or limit its increase are drugs that are capable of treating respiratory infectious diseases, such as influenza, parainfluenza and RSV, without aggravating underlying respiratory conditions, such as asthma, bronchitis, bronchiectasis, and COPD, of patients.

The present invention recognizes that drugs currently available for medical use have limited efficacy with respect to reducing inflammation, and/or reducing mucus in the respiratory tract or limiting its increase in the respiratory tract, and those that are available are associated with side effects. The present invention also recognizes that there is a need for drugs for treating respiratory infectious diseases in patients with underlying airway disease, such as asthma, bronchitis, bronchiectasis and COPD. Thus, there is a need for new drugs that are able to reduce inflammation, and/or drugs that reduce mucus in the respiratory tract or limit its increase in the respiratory tract. There is also a need for drugs that can treat respiratory infectious diseases while reducing inflammation, and/or while reducing mucus in the respiratory tract or limiting its increase in the respiratory tract.

SUMMARY

The compositions, components of compostions and methods provided below are characterized by a variety of component ingredients, steps of preparation, and biophysical, physical, biochemical or chemical parameters. As would be apparent to those of skill in the art, the compositions and methods provided herein include any and all permutations and combinations of the ingredients, steps and/or parameters described below.

The invention relates to the use of therapeutic compounds and compositions that have anti-inflammatory effects in the respiratory tract and to methods of treating respiratory inflammation and prophylaxis against respiratory inflammation. The invention also relates to therapeutic compounds and compositions that can be used to prevent or treat diseases that are caused by, cause, or are exacerbated by respiratory inflammation, including, but not limited to, inflammation not caused by allergies or allergic reactions.

The invention also relates to the use of therapeutic compounds and compositions to reduce the quantity of mucus in the respiratory tract of subjects with elevated levels of mucus in their respiratory tracts, and to corresponding methods of treatment. The invention also relates to the use of therapeutic compounds and compositions to limit an increase in the quantity of mucus in the respiratory tract of subjects above a baseline level of mucus in their respiratory tract and to corresponding methods of treatment. The invention also relates to therapeutic compounds and compositions that can be used to prevent or treat conditions and/or diseases that are caused by, cause, or are exacerbated by increased mucus in the respiratory tract, such as, both allergic and non-allergic asthma, chronic obstructive pulmonary disease (COPD), bronchitis (both acute and non-acute), bronchiectasis, cystic fibrosis (CF), vasculitis, mucus plugging, Wegener's granulomatosis, pneumonia, tuberculosis, cancers involving the lungs or the respiratory tract, Kartagener syndrome, Young's syndrome, chronic sinopulmonary infections, alpha 1-antitrypsin deficiency, primary immunodeficiencies, acquired immune deficiency syndrome, opportunistic infections, infectious and post infectious states, common cold, exercise-induced asthma, exercise induced hypersecretion of mucus, inflammatory bowel disease, ulcerative colitis, Crohn's disease, allergic reactions to inhaled fungus spores, respiratory infections, respiratory obstructions, inhalation or aspiration of ammonia and other toxic gases, pulmonary aspiration, alcoholism, various allergies, and any other disorder that causes increased mucus production in the respiratory tract or is caused by or exacerbated by increased mucus production in the respiratory tract. In some embodiments, the subject has more than one of the aforementioned conditions and/or diseases. In other embodiments, the subject having one or more of the aforementioned conditions and/or diseases does not have an accompanying infectious disease (RTI), such as influenza, parainfluenza or RSV. In other embodiments, the subject having one or more of the aforementioned conditions and/or diseases has one or more accompanying infectious diseases, such as influenza, parainfluenza or RSV. Thus, provided herein are methods, compounds and compositions for treating inflammatory and/or allergic responses associated with an RTI, an RTD, or combinations thereof.

The compounds and compositions provided herein can reduce mucus production in the respiratory tract and/or reduce the levels of inflammatory cells that cause allergic or non-allergic types of inflammation, including, without limitation, monocytes, macrophages, dendritic cells, histiocytes, Kuppfer cells, mastocytes and neutrophiles.

The compounds and compositions provided herein include a sialidase or active portion thereof. Without being bound by any theory, sialic acids have been implicated in allergic and/or inflammatory responses associated with RTIs and RTDs. For example, siglecs (sialic acid binding Ig-like lectins) are members of the immunoglobulin (Ig) superfamily that bind to sialic acid and are mainly expressed by cells of the hematopoietic system. At least 11 siglecs have been discovered and they seem to exclusively recognize cell surface sialic acid as the ligand. It is believed that the binding of siglecs to sialic acid mediates cell-cell adhesion and interactions (Crocker and Valid, Trends Immunol., (2001) 22(6), 337-342; Angata and Brinkman-Van der Linden, Biochim. Biophys. Acta, (2002) 1572(2-3), 294-316). Siglec-8 (SAF-2) is an adhesion molecule that is highly restricted to the surface of eosinophils, basophils, and mast cells, which are the central effector cells in allergic conditions including allergic rhinitis, asthma and eczema. Siglec-8 (homologous to Siglec-F in mice) is considered to be responsible for mediating the recruitment of the three allergic cell types to the airway, the lungs and other sites of allergy. Siglec-1 (sialoadhesion) and siglec-2 (CD22) are the adhesion molecules on macrophages and B cells, both types of cells play central roles in immune reactions that lead to inflammation. Siglec-9 is predominantly expressed on neutrophils, which are known to be important effector cells in inflammation (von Gunten, Yousefi, Seitz, Jakob, Schaffner, Seger, Takala, Villiger, and Simon (2005) *Blood* 106:1423-1431). Further, without being bound by any particular theory, sialic acid residues have been implicated in the interaction of muscaranic receptors with agonists; thus, sialidases can affect the interecation of muscarinic receptors with their agonists.

The present invention provides a method of reducing the quanitity of mucus in the respiratory tract of a subject with elevated levels of mucus in said respiratory tract. The method includes administering to the subject a compound or composition containing a therapeutically effective amount of a fusion protein having a sialidase or an active portion thereof and an anchoring domain. The therapeutically effective amount includes an amount of the fusion protein that results in a reduction of the quantity of mucus in the respiratory tract after administration of the compound or composition when compared to the quantity of mucus present prior to administration of the composition.

In another embodiment, another method of reducing the quantity of mucus in the respiratory tract of a subject with elevated levels of mucus in said respiratory tract is provided. The method includes administering to the subject a compound or composition containing a therapeutically effective amount of a fusion protein. The fusion protein has at least one catalytic domain of a sialidase, wherein the catalytic domain of the sialidase includes the sequence of amino acids extending from amino acid 274 to amino acid 666 of SEQ ID NO:12, inclusive, and at least one anchoring domain. The anchoring domain can be a glycosaminoglycan (GAG) binding domain of human amphiregulin including the amino acid sequence of SEQ ID NO:7. The therapeutically effective amount includes an amount of the fusion protein that results in a reduction of the quanitity of mucus in the respiratory tract after administration of the compound or composition when compared to the quantity of mucus present prior to administration of the composition.

In another embodiment, another method of reducing the quantity of mucus in the respiratory tract of a subject with elevated levels of mucus in said respiratory tract is provided. The method includes administering to the subject a compound or composition containing a therapeutically effective amount of a protein or peptide having a sialidase or an active portion thereof. The therapeutically effective amount includes an amount of the protein or peptide that results in a reduction of the quantity of mucus in the respiratory tract after administration of the compound or composition when compared to the quantity of mucus present prior to administration of the compound or composition.

In another embodiment, a method of treating or ameliorating the effects of chronic obstructive pulmonary disease (COPD), bronchitis, bronchiectasis, cystic fibrosis (CF), vasculitis, mucus plugging, Wegener's granulomatosis, pneumonia, tuberculosis, cancer involving the lungs or the respiratory tract, Kartagener syndrome, Young's syndrome, chronic sinopulmonary infection, alpha 1-antitrypsin deficiency, primary immunodeficiency, acquired immune deficiency syndrome, opportunistic infection, an infectious state, a post infectious state, common cold, exercise induced hypersecretion of mucus, inflammatory bowel disease, ulcerative colitis, Crohn's disease, respiratory infection, respiratory obstruction, inhalation or aspiration of a toxic gas, pulmonary aspiration, or alcoholism in a subject with an elevated level of mucus in his or her respiratory tract is provided. The method includes administering to the subject a compound or composition containing a therapeutically effective amount of a fusion protein. The fusion protein has at least one catalytic domain of a sialidase, wherein the catalytic domain of the sialidase includes the sequence of amino acids extending from amino acid 274 to amino acid 666 of SEQ ID NO:12, inclusive, and at least one anchoring domain. The anchoring domain can be a glycosaminoglycan (GAG) binding domain of human amphiregulin including the amino acid sequence of SEQ ID NO:7. The therapeutically effective amount includes an amount of the fusion protein that results in a reduction of the quantity of mucus in the respiratory tract after administration of the compound or composition when compared to the quantity of mucus present prior to administration of the compound or composition.

In another embodiment, another method of treating or ameliorating the effects of chronic obstructive pulmonary disease (COPD), bronchitis, bronchiectasis, cystic fibrosis (CF), vasculitis, mucus plugging, Wegener's granulomatosis, pneumonia, tuberculosis, cancer involving the lungs or the respiratory tract, Kartagener syndrome, Young's syndrome, chronic sinopulmonary infection, alpha 1-antitrypsin deficiency, primary immunodeficiency, acquired immune deficiency syndrome, opportunistic infection, an infectious state, a post infectious state, common cold, exercise induced hypersecretion of mucus, inflammatory bowel disease, ulcerative colitis, Crohn's disease, respiratory infection, respiratory obstruction, inhalation or aspiration of a toxic gas, pulmonary aspiration, or alcoholism in a subject with an elevated level of mucus in his or her respiratory tract is provided. The method includes administering to the subject a compound or composition containing a therapeutically effective amount of a fusion protein. The fusion protein has a sialidase or an active portion thereof and an anchoring domain. The therapeutically effective amount includes an amount of the fusion protein that results in a reduction of the quantity of mucus in the respiratory tract after administration of the compound or composition when compared to the quantity of mucus present prior to administration of the compound or composition.

In another embodiment, another method of treating or ameliorating the effects of chronic obstructive pulmonary disease (COPD), bronchitis, bronchiectasis, cystic fibrosis (CF), vasculitis, mucus plugging, Wegener's granulomatosis, pneumonia, tuberculosis, cancer involving the lungs or the respiratory tract, Kartagener syndrome, Young's syndrome, chronic sinopulmonary infection, alpha 1-antitrypsin deficiency, primary immunodeficiency, acquired immune deficiency syndrome, opportunistic infection, an infectious state, a post infectious state, common cold, exercise induced hypersecretion of mucus, inflammatory bowel disease, ulcerative colitis, Crohn's disease, respiratory infection, respiratory obstruction, inhalation or aspiration of a toxic gas, pulmonary aspiration, or alcoholism in a subject with an elevated level of mucus in his or her respiratory tract is provided. The method includes administering to the subject a compound or composition containing a therapeutically effective amount of a protein or peptide having a sialidase or an active portion thereof. The therapeutically effective amount includes an amount of the protein or peptide that results in a reduction of the quantity of mucus in the respiratory tract after administration of the compound or composition when compared to the quantity of mucus present prior to administration of the compound or composition.

In another embodiment, a method of limiting an increase in the quantity of mucus in the respiratory tract of a subject above a baseline level of mucus in said subject's respiratory tract is provided. The method includes administering to the subject a compound or composition containing a therapeutically effective amount of a fusion protein. The fusion protein has at least one catalytic domain of a sialidase, wherein the catalytic domain of the sialidase includes the sequence of amino acids extending from amino acid 274 to amino acid 666 of SEQ ID NO:12, inclusive, and at least one anchoring domain, wherein the anchoring domain is a glycosaminoglycan (GAG) binding domain of human amphiregulin comprising the amino acid sequence of SEQ ID NO:7. The therapeutically effective amount includes an amount of the fusion protein that limits an increase in the quantity of mucus in the respiratory tract of said subject above a baseline level after administration of the compound or composition.

In another embodiment, another method of limiting an increase in the quantity of mucus in the respiratory tract of a subject above a baseline level of mucus in said subject's respiratory tract is provided. The method includes administering to the subject a compound or composition containing a therapeutically effective amount of a fusion protein having a sialidase or an active portion thereof and an anchoring domain. The therapeutically effective amount includes an amount of the fusion protein that limits an increase in the quantity of mucus in the respiratory tract of said subject above a baseline level after administration of the compound or composition.

In yet another embodiment, another method of limiting an increase in the quantity of mucus in the respiratory tract of a subject above a baseline level of mucus in said subject's respiratory tract is provided. The method includes administering to the subject a compound or composition containing a therapeutically effective amount of a protein or peptide having a sialidase or an active portion thereof. The therapeutically effective amount includes an amount of the protein or peptide that limits an increase in the quantity of mucus in the respiratory tract of the subject above a baseline level after administration of the compound or composition.

Also contemplated herein are methods of identifying sialidases or active portions thereof according to the compounds or compositions provided herein, where the sialidases or active portions thereof are effective at reducing the quantity of mucus in the respiratory tract of subjects. The reduction in mucus can be measured directly in standard assays known to those of skill in the art. For example, in some embodiments, a single compound or a library or collection of compounds or compositions comprising sialidase(s) and/or catalytically active portion(s) thereof are administered to an animal model of asthma having an associated inflammatory response, such as the guinea pig and the mouse as described in Example 1 and Example 2, respectively. An asthmatic or other inflammatory condition is created in the animal whereby the accumulation of mucus in the lung or respiratory tract is increased. The level of mucus is then quantitated and compared to the level after treatment with a sialidase or active portion thereof. If there is a reduction of the mucus level in the presence of the sialidase or active portion thereof, the sialidase or active portion thereof is identified or selected as one that can be used in the methods provided herein for treating inflammation, allergies and/or associated inflammatory/allergic responses, such as the overproduction of mucus.

In some embodiments, a sialidase or active portion thereof according to the compounds and compositions provided herein is identified as being suitable for treating inflammation, allergies or associated responses by measuring its ability to disrupt muscarinic receptor-agonist interactions according to standard methods known to those of skill in the art. For example, provided herein is a method of assessing whether a compound or composition comprising a sialidase and/or catalytically active portion thereof reduces the quantity of mucus in the respiratory tract of a subject, by (a) contacting the muscarinic receptors of an animal subject with a compound or composition that includes a sialidase and/or a catalytically active portion thereof;

(b) administering a muscarinic receptor agonist to the subject;

(c) quantitating the airway resistance in the subject;

(d) comparing the airway resistance level measured in (c) with the airway resistance in the absence of contact with the compound or composition;

(e) identifying whether the compound or composition reduces the airway resistance relative to the airway resistance in the absence of contact with the compound or composition; and (f) if the compound or composition reduces the airway resistance as determined in (e), assessing the compound or composition as one that reduces the quantity of mucus in the respiratory tract of the subject. Such a method is exemplified in Example 3.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

BRIEF DESCRIPTION OF THE DRAWINGS

FIG. 1 shows GAG-binding sequences of four human genes: PF4, human platelet factor 4; IL8, human interleukin 8; AT III, human antithrombin III; ApoE, human apolipoprotein E; AAMP, human angio-associated migratory cell protein; human amphiregulin.

FIG. 2 is a sequence comparison between human sialidases NEU2 and NEU4 (SEQ ID NOs: 8 & 9).

FIG. 3 is a table comparing substrate specificity of bacterial and fungal sialidases.

FIG. 4 depicts the nucleotide and amino acid sequence (SEQ ID NOs: 28 & 29) of a construct of the present invention encoding His6-AvCD. NcoI and HindIII sites used for cloning into pTrc99a are shown in bold.

FIG. 5 depicts the nucleotide and amino acid sequences (SEQ ID NOs: 18 & 19) of another construct of the present invention encoding AR-AvCD. NcoI and HindIII sites used for cloning into pTrc99a are shown in bold.

FIG. 6 depicts the nucleotide and amino acid sequences (SEQ ID NO: 36 & 37) of another construct of the present invention encoding AR-G$_4$S-AvCD. NcoI and HindIII sites used for cloning into pTrc99a are shown in bold.

FIG. 7A shows the total number of inflammatory cells from nasal wash samples obtained from infected animals at the indicated times after infection. The protein concentration was determined in cell-free nasal wash samples of infected ferrets. Infected ferrets were vehicle-treated (squares) or were treated with recombinant AR-AvCD sialidase fusion protein made from Construct #2 (triangles). Uninfected animals were also treated with recombinant AR-AvCD sialidase fusion protein (diamonds). Statistically significant values are labeled with *($p<0.05$) and **($p<0.01$).

FIG. 8 provides graphs showing formula and explanation of the Enhanced Pause (PENH), the parameter used for measuring bronchoconstriction in conscious unrestrained animals.

FIG. 9 provides a graph showing early asthmatic reaction in response to an OVA-aerosol. Results are expressed as arithmetic average±SEM. *$p<0.05$, ***$p<0.001$ using student's t-test.

FIG. 10 provides a graph showing the total number of cells in guinea pigs on the day of section. Results are expressed as arithmetic average±SEM. $p<0.01$, *$p<0.001$ using student's t-test.

FIG. 11 provides a graph showing the total number of macrophages recovered in guinea pig BAL fluid on the day of section. Results are expressed as arithmetic average±SEM. **$p<0.01$.

FIG. 12 provides a graph showing the total number of lymphocytes recovered in guinea pig BAL fluid on the day of section. Results are expressed as arithmetic average±SEM. *$p<0.05$.

FIG. 13 provides a graph showing the total number of neutrophils recovered in guinea pig BAL fluid on the day of section. Results are expressed as arithmetic average±SEM. *$p<0.05$, ***$p<0.001$.

FIG. 14 provides a graph showing the total number of eosinophils recovered in guinea pig BAL fluid on the day of section. Results are expressed as arithmetic average±SEM. *$p<0.05$, ***$p<0.001$.

FIG. 15 provides a graph showing the percent change in Penh at Mch 48 mg/mL in the effect of sialidase treatment on the early and late asthmatic reaction in guinea pigs.

FIG. 16 provides a graph showing the percent change in Pehn at a range of Mch concentrations in the effect of sialidase treatment on the early and late asthmatic reaction in guinea pigs.

FIG. 17 provides a graph showing blood Eosinophils in the effect of sialidase treatment on the early and late asthmatic reaction in guinea pigs.

FIG. 18 provides a graph showing PAS staining for lung mucus in the effect of sialidase treatment on the early and late asthmatic reaction in guinea pigs.

FIGS. 19A-F provide a PAS staining for lung mucus.

FIG. 20 provides a graph showing MBP immunostaining for eosinophils in the effect of sialidase treatment on the early and late asthmatic reaction in guinea pigs.

FIGS. 21A-B provide graphs showing reduced airway resistance in naïve mice treated intranasally with low doses of DAS181 (methacholine challenged).

FIG. 22 provides a graph showing reduced airway resistance in naïve mice treated intranasally with a low dose of DAS181 (methacholine challenged).

FIG. 23 provides a graph showing reduced airway resistance in naïve mice treated intranasally with DAS181 (carbachol challenged).

FIG. 24 provides a graph showing airway resistance in naïve mice treated intranasally with a low dose of DAS185 (methacholine challenged).

FIG. 25 provides graphs showing time-course of DAS185 mediated reduction of airway resistance (methacholine challenged).

FIG. 26 provides a graph showing reduced airway resistance in naïve mice treated intranasally with very lose doses of DAS181 (methacholine challenged).

Like reference symbols in the various drawings indicate like elements.

DETAILED DESCRIPTION

The present disclosure provides, inter alia, novel methods of use for compounds described in U.S. patent application Ser. Nos. 10/718,986 and 10/939,262 (both of which are hereby incorporated by reference in their entirety) to reduce mucus, e.g., in the respiratory tract of subjects with elevated levels of mucus in their respiratory tract. In some embodiments, the present disclosure provides compositions and methods for reducing mucus (e.g., mucus levels) in a subject in need of reduced mucus levels and that does not have influenza (e.g., is not infected with influenza at the time of treatment) or ashma.

Figure 7A:
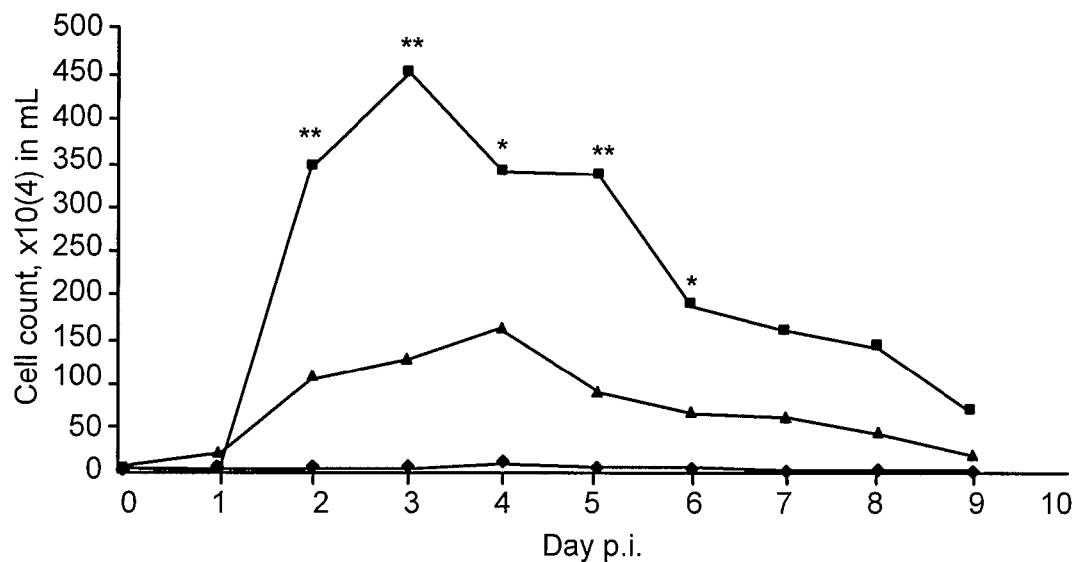
FIGS. 7A-B are graphs showing that topical administration of recombinant AR-AvCD sialidase fusion protein reduces the inflammatory responses of ferrets infected with an influenza A (H1N1) virus.

In some embodiments, the compounds can include compounds made by NexBio, Inc. under the compound name DAS181 and under the trademark Fludase® (provided herein as SEQ ID NO:21). DAS181 is a fusion protein comprising a catalytic domain of a sialidase, and an anchoring domain. Several of the examples described herein use DAS181 or compositions containing DAS181.

DEFINITIONS

Unless defined otherwise, all technical and scientific terms used herein have the same meaning as commonly understood by one of ordinary skill in the art to which this invention belongs. Generally, the nomenclature used herein and the manufacture or laboratory procedures described below are well known and commonly employed in the art. Conventional methods are used for these procedures, such as those provided in the art and various general references. Where a term is provided in the singular, the inventors also contemplate the plural of that term. Where there are discrepancies in terms and definitions used in references that are incorporated by reference, the terms used in this application shall have the definitions given herein. As employed throughout the disclosure, the following terms, unless otherwise indicated, shall be understood to have the following meanings:

As used herein, a "subject" includes any animal for whom diagnosis, screening, monitoring or treatment is contemplated. Animals include mammals such as primates and domesticated animals. An exemplary primate is human. A patient refers to a subject such as a mammal, primate, human or livestock subject afflicted with a disease condition or for which a disease condition is to be determined or risk of a disease condition is to be determined.

In some embodiments, the methods disclosed herein can include selecting a subject in need of reduced mucus levels and that is not infected with one or more of influenza, parainfluenza, and/or respiratory syncytial virus (RSV). In some instances, the terms infected or infection can include the presence of a influenza and/or parainfluenza virus and/or RSV in a subject. In some instances, the terms infected or infection can include the presence of active or replicating influenza and/or parainfluenza virus and/or RSV in a subject. In some embodiments, a subject with an active or replicating influenza and/or parainfluenza virus and/or RSV infection can be selected based on the presence or detection of influenza and/or parainfluenza virus shedding and/or RSV shedding in the subject (e.g., in a sample from the subject). In some embodiments, the methods disclosed herein can include selecting a subject in need of reduced mucus levels, wherein the subject has a latent influenza, parainfluenza, and/or RSV infection.

An "animal model" as used herein means an animal that sufficiently mimics, resembles or reproduces a disease or condition of interest in its anatomy, physiology, or response (to a pathogen or allergen, e.g.) so as to be useful in medical research that can be extrapolated to the disease or condition of interest (e.g., to screen for diagnostic or therapeutic agents; to measure therapeutic efficacy of a compound or composition, etc.). For example, the guinea pig and the mouse can be animal models to mimic imflammatory and/or allergic responses associated with asthma, as demonstrated in Examples 1 and 2, respectively. The mouse also can be an animal model to study the interaction of muscarinic receptors with their agonists, and the disruption thereof by agents such as the compounds and compositions provided herein (see Example 3).

A "pathogen" can be any virus or microorganism that can infect a cell, a tissue or an organism. A pathogen can be a virus, bacterium, or protozoan.

A "target cell" is any cell that can be infected by a pathogen or any cell that can interact with inflammatory cells, or a host cell that is the intended destination for an exogenous gene transferred by a recombinant virus.

"Inflammatory cells" are the cells that carry out or participate in inflammatory responses of the immune system. Inflammatory cells include B lymphocytes, T lymphocytes, macrophages, basophils, eosinophils, mast cells, NK cells, monocytes, and neutrophils.

An "extracellular activity that can inhibit adhesion or function of inflammatory cells" is any activity that can prevent inflammatory cells from contacting the target cell and affecting the normal physiological status of the target cell.

A "domain that can anchor said at least one therapeutic domain to the membrane of a target cell", also called an "extracellular anchoring domain" or simply, "anchoring domain" refers to a chemical entity can that can stably bind a moiety that is at or on the exterior of a cell surface or is in close proximity to the surface of a cell. An extracellular anchoring domain can be reversibly or irreversibly linked to one or more moieties, such as one or more therapeutic domains, and thereby cause the one or more attached therapeutic moieties to be retained at or in close proximity to the exterior surface of a eukaryotic cell. An extracellular anchoring domain can bind at least one molecule on the surface of a target cell or at least one molecule found in close association with the surface of a target cell. For example, an extracellular anchoring domain can bind a molecule covalently or noncovalently associated with the cell membrane of a target cell, or can bind a molecule present in the extracellular matrix surrounding a target cell. An extracellular anchoring domain can be a peptide, polypeptide, or protein, and can also comprise any additional type of chemical entity, including one or more additional proteins, polypeptides, or peptides, a nucleic acid, peptide nucleic acid, nucleic acid analogue, nucleotide, nucleotide analogue, small organic molecule, polymer, lipids, steroid, fatty acid, carbohydrate, or a combination of any of these.

As used herein, a protein or peptide sequences is "substantially homologous" to a reference sequence when it is either identical to a reference sequence, or comprises one or more amino acid deletions, one or more additional amino acids, or more one or more conservative amino acid substitutions, and retains the same or essentially the same activity as the reference sequence. Conservative substitutions may be defined as exchanges within one of the following five groups:

I. Small, aliphatic, nonpolar or slightly polar residues: Ala, Ser, Thr, Pro, Gly
  II. Polar, negatively charged residues and their amides: Asp, Asn, Glu, Gln
  III. Polar, positively charged residues: His, Arg, Lys
  IV. Large, aliphatic nonpolar residues: Met, Leu, Ile, Val, Cys
  V. Large aromatic residues: Phe, Try, Trp Within the foregoing groups, the following substitutions are considered to be "highly conservative": Asp/Glu, His/Arg/Lys, Phe/Tyr/Trp, and Met/Leu/Ile/Val. Semi-conservative substitutions are defined to be exchanges between two of groups (I)-(IV) above which are limited to supergroup (A), comprising (I), (II), and (III) above, or to supergroup (B), comprising (IV) and (V) above. In addition, where hydrophobic amino acids are specified in the application, they refer to the amino acids Ala, Gly, Pro, Met, Leu, Ile, Val, Cys, Phe, and Trp, whereas hydrophilic amino acids refer to Ser, Thr, Asp, Asn, Glu, Gln, His, Arg, Lys, and Tyr.

A "sialidase" is an enzyme that can remove a sialic acid residue from a substrate molecule. The sialidases (N-acyl-neuraminosylglycohydrolases, EC 3.2.1.18) are a group of enzymes that hydrolytically remove sialic acid residues from sialo-glycoconjugates. Sialic acids are alpha-keto acids with 9-carbon backbones that are usually found at the outermost positions of the oligosaccharide chains that are attached to glycoproteins and glycolipids. One of the major types of sialic acids is N-acetylneuraminic acid (Neu5Ac), which is the biosynthetic precursor for most of the other types. The substrate molecule can be, as nonlimiting examples, an oligosaccharide, a polysaccharide, a glycoprotein, a ganglioside, or a synthetic molecule. For example, a sialidase can cleave bonds having alpha(2,3)-Gal, alpha(2,6)-Gal, or alpha (2,8)-Gal linkages between a sialic acid residue and the remainder of a substrate molecule. A sialidase can also cleave any or all of the linkages between the sialic acid residue and the remainder of the substrate molecule. Two major linkages between Neu5Ac and the penultimate galactose residues of carbohydrate side chains are found in nature, Neu5Ac alpha (2,3)-Gal and Neu5Ac alpha (2,6)-Gal. Both Neu5Ac alpha (2,3)-Gal and Neu5Ac alpha (2,6)-Gal molecules can be recognized by influenza viruses as the receptor, although human viruses seem to prefer Neu5Ac alpha (2,6)-Gal, avian and equine viruses predominantly recognize Neu5Ac alpha (2,3)-Gal. A sialidase can be a naturally-occurring sialidase, an engineered sialidase (such as, but not limited to a sialidase whose amino acid sequence is based on the sequence of a naturally-occurring sialidase, including a sequence that is substantially homologous to the sequence of a naturally-occurring sialidase). As used herein, "sialidase" can also mean the active portion of a naturally-occurring sialidase, or a peptide or protein that comprises sequences based on the active portion of a naturally-occurring sialidase.

A "fusion protein" is a protein comprising amino acid sequences from at least two different sources. A fusion protein can comprise amino acid sequence that is derived from a naturally occurring protein or is substantially homologous to all or a portion of a naturally occurring protein, and in addition can comprise from one to a very large number of amino acids that are derived from or substantially homologous to all or a portion of a different naturally occurring protein. In the alternative, a fusion protein can comprise amino acid sequence that is derived from a naturally occurring protein or is substantially homologous to all or a portion of a naturally occurring protein, and in addition can comprise from one to a very large number of amino acids that are synthetic sequences.

A "sialidase catalytic domain protein" is a protein that comprises the catalytic domain of a sialidase, or an amino acid sequence that is substantially homologous to the catalytic domain of a sialidase, but does not comprises the entire amino acid sequence of the sialidase the catalytic domain is derived from, wherein the sialidase catalytic domain protein retains substantially the same activity as the intact sialidase the catalytic domain is derived from. A sialidase catalytic domain protein can comprise amino acid sequences that are not derived from a sialidase, but this is not required. A sialidase catalytic domain protein can comprise amino acid sequences that are derived from or substantially homologous to amino acid sequences of one or more other known proteins, or can comprise one or more amino acids that are not derived from or substantially homologous to amino acid sequences of other known proteins.

"Therapeutically effective amount" means an amount of a composition or compound that is needed for a desired therapeutic, prophylactic, or other biological effect or response when a composition or compound is administered to a subject in a single dosage form. The particular amount of the composition or compound will vary widely according to conditions such as the nature of the composition or compound, the nature of the condition being treated, the age and size of the subject.

"Treatment" means any manner in which one or more of the symptoms of a condition, disorder or disease are ameliorated or otherwise beneficially altered. Treatment also encompasses any pharmaceutical use of the composition or compound herein, such as for reducing mucus in the respiratory tract.

"Respiratory tract" means the air passages from the nose to the pulmonary alveoli, including the nose, throat, pharynx, larynx, trachea, and bronchi, and it also includes the lungs, and is sometimes referred to by medical practitioners as the respiratory system.

"Inhaler" means a device for giving medicines in the form of a spray or dry powder that is inhaled (breathed in either naturally or mechanically forced in to the lungs) through the nose or mouth, and includes without limitation, a passive or active ventilator (mechanical with or with an endotracheal tube), nebulizer, dry powder inhaler, metered dose inhaler, and pressureized metered dose inhaler.

"Inhalant" is any substance that is inhaled through the nose or mouth.

"Reducing the quantity of mucus" means diminishing all or some, generally more than by 5%, 10%, 20%, 30%, 40%, 50%, 60%, 70%, 80%, 85%, 90% 91%, 92%, 93%, 94%, 95%, 96%, 97%, 98% or 99% or more of the amount of mucus in the respiratory tract when compared with the amount prior to administration of the compositions or compounds described herein. "Reducing the quantity of mucus" can also mean reducing the amount of mucus in an amount that is observable by a healthcare practitioner using whatever medical implements are available for such observation, such as, e.g., by auscultation, by MRI or other radiographic study, by direct visualization with a bronchoscope or other visualization device, or by measuring patient mucus over time. "Reducing the quantity of mucus" can also mean reducing the amount of mucus in an amount that is observable by the patient or subject himself or herself with self-reporting or self-observation, such as, e.g., monitoring the amount of expectorated or swallowed mucus over time, or by subjectively observing the sense of congestion in his or her lungs over time.

"Limiting an increase in the quantity of mucus" means that the amount of mucus in the respiratory tract after administration of the compositions and compounds described herein does not increase more than if they had not been administered. "Limiting an increase in the quantity of mucus" also means that the amount of mucus in the respiratory tract after administration of the compositions and compounds described herein does not increase after their adminisation of the compositions and compounds. "Limiting an increase in the quantity of mucus" can also mean limiting an increase over the patient's baseline at the time of administration of the compounds or compositions in an amount that is observable or ascertainable by a healthcare practitioner using whatever medical implements and analytical systems are available for such observations, such as, e.g., by auscultation, by MRI or other radiographic study, by direct visualization with a bronchoscope or other visualization device, or by measuring patient sputum over time. "Limiting an increase in the quantity of mucus" can also mean limiting an increase over the patient's baseline at the time of administration of the compounds or compositions in an amount that is observable by the patient or subject himself or herself with self-reporting or self-observation, such as, e.g., monitoring the amount of expectorated or swallowed mucus over time, or by subjectively observing the sense of congestion in his or her lungs over time.

"Excipient" as used herein means one or more inactive substances or compounds that either alone or in combination are used as a carrier for the active ingredients of a medication. As used herein "excipient" can also mean one or more substances or compounds that are included in a pharmaceutical composition to improve its beneficial effects or that have a synergistic effect with the active ingredient.

Peptide or Protein Based Compounds

The present invention includes peptide or protein-based compounds that comprise at least one domain that can anchor the compound to the membrane of a eukaryotic cell and at least one additional domain that is a therapeutic domain. By "peptide or protein-based" compounds, it is meant that the two major domains of the compound have an amino acid framework, in which the amino acids are joined by peptide bonds. A peptide or protein-based compound can also have other chemical compounds or groups attached to the amino acid framework or backbone, including moieties that contribute to the anchoring activity of the anchoring domain, or moieties that contribute to the therapeutic activity of the therapeutic domain. For example, the protein-based therapeutics used in the present invention can comprise compounds and molecules such as but not limited to: carbohydrates, fatty acids, lipids, steroids, nucleotides, nucleotide analogues, nucleic acid molecules, nucleic acid analogues, peptide nucleic acid molecules, small organic molecules, or even polymers. The protein-based therapeutics of the present invention can also comprise modified or non-naturally occurring amino acids. Non-amino acid portions of the compounds can serve any purpose, including but not limited to: facilitating the purification of the compound, improving the solubility or distribution or the compound (such as in a therapeutic formulation), linking domains of the compound or linking chemical moieties to the compound, contributing to the two-dimensional or three-dimensional structure of the compound, increasing the overall size of the compound, increasing the stability of the compound, and contributing to the anchoring activity or therapeutic activity of the compound.

The peptide or protein-based compounds of the present invention can also include protein or peptide sequences in addition to those that comprise anchoring domains or therapeutic domains. The additional protein sequences can serve any purpose, including but not limited to any of the purposes outlined above (facilitating the purification of the compound, improving the solubility or distribution or the compound, linking domains of the compound or linking chemical moieties to the compound, contributing to the two-dimensional or three-dimensional structure of the compound, increasing the overall size of the compound, increasing the stability of the compound, or contributing to the anchoring activity or therapeutic activity of the compound). Any additional protein or amino acid sequences can be part of a single polypeptide or protein chain that includes the anchoring domain or domains and therapeutic domain or domains, but any feasible arrangement of protein sequences is within the scope of the present invention.

The anchoring domain and therapeutic domain can be arranged in any appropriate way that allows the compound to bind at or near a target cell membrane. The compound can have at least one protein or peptide-based anchoring domain and at least one peptide or protein-based therapeutic domain. In this case, the domains can be arranged linearly along the peptide backbone in any order. The anchoring domain can be N-terminal to the therapeutic domain, or can be C-terminal to the therapeutic domain. It is also possible to have one or more therapeutic domains flanked by at least one anchoring domain on each end. Alternatively, one or more anchoring domains can be flanked by at least one therapeutic domain on each end. Chemical or peptide linkers can optionally be used to join some or all of the domains of a compound.

It is also possible to have the domains in a nonlinear, branched arrangement. For example, the therapeutic domain can be attached to a derivatized side chain of an amino acid that is part of a polypeptide chain that also includes, or is linked to, the anchoring domain.

A compound of the present invention can have more than one anchoring domain. In cases in which a compound has more than one anchoring domain, the anchoring domains can be the same or different. A compound used in the present invention can have more than one therapeutic domain. In cases in which a compound has more than one therapeutic domain, the therapeutic domains can be the same or different. Where a compound comprises multiple anchoring domains, the anchoring domains can be arranged in tandem (with or without linkers) or on alternate sides of other domains, such as therapeutic domains. Where a compound comprises multiple therapeutic domains, the therapeutic domains can be arranged in tandem (with or without linkers) or on alternate sides of other domains, such as, but not limited to, anchoring domains.

A peptide or protein-based compound of the present invention can be made by any appropriate way, including purifying naturally occurring proteins, optionally proteolytically cleaving the proteins to obtain the desired functional domains, and conjugating the functional domains to other functional domains. Peptides can also be chemically synthesized, and optionally chemically conjugated to other peptides or chemical moieties. A peptide or protein-based compound of the present invention can be made by engineering a nucleic acid construct to encode at least one anchoring domain and at least one therapeutic domain together (with or without nucleic acid linkers) in a continuous polypeptide. The nucleic acid constructs, in some embodiments having appropriate expression sequences, can be transfected into prokaryotic or eukaryotic cells, and the therapeutic protein-based compound can be expressed by the cells and purified. Any desired chemical moieties can optionally be conjugated to the peptide or protein-based compound after purification. In some cases, cell lines can be chosen for expressing the protein-based therapeutic for their ability to perform desirable post-translational modifications (such as, but not limited to glycosylation).

A great variety of constructs can be designed and their protein products tested for desirable activities (such as, for example, binding activity of an anchoring domain, or a binding, catalytic, or inhibitory activity of a therapeutic domain).

Anchoring Domain

As used herein, an "extracellular anchoring domain" or "anchoring domain" is any moiety that can stably bind an entity that is at or on the exterior surface of a target cell or is in close proximity to the exterior surface of a target cell. An anchoring domain serves to retain a compound used in the present invention at or near the external surface of a target cell.

An extracellular anchoring domain can bind 1) a molecule expressed on the surface of a target cell, or a moiety, domain, or epitope of a molecule expressed on the surface of a target cell, 2) a chemical entity attached to a molecule expressed on the surface of a target cell, or 3) a molecule of the extracellular matrix surrounding a target cell.

An anchoring domain can be a peptide or protein domain (including a modified or derivatized peptide or protein domain), or comprises a moiety coupled to a peptide or protein. A moiety coupled to a peptide or protein can be any type of molecule that can contribute to the binding of the anchoring domain to an entity at or near the target cell surface, and in some embodiments is an organic molecule, such as, for example, nucleic acid, peptide nucleic acid, nucleic acid analogue, nucleotide, nucleotide analogue, small organic molecule, polymer, lipids, steroid, fatty acid, carbohydrate, or any combination of any of these.

A molecule, complex, domain, or epitope that is bound by an anchoring domain may or may not be specific for the target cell. For example, an anchoring domain may bind an epitope present on molecules on or in close proximity to the target cell and that occur at sites other than the vicinity of the target cell as well. In many cases, however, localized delivery of a therapeutic compound of the present invention will restrict its occurrence primarily to the surface of target cells. In other cases, a molecule, complex, moiety, domain, or epitope bound by an anchoring domain may be specific to a target tissue or target cell type.

Target tissue or target cell type includes the sites in an animal or human body where a pathogen invades or amplifies. For example, a target cell can be an endothelial cell that can be infected by a pathogen. A composition used in the present invention can comprise an anchoring domain that can bind a cell surface epitope, for example, that is specific for the endothelial cell type. In another example, a target cell can be an epithelial cell and a composition of the present invention can bind an epitope present on the cell surface of many epithelial cell types, or present in the extracellular matrix of different types of epithelial cells. In this case localized delivery of the composition can restrict its localization to the site of the epithelial cells that are targets of the pathogen.

Compounds used in the present invention can have one or more anchoring domains that can bind at or near the surface of epithelial cells. For example, heparan sulfate, closely related to heparin, is a type of glycosaminoglycan (GAG) that is ubiquitously present on cell membranes, including the surface of respiratory epithelium. Many proteins specifically bind to heparin/heparan sulfate, and the GAG-binding sequences in these proteins have been identified (Meyer, F A, King, M and Gelman, R A. (1975) *Biochimica et Biophysica Acta* 392: 223-232; Schauer, S. ed., pp 233. Sialic Acids Chemistry, Metabolism and Function. Springer-Verlag, 1982). For example, the GAG-binding sequences of human platelet factor 4 (PF4) (SEQ ID NO:2), human interleukin 8 (IL8) (SEQ ID NO:3), human antithrombin III (AT III) (SEQ ID NO:4), human apoprotein E (ApoE) (SEQ ID NO:5), human angio-associated migratory cell protein (AAMP) (SEQ ID NO:6), or human amphiregulin (SEQ ID NO:7) (FIG. 1) have been shown to have very high affinity (in the nanomolar range) towards heparin (Lee, M K and Lander, A D. (1991) Pro Natl Acad Sci USA 88:2768-2772; Goger, B, Halden, Y, Rek, A, Mosl, R, Pye, D. Gallagher, J and Kungl, A J. (2002) Biochem. 41:1640-1646; Witt, D P and Lander A D (1994) Curr Bio 4:394-400; Weisgraber, K H, Rall, S C, Mahley, R W, Milne, R W and Marcel, Y. (1986) J Bio Chem 261:2068-2076). The GAG-binding sequences of these proteins are distinct from their receptor-binding sequences, so they will not induce the biological activities associated with the full-length proteins or the receptor-binding domains. These sequences, or other sequences that have been identified or are identified in the future as heparin/heparan sulfate binding sequences, or sequences substantially homologous to identified heparin/heparan sulfate binding sequences that have heparin/heparan sulfate binding activity, can be used as epithelium-anchoring-domains in compounds used in the present invention.

An anchoring domain can bind a moiety that is specific to the target cell type of a particular species or can bind a moiety that is found in the target cell type of more than one species.

Therapeutic Domain

A compound used in the present invention includes at least one therapeutic domain or active portion, those terms being used interchangeable herein. The therapeutic activity can be, as nonlimiting examples, a binding activity, a catalytic activity, or an inhibitory activity. A therapeutic domain can modify or inhibit a function of the target cell or target organism. An active portion of a compound has therapeutic activity. For example, the catalytic domain or active portion of a sialidase can be its therapeutic domain.

The therapeutic domain can act extracellularly, meaning that its infection-preventing, inflammatory response-modulating, or transduction-enhancing activity takes place at the target cell surface or in the immediate area surrounding the target cell, including sites within the extracellular matrix, intracellular spaces, or luminal spaces of tissues.

A therapeutic domain can be a peptide or protein domain (including a modified or derivatized peptide or protein domain), or comprises a moiety coupled to a peptide or protein. A moiety coupled to a peptide or protein can be any type of molecule, and is in some embodiments an organic molecule, such as, for example, nucleic acid, peptide nucleic acid, nucleic acid analogue, nucleotide, nucleotide analogue, small organic molecule, polymer, lipids, steroid, fatty acid, carbohydrate, or any combination of any of these.

A therapeutic domain can be a synthetic peptide or polypeptide, or can comprise a synthetic molecule that can be conjugated to a peptide or polypeptide, can be a naturally-occurring peptide or protein, or a domain of naturally-occurring protein. A therapeutic domain can also be a peptide or protein that is substantially homologous to a naturally-occurring peptide or protein.

Linkers

A compound used in the present invention can optionally include one or more linkers that can join domains of the compound. Linkers can be used to provide optimal spacing or folding of the domains of a compound. The domains of a compound joined by linkers can be therapeutic domains, anchoring domains, or any other domains or moieties of the compound that provide additional functions such as enhancing compound stability, facilitating purification, etc. A linker used to join domains of compounds of the present invention can be a chemical linker or an amino acid or peptide linker. Where a compound comprises more than one linker, the linkers can be the same or different. Where a compound comprises more than one linker, the linkers can be of the same or different lengths.

Many chemical linkers of various compositions, polarity, reactivity, length, flexibility, and cleavability are known in the art of organic chemistry. Preferred linkers include amino acid or peptide linkers. Peptide linkers are well known in the art. Some embodiments of linkers are between one and about one hundred amino acids in length, and between one and about thirty amino acids in length, although length is not a limitation in the linkers of the compounds of the present invention. The linkder amino acid sequences can be selected such that they do not interfere with the mucus-reducing and/or anti-inflammatory activity of the compounds and compositions used in the present invention. Some embodiments of linkers are those that include the amino acid glycine. For example, linkers having the sequence:
(GGGGS (SEQ ID NO:10))n, where n is a whole number between 1 and 20, or between 1 and 12, can be used to link domains of therapeutic compounds used in the present invention.

Composition Comprising at Least One Anchoring Domain and at Least One Catalytic Activity In some aspects, the present invention can use compounds that have a therapeutic domain that has an enzymatic activity. The enzymatic activity can be a catalytic activity that removes, degrades or modifies a host molecule or complex. In some embodiments the host molecule or complex can be removed, degraded, or modified by the enzymatic activity of a compound of the present invention is on, at, or near the surface of a target cell.

Compounds used in the present invention can have, for example, one of the following structures:
(Anchoring Domain)n-[linker]-(Enzymatic Activity)n (n=1, 2, 3 or more)
or:
(Enzymatic Activity)n (n=1, 2, 3 or more)-[linker]-(Anchoring Domain)n,
where the linkers are optional.

The enzymatic activity can be a monomeric form of a peptide or polypeptide or can be multiple copies of the same polypeptide that are either linked directly or with spacing sequence in between. The polypeptides or peptides can be linked directly or via a spacer composed of peptide linker sequence. The anchoring domain can be any peptide or polypeptide that can bind to or near the surface of target cells.

In one embodiment, a therapeutic domain comprises a sialidase that can eliminate or greatly reduce the level of sialic acid on the surface of epithelial cells. The therapeutic domain can comprise a complete sialidase protein, or an active portion thereof, wherein the active portion thereof retains the ability to perform the catalytic function(s) of the sialidase protein (e.g., cleaving sialic acid residues).

Sialic acid mediates cell adhesion and interactions between inflammatory cells and target cells. Therefore, treating the surface of respiratory epithelial cells with a sialidase can prevent the recruitment of inflammatory cells to the airway surface, and therefore can treat allergic reactions including asthma and allergic rhinitis. It also unexpectedly results in reducing the quantity of mucus in the respiratory tract of subjects with elevated levels of mucus in their respiratory tract, and limiting increase in the quantity of mucus in the respiratory tract of subjects above a baseline of mucus in the respiratory tract of those subjects.

Among the sialidases contemplated for use in the methods described herein are the large bacterial sialidases that can degrade the receptor sialic acids Neu5Ac alpha(2,6)-Gal and Neu5Ac alpha(2,3)-Gal. For example, the bacterial sialidase enzymes from *Clostridium perfringens* (Genbank Accession Number X87369), *Actinomyces viscosus, Arthrobacter ureafaciens*, or *Micromonospora viridifaciens* (Genbank Accession Number D01045) can be used. Therapeutic domains of compounds of the present invention can comprise all or a portion of the amino acid sequence of a large bacterial sialidase or can comprise amino acid sequences that are substantially homologous to all or a portion of the amino acid sequence of a large bacterial sialidase. In one preferred embodiment, a therapeutic domain comprises a sialidase encoded by *Actinomyces viscosus*, such as that of SEQ ID NO:12, or such as sialidase sequence substantially homologous to SEQ ID NO:12. In yet another preferred embodiment, a therapeutic domain comprises the catalytic domain of the *Actinomyces viscosus* sialidase extending from amino acids 274-667 of SEQ ID NO:12, or a substantially homologous sequence.

Other sialidases contemplated for use in the methods described herein are the human sialidases such as those encoded by the genes NEU2 (SEQ ID NO:8; Genbank Accession Number Y16535; Monti, E, Preti, Rossi, E., Ballabio, A and Borsani G. (1999) *Genomics* 57:137-143) and NEU4 (SEQ ID NO:9; Genbank Accession Number NM080741; Monti, E, Preti, A, Venerando, B. and Borsani, G. (2002) *Neurochem Res* 27:646-663) (FIG. 2). Therapeutic domains of compounds used in the present invention can comprise all or a portion of the amino acid sequences of a human sialidase or can comprise amino acid sequences that are substantially homologous to all or a portion of the amino acid sequences of a human sialidase. Where a therapeutic domain comprises a portion of the amino acid sequences of a naturally occurring sialidase, or sequences substantially homologous to a portion of the amino acid sequences of a naturally occurring sialidase, the portion can have essentially the same activity as the human sialidase.

A compound for reducing elevated levels of mucus in the respiratory tract can in some embodiments have one or anchoring domains that can bind at or near the surface of epithelial cells. In some embodiments, the epithelium-anchoring domain is a GAG-binding sequence from a human protein, such as, for example, the GAG-binding amino acid sequences of human platelet factor 4 (PF4) (SEQ ID NO:2), human interleukin 8 (IL8) (SEQ ID NO:3), human antithrombin III (AT III) (SEQ ID NO:4), human apoprotein E (ApoE) (SEQ ID NO:5), human angio-associated migratory cell protein (AAMP) (SEQ ID NO:6), and human amphiregulin (SEQ ID NO:7) (FIG. 1). An epithelial anchoring domain can also be substantially homologous to a naturally occurring GAG-binding sequence, such as those listed in FIG. 1. Such compounds can be formulated for nasal, tracheal, bronchial, oral, or topical administration, or can be formulated as an injectable solution or as eyedrops, or formulated into a solution or dry powder and inhaled with inhalers.

A pharmaceutical composition comprising such compounds can be used to treat or prevent allergy or inflammatory response. In addition, such compounds have been shown herein to reduce the quantity of mucus in the respiratory tract of subjects with elevated levels of mucus in their respiratory tracts, and to limit increases in the quantity of mucus in the respiratory tract of subjects above a baseline of mucus in their respiratory tracts. Therefore, such compounds can be used to as therapeutic treatments to reduce the quantity of mucus in the respiratory tract of subjects with elevated levels of mucus in their respiratory tracts, or as prophylactic treatments to limit increases in the quantity of mucus in the respiratory tract of subjects above a baseline of mucus in their respiratory tracts. Due to their effect on mucus in the respiratory tract, these compounds can also be used to prevent, treat, or ameliorate the effects of chronic obstructive pulmonary disease (COPD), bronchitis, bronchiectasis, cystic fibrosis (CF), vasculitis, mucus plugging, Wegener's granulomatosis, pneumonia, tuberculosis, cancer involving the lungs or the respiratory tract, Kartagener syndrome, Young's syndrome, chronic sinopulmonary infection, alpha 1-antitrypsin deficiency, primary immunodeficiency, acquired immune deficiency syndrome, opportunistic infection, an infectious state, a post infectious state, common cold, exercise induced hypersecretion of mucus, inflammatory bowel disease, ulcerative colitis, Crohn's disease, respiratory infection, respiratory obstruction, inhalation or aspiration of a toxic gas, pulmonary aspiration, or alcoholism in subjects with elevated levels of mucus in their respiratory tract or who are at risk of having increased levels of mucus in their respiratory tract.

It is also within the scope of the present invention to use compounds or compositions comprising a human sialidase, such as any of those described herein, or an active portion thereof, or a compound with substantial homology to a sialidase, in the absence of an anchoring domain (a) to treat or prevent allergic and inflammatory responses in the respiratory tract, (b) to reduce the quantity of mucus in the respiratory tract of subjects with elevated levels of mucus in their respiratory tracts, (c) to limit increases in the quantity of mucus in the respiratory tract of subjects above a baseline of mucus in their respiratory tracts, and/or (d) to prevent, treat, or ameliorate the effects of chronic obstructive pulmonary disease (COPD), bronchitis, bronchiectasis, cystic fibrosis (CF), vasculitis, mucus plugging, Wegener's granulomatosis, pneumonia, tuberculosis, cancer involving the lungs or the respiratory tract, Kartagener syndrome, Young's syndrome, chronic sinopulmonary infection, alpha 1-antitrypsin deficiency, primary immunodeficiency, acquired immune deficiency syndrome, opportunistic infection, an infectious state, a post infectious state, common cold, exercise induced hypersecretion of mucus, inflammatory bowel disease, ulcerative colitis, Crohn's disease, respiratory infection, respiratory obstruction, inhalation or aspiration of a toxic gas, pulmonary aspiration, or alcoholism in subjects with elevated levels of mucus in their respiratory tract or who are at risk of having increased levels of mucus in their respiratory tract. The present invention recognizes that elevated levels of mucus in the respiratory tract can be reduced by the use of a sialidase or an active portion of a sialidase, and that such sialidases or active portions thereof can optionally be adapted, by genetic or chemical engineering, or by pharmaceutical formulation, to improve their half life or retention at the respiratory epithelium.

These compounds and pharmaceutical compositions can be delivered to the upper respiratory tract as a nasal spray, or delivered to the respiratory tract as an inhalant with inhalers.

The compounds described herein can be formulated into pharmaceutical compositions that include various additional compounds either alone or in various combinations, such as, $Na_2SO_4$, $MgSO_4$, $CaCl_2$, Histidine, Histine-HCl, and Trehalose or their analogs. These additional compounds can be included in the pharmaceutical compositions to act as excipients or as active ingredients that provide additional beneficial effects.

Therapeutic Composition Comprising at Least One Sialidase Activity

The present invention includes methods that use therapeutic compounds and compositions that comprise at least one sialidase activity. The sialidase activity can be a sialidase isolated from any source, such as, for example, a bacterial or mammalian source, or can be a recombinant protein that is substantially homologous to at least a portion of a naturally occurring sialidase. In some embodiments sialidases are the large bacterial sialidases that can degrade the receptor sialic acids Neu5Ac alpha(2,6)-Gal and Neu5Ac alpha(2,3)-Gal. For example, the bacterial sialidase enzymes from *Clostridium perfringens* (Genbank Accession Number X87369), *Actinomyces viscosus* (Genbank Accession Number L06898), *Arthrobacter ureafaciens*, or *Micromonospora viridifaciens* (Genbank Accession Number D01045) or substantially homologous proteins can be used.

For example, therapeutic compounds and compositions used in the present invention can comprise a large bacterial sialidase or can comprise a protein with the amino acid sequence of a large bacterial sialidase or can comprise amino acid sequences that are substantially homologous to the amino acid sequence of a large bacterial sialidase. A pharmaceutical composition that can be used in the present invention comprises the *A. viscosus* sialidase (SEQ ID NO:12), or comprises a protein substantially homologous to the *A. viscosus* sialidase.

Other sialidases that can be used in the compositions, compounds and methods described herein are the human sialidases such as those encoded by the genes NEU2 (SEQ ID NO:8; Genbank Accession Number Y16535; Monti, E, Preti, Rossi, E., Ballabio, A and Borsani G. (1999) *Genomics* 57:137-143) and NEU4 (SEQ ID NO:9; Genbank Accession Number NM080741; Monti, E, Preti, A, Venerando, B and Borsani, G. (2002) *Neurochem Res* 27:646-663) (FIG. 2). Therapeutic domains of compounds of the present invention can comprise a human sialidase protein that is substantially homologous to the amino acid sequences of a human sialidase or can comprise amino acid sequences that are substantially homologous to all or a portion of the amino acid sequences of a human sialidase. Where a therapeutic domain comprises a portion of the amino acid sequences of a naturally occurring sialidase, or sequences substantially homologous to a portion of the amino acid sequences of a naturally occurring sialidase, the portion can have essentially the same activity as the human sialidase, e.g., an active portion of the sialidase.

Generally, sialidases that can effectively degrade on respiratory epithelial cells both receptor sialic acids Neu5Ac α(2, 6)-Gal and Neu5Ac α(2,3)-Gal, can be used. Sialidases are found in higher eukaryotes, as well as in some mostly pathogenic microbes, including viruses, bacteria and protozoans. Viral and bacterial sialidases have been well characterized, and the three-dimensional structures of some of them have been determined (Crennell, S J, Garman, E, Layer, G, Vimr, E. and Taylor, G. (1994) *Structure* 2:535-544; Janakiraman, M N, White, C L, Layer, W G, Air, G M and Luo, M. (1994) *Biochemistry* 33:8172-8179; Pshezhetsky, A, Richard, C, Michaud, L, Igdoura, S, Wang, S, Elsliger, M, Qu, J, Leclerc, D, Gravel, R, Dallaire, L and Potier, M. (1997) *Nature Genet.* 15: 316-320). Several human sialidases have also been cloned in the recent years (Milner, C M, Smith, S V, Carrillo M B, Taylor, G L, Hollinshead, M and Campbell, R D. (1997) *J Bio Chem* 272:4549-4558; Monti, E, Preti, A, Nesti, C, Ballabio, A and Borsani G. 1999. *Glycobiol* 9:1313-1321; Wada, T, Yoshikawa, Y, Tokuyama, S, Kuwabara, M, Akita, H. and Miyagi, T. (1999) *Biochem Biophy Res Communi* 261:21-27; Monti, E, Bassi, M T, Papini, N, Riboni, M, Manzoni, M, Veneranodo, B, Croci, G, Preti, A, Ballabio, A, Tettamanti, G. and Borsani, G. (2000) *Bichem J* 349:343-351). DAS181, which contains an active portion of a sialidase, has also been cloned.

All the sialidases characterized share a four amino acid motif in the amino terminal portion followed by the Asp box motif which is repeated three to five times depending on the protein. (Monti, E, Bassi, M T, Papini, N, Riboni, M, Manzoni, M, Veneranodo, B, Croci, G, Preti, A, Ballabio, A, Tettamanti, G and Borsani, G. (2000) *Bichem J* 349:343-351; Copley, R R, Russell, R B and Ponting, C P. (2001) *Protein Sci* 10:285-292). While the overall amino acid identity of the sialidase superfamily is relatively low at about 20-30%, the overall fold of the molecules, especially the catalytic amino acids, are remarkably similar (Wada, T, Yoshikawa, Y, Tokuyama, S, Kuwabara, M, Akita, H and Miyagi, T. (1999) *Biochem Biophy Res Communi* 261:21-27; Monti, E, Bassi, M T, Papini, N, Riboni, M, Manzoni, M, Veneranodo, B, Croci, G, Preti, A, Ballabio, A, Tettamanti, G and Borsani, G. (2000) *Bichem J* 349:343-351; Copley, R R, Russell, R B and Ponting, C P. (2001) *Protein Sci* 10:285-292).

The sialidases are generally divided into two families: "small" sialidases have molecular weight of about 42 kDa and do not require divalent metal ion for maximal activity; "large" sialidases have molecular weight above 65 kDa and may require divalent metal ion for activity (Wada, T, Yoshikawa, Y, Tokuyama, S, Kuwabara, M, Akita, H. and Miyagi, T. (1999) *Biochem Biophy Res Communi* 261:21-27; Monti, E, Bassi, M T, Papini, N, Riboni, M, Manzoni, M, Veneranodo, B, Croci, G, Preti, A, Ballabio, A, Tettamanti, G and Borsani, G. (2000) *Bichem J* 349:343-351; Copley, R R, Russell, R B and Ponting, C P. (2001) *Protein Sci* 10:285-292).

Over fifteen sialidase proteins have been purified and they vary greatly from one another in substrate specificities and enzymatic kinetics. Large bacterial sialidases can effectively cleave sialic acid in both ($\alpha$,2-6) linkage and ($\alpha$,2-3) linkage in the context of most natural substrates (FIG. 4; Vimr, D R. (1994) *Trends Microbiol* 2: 271-277; Drzeniek, R. (1973) *Histochem J* 5:271-290; Roggentin, P, Kleineidam, R G and Schauer, R. (1995) *Biol Chem Hoppe-Seyler* 376:569-575; Roggentin, P, Schauer, R, Hoyer, L L and Vimr, E R. (1993) *Mol Microb* 9:915-921). Because of their broad substrate specificities, large bacterial sialidases make good candidates.

FIG. 4 shows several of the large bacterial sialidases with known substrate specificity. These enzymes have high specific activity (600 U/mg protein for *C. perfringens* (Corfield, A P, Veh, R W, Wember, M, Michalski, J C and Schauer, R. (1981) *Bichem J* 197:293-299) and 680 U/mg protein for *A. viscosus* (Teufel, M, Roggentin, P. and Schauer, R. (1989) *Biol Chem Hoppe Seyler* 370:435-443)), are fully active without divalent metal iron, and have been cloned and purified as recombinant proteins from *E. coli* (Roggentin, P, Kleineidam, R G and Schauer, R. (1995) *Biol Chem Hoppe-Seyler* 376: 569-575, Teufel, M, Roggentin, P. and Schauer, R. (1989) *Biol Chem Hoppe Seyler* 370:435-443, Sakurada, K, Ohta, T. and Hasegawa, M. (1992) *J Bacteriol* 174: 6896-6903). In addition, *C. perfringens* is stable in solution at 2-8° C. for several weeks, and at 4° C. in the presence of albumin for more than two years (Wang, F Z, Akula, S M, Pramod, N P, Zeng, L and Chandran, B. (2001) *J Virol* 75:7517-27). *A. viscosus* is labile towards freezing and thawing, but is stable at 4° C. in 0.1 M acetate buffer, pH 5 (Teufel, M, Roggentin, P. and Schauer, R. (1989) *Biol Chem Hoppe Seyler* 370:435-443).

A pharmaceutical composition comprising a sialidase can include other compounds, including but not limited to other proteins, that can also have therapeutic activity. A pharmaceutical composition comprising a sialidase can include other compounds that can enhance the stability, solubility, packaging, delivery, consistency, taste, or fragrance of the composition.

Compounds comprising a sialidase can be formulated for nasal, tracheal, bronchial, oral, or topical administration, or can be formulated as an injectable solution or as eyedrops, or formulated into a solution or dry powder and inhaled with inhalers. The sialidases described herein can be formulated into pharmaceutical compositions that include various additional compounds such as, $MgSO_4$, $CaCl_2$, Histidine, Histine-HCl, and Trehalose or their analogs.

These sialidases or pharmaceutical compositions containing them can be used (a) to treat or prevent allergic and inflammatory responses in the respiratory tract, (b) to reduce the quantity of mucus in the respiratory tract of subjects with elevated levels of mucus in their respiratory tracts, (c) to limit increases in the quantity of mucus in the respiratory tract of subjects above a baseline of mucus in their respiratory tracts, and/or (d) to prevent, treat, or ameliorate the effects of chronic obstructive pulmonary disease (COPD), bronchitis, bronchiectasis, cystic fibrosis (CF), vasculitis, mucus plugging, Wegener's granulomatosis, pneumonia, tuberculosis, cancer involving the lungs or the respiratory tract, Kartagener syndrome, Young's syndrome, chronic sinopulmonary infection, alpha 1-antitrypsin deficiency, primary immunodeficiency, acquired immune deficiency syndrome, opportunistic infection, an infectious state, a post infectious state, common cold, exercise induced hypersecretion of mucus, inflammatory bowel disease, ulcerative colitis, Crohn's disease, respiratory infection, respiratory obstruction, inhalation or aspiration of a toxic gas, pulmonary aspiration, or alcoholism in subjects with elevated levels of mucus in their respiratory tract or who are at risk of having increased levels of mucus in their respiratory tract. In some embodiments, subjects with elevated levels of mucus in their respiratory tract do not include subjects with one or more of influenza, parainfluenza, and/or respiratory syncytial virus (RSV).

Sialidase Catalytic Domain Proteins or Peptides

As used herein a "sialidase catalytic domain protein or peptide" comprises a catalytic domain of a sialidase but does not comprise the entire amino acid sequence of the sialidase from which the catalytic domain is derived. A sialidase catalytic domain protein or peptide has sialidase activity. A sialidase catalytic domain protein or peptide can have at least 10%, at least 20%, at least 50%, at least 70% of the activity of the sialidase from which the catalytic domain sequence is derived. A sialidase catalytic domain protein or peptide can have at least 90% of the activity of the sialidase from which the catalytic domain sequence is derived.

A sialidase catalytic domain protein or peptide can include other amino acid sequences, such as but not limited to additional sialidase sequences, sequences derived from other proteins, or sequences that are not derived from sequences of naturally-occurring proteins. Additional amino acid sequences can perform any of a number of functions, including contributing other activities to the catalytic domain protein, enhancing the expression, processing, folding, or stability of the sialidase catalytic domain protein, or even providing a desirable size or spacing of the protein or peptide.

A preferred sialidase catalytic domain protein or peptide is a protein that comprises the catalytic domain of the *A. viscosus* sialidase. An *A. viscosus* sialidase catalytic domain protein or peptide can include amino acids 270-667 of the *A. viscosus* sialidase sequence (SEQ ID NO:12). An *A. viscosus* sialidase catalytic domain protein or peptide can include amino acid sequence that begins at any of the amino acids from amino acid 270 to amino acid 290 of the *A. viscosus* sialidase sequence (SEQ ID NO:12) and ends at any of the amino acids from amino acid 665 to amino acid 901 of said *A. viscosus* sialidase sequence (SEQ ID NO:12), and lacks any *A. viscosus* sialidase protein sequence extending from amino acid 1 to amino acid 269. (As used herein "lacks any *A. viscosus* sialidase protein sequence extending from amino acid 1 to amino acid 269" means lacks any stretch of four or more consecutive amino acids as they appear in the designated protein or amino acid sequence.)

In some embodiments, an *A. viscosus* sialidase catalytic domain protein or peptide comprises amino acids 274-681 of the *A. viscosus* sialidase sequence (SEQ ID NO:12) and lacks other *A. viscosus* sialidase sequence. In other embodiments, an *A. viscosus* sialidase catalytic domain protein comprises amino acids 290-666 or 290-667 of the *A. viscosus* sialidase sequence (SEQ ID NO:12) and lacks any other *A. viscosus* sialidase sequence. In yet other embodiments, an *A. viscosus* sialidase catalytic domain protein or peptide comprises amino acids 274-666 of the *A. viscosus* sialidase sequence (SEQ ID NO:12) and lacks any other *A. viscosus* sialidase sequence. In yet other embodiments, an *A. viscosus* sialidase catalytic domain protein or peptide comprises amino acids 290-666 or 290-667 of the *A. viscosus* sialidase sequence (SEQ ID NO:12) and lacks any other *A. viscosus* sialidase sequence. In yet other embodiments, an *A. viscosus* sialidase catalytic domain protein or peptide comprises amino acids 290-681 of the *A. viscosus* sialidase sequence (SEQ ID NO:12) and lacks any other *A. viscosus* sialidase sequence.

Such sialidase catalytic domain proteins or peptides can be formulated for nasal, tracheal, bronchial, oral, or topical administration, or can be formulated as an injectable solution or as eyedrops, or formulated into a solution or dry powder and inhaled with an inhaler. The sialidase catalytic domain proteins or peptides described herein can be formulated into pharmaceutical compositions that include various additional compounds, such as, $MgSO_4$, $CaCl_2$, Histidine, Histine-HCl, and Trehalose or their analogs. These additional compounds can be included in the pharmaceutical compositions either alone or in various combinations, such as, $Na_2SO_4$, $MgSO_4$, $CaCl_2$, Histidine, Histine-HCl, and Trehalose or their analogs. These additional compounds can be included in the pharmaceutical compositions to act as excipients or as active ingredients that provide additional beneficial effects.

Such sialidase catalytic domain proteins or peptides or pharmaceutical compositions containing them can be used (a) to treat or prevent allergic and inflammatory responses in the respiratory tract, (b) to reduce the quantity of mucus in the respiratory tract of subjects with elevated levels of mucus in their respiratory tracts, (c) to limit increases in the quantity of mucus in the respiratory tract of subjects above a baseline of mucus in their respiratory tracts, and/or (d) to prevent, treat, or ameliorate the effects of chronic obstructive pulmonary disease (COPD), bronchitis, bronchiectasis, cystic fibrosis (CF), vasculitis, mucus plugging, Wegener's granulomatosis, pneumonia, tuberculosis, cancer involving the lungs or the respiratory tract, Kartagener syndrome, Young's syndrome, chronic sinopulmonary infection, alpha 1-antitrypsin deficiency, primary immunodeficiency, acquired immune deficiency syndrome, opportunistic infection, an infectious state, a post infectious state, common cold, exercise induced hypersecretion of mucus, inflammatory bowel disease, ulcerative colitis, Crohn's disease, respiratory infection, respiratory obstruction, inhalation or aspiration of a toxic gas, pulmonary aspiration, or alcoholism in subjects with elevated levels of mucus in their respiratory tract or who are at risk of having increased levels of mucus in their respiratory tract.

Fusion Proteins

Sialidase catalytic domain proteins can be fusion proteins, in which the fusion protein comprises at least one sialidase catalytic domain and at least one other protein domain, including but not limited to: a purification domain, a protein tag, a protein stability domain, a solubility domain, a protein size-increasing domain, a protein folding domain, a protein localization domain, an anchoring domain, an N-terminal domain, a C-terminal domain, a catalytic activity domain, a binding domain, or a catalytic activity-enhancing domain. The at least one other protein domain can be derived from another source, such as, but not limited to, sequences from another protein. The at least one other protein domain need not be based on any known protein sequence, but can be engineered and empirically tested to perform any function in the fusion protein.

Purification domains can include, as nonlimiting examples, one or more of a his tag, a calmodulin binding domain, a maltose binding protein domain, a streptavidin domain, a streptavidin binding domain, an intein domain, or a chitin binding domain. Protein tags can comprise sequences that can be used for antibody detection of proteins, such as, for example, the myc tag, the hemagglutinin tag, or the FLAG tag. Protein domains that enhance protein expression, modification, folding, stability, size, or localization can be based on sequences of know proteins or engineered. Other protein domains can have binding or catalytic activity or enhance the catalytic activity of the sialidase catalytic domain.

Fusion proteins used in the compositions, compounds and methods of the present invention comprise at least one sialidase catalytic domain and at least one anchoring domain. In some embodiments, anchoring domains include GAG-binding domains, such as the GAG-binding domain or human amphiregulin (SEQ ID NO:7).

Sialidase catalytic domains and other domains of a fusion protein used in the present invention can optionally be joined by linkers, such as but not limited to peptide linkers. A variety of peptide linkers are known in the art. In one embodiment a linker can be a peptide linker comprising glycine, such as G-G-G-G-S (SEQ ID NO:10).

Such fusion proteins can be formulated for nasal, tracheal, bronchial, oral, or topical administration, or can be formulated as an injectable solution or as eyedrops or formulated into a solution or dry powder and inhaled with an inhaler. These fusion proteins can be formulated into pharmaceutical compositions that include various additional compounds either alone or in various combinations, such as, $Na_2SO_4$, $MgSO_4$, $CaCl_2$, Histidine, Histine-HCl, and Trehalose or their analogs. These additional compounds can be included in the pharmaceutical compositions to act as excipients or as active ingredients that provide additional beneficial effects.

Such fusion proteins or pharmaceutical compositions containing them can be used (a) to treat or prevent allergic and inflammatory responses in the respiratory tract, (b) to reduce the quantity of mucus in the respiratory tract of subjects with elevated levels of mucus in their respiratory tracts, (c) to limit increases in the quantity of mucus in the respiratory tract of subjects above a baseline of mucus in their respiratory tracts, and/or (d) to prevent, treat, or ameliorate the effects of chronic obstructive pulmonary disease (COPD), bronchitis, bronchiectasis, cystic fibrosis (CF), vasculitis, mucus plugging, Wegener's granulomatosis, pneumonia, tuberculosis, cancer involving the lungs or the respiratory tract, Kartagener syndrome, Young's syndrome, chronic sinopulmonary infection, alpha 1-antitrypsin deficiency, primary immunodeficiency, acquired immune deficiency syndrome, opportunistic infection, an infectious state, a post infectious state, common cold, exercise induced hypersecretion of mucus, inflammatory bowel disease, ulcerative colitis, Crohn's disease, respiratory infection, respiratory obstruction, inhalation or aspiration of a toxic gas, pulmonary aspiration, or alcoholism in subjects with elevated levels of mucus in their respiratory tract or who are at risk of having increased levels of mucus in their respiratory tract.

Various constructs of fusion proteins are shown in FIGS. 4-6, as well as in the sequences provided in the sequence listing provided herein.

Methods for Testing the Compounds and Compositions and/or for Screening to Identify Sialidases and/or Active Portions Thereof to Treat Diseases Acc The compounds and compositions provided herein can be tested for their activity in reducing inflammation, allergies or associated responses, such as mucus overproduction, using standard assays known to those of skill in the art. Several cell-based (e.g., tracheal cell cultures) and animal-based assays (mouse models, guinea pig models) for measuring inflammation or mucus overproduction are known (see, e.g., Nakao et al., *J. Immunol.*, 180:6262-6269 (2008); Westerhof et al., *Mediators Inflamm.*, 10(3):143-154 (2001); Miller et al., *J. Immunol.*, 170:3348-3356 (2003); Nakanishi et al., *Proc. Natl. Acad. Sci. USA*, 98(9):5175-5180 (2001); and DuBuske, *Allergy Proc.*, 16(2):55-58 (1995), the contents of each of which are incorporated in their entirety by reference herein). The compounds and compositions provided herein can be tested for their ability to reduce inflammation or mucus overproduction in any of these assays or other standard assays known to those of skill in the art. In addition, sialidases or active portions thereof can be identified and/or selected for their anti-inflammatory activity and/or ability to reduce associated responses, such as mucus overproduction, using such assays. Exemplary assays and protocols are described herein in Example 1 and Example 2.

In addition to assays that measure inflammation or associated responses, such as mucus overproduction, the compounds and compositions provided herein can be tested for their activity by assessing their ability to disrupt muscarinic receptor-mediated signaling in the presence of an agonist. Muscarinic receptors, or mAChRs, are G protein-coupled acetylcholine receptors found in the plasma membranes of certain neurons and other cells. They play several roles, including acting as the main end-receptor stimulated by acetylcholine released from postganglionic fibers in the parasympathetic nervous system.

Muscarinic receptor-agonist interactions, and the resulting signaling, is believed to play a role in diseases that have associated inflammatory and/or allergic responses, such as asthma and COPD (see, e.g., "Muscarinic Receptors in Airways Diseases," Birkhauser-Verlag publ., Zangsma et al., Eds.).

More specifically, acetylcholinergic mechanisms are recognized to influence the following normal and pathogenic respiratory functions:
1. secretion of mucus,
2. active transport of ions across the respiratory epithelium and during mucociliary transport,
3. smooth muscle tone of the airways,
4. immunologic and inflammatory response of the airways,
5. reflex regulation of the airways,
6. respiratory responses of the airways in asthma and in other hypersensitivity states of the respiratory tract.

Consequently, certain anti-muscarinic agents have been effective against: (a) acetylcholinergically induced bronchoconstriction; (b) iatrogenic airway spasms induced by beta blockers; and (c) psychogenic bronchospasm. The two main pulmonary applications of anti-muscarinic agents has been chronic bronchitis and bronchial asthma (*Pharmacology of Anti-Muscarinic Agents*, Laszlo Gyermek (1998)).

There are five broad classes of muscarinic receptors, based on their physiological roles, and agonists for each of these receptors are known to those of skill in the art:
M1 receptor—exemplary agonists include acetylcholine, oxotremorine, muscarine, carbachol and McNA343
M2 receptor—exemplary agonists include acetylcholine, methacholine, carbachol, oxotremorine and muscarine
M3 receptor—exemplary agonists include acetylcholine, bethanechol, carbachol, oxotremorine and pilocarpine
M4 receptor—exemplary agonists include acetylcholine, carbachol and oxotremorine
M5 receptor—exemplary agonists include acetylcholine, carbachol and oxotremorine In some embodiments, the compounds and compositions provided herein can be tested for the ability to reduce inflammation and/or allergic responses, including mucus overproduction, associated with RTIs or RTDs by assessing their ability to disrupt muscarinic receptor-agonist interactions. Further, sialidases and/or active portions thereof can be screened, identified and selected for their ability to reduce inflammation, allergies, and/or associated responses such as mucus overproduction by assessing their ability to disrupt muscarinic receptor-agonist interactions. These tests and screens can be performed using standard assays known to those of skill in the art (see, e.g, Armstrong et al., *Curr. Protocols in Pharmacol.*, UNIT 12-13 (2010), the contents of which are incorporated in their entirety by reference herein). An exemplary assay and protocol is provided herein in Example 3.

Pharmaceutical Compositions

The present invention includes compounds of the present invention formulated as pharmaceutical compositions. The pharmaceutical compositions comprise a pharmaceutically acceptable carrier prepared for storage and subsequent administration, which have a pharmaceutically effective amount of the compound in a pharmaceutically acceptable carrier or diluent. Acceptable carriers or diluents for therapeutic use are well known in the pharmaceutical art, and are described, for example, in Remington's Pharmaceutical Sciences, 18th Ed., Mack Publishing Co., Easton, Pa. (1990)). Preservatives, stabilizers, dyes and even flavoring agents can be provided in the pharmaceutical composition. For example, sodium benzoate, sorbic acid and esters of p-hydroxybenzoic acid can be added as preservatives. In addition, antioxidants and suspending agents can be used.

Depending on the target cell, the compounds of the present invention can be formulated and used as tablets, capsules or elixirs for oral or inhaled administration; salves or ointments for topical application; suppositories for rectal administration; sterile solutions, suspensions, and encapsulated powders and the like for use as inhalants or nasal sprays. Injectables can also be prepared in conventional forms either as liquid solutions or suspensions, solid forms suitable for solution or suspension in liquid prior to injection, or as emulsions.

Suitable excipients are, for example, water, saline, dextrose, mannitol, lactose, lecithin, albumin, sodium glutamate, cysteine hydrochloride and the like. In addition to those excipients, additional compounds that can be included in the pharmaceutical compositions described herein either alone or in various combinations include $Na_2SO_4$, $MgSO_4$, $CaCl_2$, Histidine, Histine-HCl, and Trehalose or their analogs or Mg salts and/or Ca salts. These additional compounds can be included in the pharmaceutical compositions to act as excipients or as active ingredients that provide additional beneficial effects. In addition, if desired, the injectable pharmaceutical compositions can contain minor amounts of nontoxic auxiliary substances, such as wetting agents, pH buffering agents and the like.

The pharmaceutically effective amount of a test compound required as a dose will depend on the route of administration, the type of animal or patient being treated, and the physical characteristics of the specific animal under consideration. The dose can be tailored to achieve a desired effect, such as reduction of elevated levels of mucus in the respiratory tract, but will depend on such factors as weight, diet, concurrent medication and other factors which those skilled in the medical arts will recognize. In practicing the methods of the present invention, the pharmaceutical compositions can be used alone or in combination with one another, or in combination with other therapeutic or diagnostic agents. These products can be utilized in vivo in a non-human animal subject, in a mammalian subject, in a human subject, or in vitro. In employing them in vivo, the pharmaceutical compositions can be administered to the patient or subject in a variety of ways, including topically, parenterally, intravenously, subcutaneously, intramuscularly, colonically, rectally, nasally or intraperitoneally, employing a variety of dosage forms. Such methods can also be used in testing the activity of test compounds in vivo.

In some embodiments, these pharmaceutical compositions may be in the form of orally-administrable suspensions, solutions, tablets or lozenges; nasal sprays; inhalants; injectables, topical sprays, ointments, powders, or gels, or formulated into a solutions or dry powders and inhaled with an inhaler.

When administered orally as a suspension, compositions of the present invention are prepared according to techniques well-known in the art of pharmaceutical formulation and may contain microcrystalline cellulose for imparting bulk, alginic acid or sodium alginate as a suspending agent, methylcellulose as a viscosity enhancer, and sweeteners/flavoring agents known in the art. As immediate release tablets, these compositions may contain microcrystalline cellulose, dicalcium phosphate, starch, magnesium stearate and lactose and/or other excipients, binders, extenders, disintegrants, diluents and lubricants known in the art. Components in the formulation of a mouthwash or rinse include antimicrobials, surfactants, cosurfactants, oils, water and other additives such as sweeteners/flavoring agents known in the art.

When administered by a drinking solution, the composition comprises one or more of the compounds of the present invention, dissolved in water, with appropriate pH adjustment, and with carrier. The compound can be dissolved in distilled water, tap water, spring water, and the like. The pH can in some embodiments be adjusted to between about 3.5 and about 8.5. Sweeteners can be added, e.g., 1% (w/v) sucrose.

Lozenges can be prepared according to U.S. Pat. No. 3,439,089, herein incorporated by reference for these purposes.

When administered by nasal aerosol or inhalation, the pharmaceutical compositions are prepared according to techniques well-known in the art of pharmaceutical formulation and can be prepared as solutions in saline, employing benzyl alcohol or other suitable preservatives, absorption promoters to enhance bioavailability, fluorocarbons, and/or other solubilizing or dispersing agents known in the art. See, for example, Ansel, H. C. et al., Pharmaceutical Dosage Forms and Drug Delivery Systems, Sixth Ed. (1995). Inhaled powders can also be prepared using techniques described in U.S. patent application Ser. Nos. 11/657,813 and 12/179,520, both of which are incorporated herein by reference in their entirety. These compositions and formulations can generally be prepared with suitable nontoxic pharmaceutically acceptable ingredients. These ingredients are known to those skilled in the preparation of nasal dosage forms and some of these can be found in Remington's Pharmaceutical Sciences, 18th Ed., Mack Publishing Co., Easton, Pa. (1990, a standard reference in the field. The choice of suitable carriers is highly dependent upon the exact nature of the nasal dosage form desired, e.g., solutions, suspensions, ointments, or gels. Nasal dosage forms generally contain large amounts of water in addition to the active ingredient. Minor amounts of other ingredients such as pH adjusters, emulsifiers or dispersing agents, preservatives, surfactants, jelling agents, or buffering and other stabilizing and solubilizing agents can also be present. Generally, the nasal dosage form can be isotonic with nasal secretions.

Nasal formulations can be administers as drops, sprays, aerosols or by any other intranasal dosage form. Optionally, the delivery system can be a unit dose delivery system. The volume of solution or suspension delivered per dose can be anywhere from about 5 to about 2000 microliters, from about 10 to about 1000 microliters, or from about 50 to about 500 microliters. Delivery systems for these various dosage forms can be dropper bottles, plastic squeeze units, atomizers, nebulizers or pharmaceutical aerosols in either unit dose or multiple dose packages.

The formulations of this invention can be varied to include; (1) other acids and bases to adjust the pH; (2) other tonicity imparting agents such as sorbitol, glycerin and dextrose; (3) other antimicrobial preservatives such as other parahydroxy benzoic acid esters, sorbate, benzoate, propionate, chlorbutanol, phenylethyl alcohol, benzalkonium chloride, and mercurials; (4) other viscosity imparting agents such as sodium carboxymethylcellulose, microcrystalline cellulose, polyvinylpyrrolidone, polyvinyl alcohol and other gums; (5) suitable absorption enhancers; (6) stabilizing agents such as antioxidants, like bisulfite and ascorbate, metal chelating agents such as sodium edetate and drug solubility enhancers such as polyethylene glycols.

One embodiment of the invention includes pharmaceutical compositions that at various dosage levels, such as dosage levels between about 0.01 mg and about 100 mg, reduce the quantity of mucus in the respiratory tract of subjects with elevated levels of mucus in their respiratory tracts, and/or that limit increases in the quantity of mucus in the respiratory tract of subjects above a baseline of mucus in their respiratory tracts. Examples of such dosage levels include doses of about 0.05 mg, 0.06 mg, 0.1 mg, 0.5 mg, 1 mg, 5 mg, 10 mg, 20 mg, 50 mg, or 100 mg. Another embodiment of the invention includes pharmaceutical compositions that at various dosage levels, such as dosage levels between about 0.01 mg and about 100 mg, reduce inflammation in the respiratory tract or prevent worsening of inflammation in the respiratory tract. Examples of such dosage levels include doses of about 0.05 mg, 0.06 mg, 0.1 mg, 0.5 mg, 1 mg, 5 mg, 10 mg, 20 mg, 50 mg, or 100 mg. The foregoing doses can be administered one or more times per day, for one day, two days, three days, four days, five days, six days, seven days, eight days, nine days, ten days, eleven days, twelve days, thirteen days, or fourteen or more days. Higher doses or lower doses can also be administered. Typically, dosages can be between about 1 ng/kg and about 10 mg/kg, between about 10 ng/kg and about 1 mg/kg, and between about 100 ng/kg and about 100 micrograms/kg. In various examples described herein, mice were treated with various dosages of the compositions described herein, including dosages of 0.0008 mg/kg, 0.004 mg/kg, 0.02 mg/kg, 0.06 mg/kg, 0.1 mg/kg, 0.3 mg/kg, 0.6 mg/kg, and 1.0 gm/kg.

In one embodiment a pharmaceutical composition includes DAS181, $MgSO_4$ 1.446 mg/ml, $CaCl_2$ 0.059 mg/ml, Histidine 1.427 mg/ml, Histidine-HCl 1.943 mg/ml, and Trehalose 3.000 mg/ml.

In another embodiment a pharameutical composition includes DAS181, $MgSO_4$, $CaCl_2$, Histidine, Histidine-HCl, and Trehalose.

In another embodiment a pharameutical composition includes DAS181, $Na_2SO_4$, and $CaCl_2$.

In another embodiment a pharmaceutical composition includes DAS181 and any combination of one or more of the following: $Na_2SO_4$, $MgSO_4$, $CaCl_2$, Histidine, Histidine-HCl, and Trehalose.

In another embodiment a pharmaceutical composition includes (a) a naturally occurring sialidase protein or peptide or an active portion thereof, or a recombinant protein substantially homologous to at least a portion of a naturally occurring sialidase, (b) $MgSO_4$ 1.446 mg/ml, (c) $CaCl_2$ 0.059 mg/ml, (d) Histidine 1.427 mg/ml, (e) Histidine-HCl 1.943 mg/ml, and (f) Trehalose 3.000 mg/ml. In one embodiment, the protein or peptide is a sialidase with substantial homology to the *A. viscosus* sialidase (SEQ ID NO:12) or substantial homology to an active portion thereof, such as amino acids 274-666, 274-667, 270-667, 274-681, or 290-681 of SEQ ID NO:12, or any other catalytic domain of *Actinomyces viscosis* sialidase. In other embodiments, the protein or peptide is from one of the large bacterial sialidases that can degrade the receptor sialic acids Neu5Ac alpha(2,6)-Gal and Neu5Ac alpha(2,3)-Gal. For example, the bacterial sialidase enzymes from *Clostridium perfringens* (Genbank Accession Number X87369), *Arthrobacter ureafaciens*, or *Micromonospora viridifaciens* (Genbank Accession Number D01045) or proteins or peptides that are substantially homologous to those sialidases or their active portions. In other embodiments, the protein or peptide is from other sialidases, such as those encoded by the genes NEU2 (SEQ ID NO:8; Genbank Accession Number Y16535; Monti, E, Preti, Rossi, E., Ballabio, A and Borsani G. (1999) *Genomics* 57:137-143) and NEU4 (SEQ ID NO:9; Genbank Accession Number NM080741; Monti, E, Preti, A, Venerando, B. and Borsani, G. (2002) *Neurochem Res* 27:646-663) (FIG. 2), or active portions of those sialidases.

In another embodiment a pharmaceutical composition includes (a) a naturally occurring sialidase protein or peptide or an active portion thereof, or a recombinant protein substantially homologous to at least a portion of a naturally occurring sialidase, (b) $MgSO_4$, (c) $CaCl_2$, (d) Histidine, (e) Histidine-HCl, and (f) Trehalose. In one embodiment, the protein or peptide is a sialidase with substantial homology to the *A. viscosus* sialidase (SEQ ID NO:12) or substantial homology to an active portion thereof, such as amino acids 274-666, 274-667, 270-667, 274-681, or 290-681 of SEQ ID NO:12, or any other catalytic domain of *Actinomyces viscosis* sialidase. In other embodiments, the protein or peptide is from one of the large bacterial sialidases that can degrade the receptor sialic acids Neu5Ac alpha(2,6)-Gal and Neu5Ac alpha(2,3)-Gal. For example, the bacterial sialidase enzymes from *Clostridium perfringens* (Genbank Accession Number X87369), *Arthrobacter ureafaciens*, or *Micromonospora viridifaciens* (Genbank Accession Number D01045) or proteins or peptides that are substantially homologous to those sialidases or their active portions. In other embodiments, the protein or peptide is from other sialidases, such as those encoded by the genes NEU2 (SEQ ID NO:8; Genbank Accession Number Y16535; Monti, E, Preti, Rossi, E., Ballabio, A and Borsani G. (1999) *Genomics* 57:137-143) and NEU4 (SEQ ID NO:9; Genbank Accession Number NM080741; Monti, E, Preti, A, Venerando, B. and Borsani, G. (2002) *Neurochem Res* 27:646-663) (FIG. 2), or active portions of those sialidases.

In another embodiment a pharmaceutical composition includes (a) a naturally occurring sialidase protein or peptide or an active portion thereof, or a recombinant protein substantially homologous to at least a portion of a naturally occurring sialidase, (b) $Na_2SO_4$, and (c) $CaCl_2$. In one embodiment, the protein or peptide is a sialidase with substantial homology to the *A. viscosus* sialidase (SEQ ID NO:12) or substantial homology to an active portion thereof, such as amino acids 274-666, 274-667, 270-667, 274-681, or 290-681 of SEQ ID NO:12, or any other catalytic domain of *Actinomyces viscosis* sialidase. In one embodiment, the protein or peptide is a sialidase with substantial homology to the *A. viscosus* sialidase (SEQ ID NO:12) or substantial homology to an active portion thereof, such as amino acids 274-666, 274-667, 270-667, 274-681, or 290-681 of SEQ ID NO:12, or any other catalytic domain of *Actinomyces viscosis* sialidase. In other embodiments, the protein or peptide is from one of the large bacterial sialidases that can degrade the receptor sialic acids Neu5Ac alpha(2,6)-Gal and Neu5Ac alpha(2,3)-Gal. For example, the bacterial sialidase enzymes from *Clostridium perfringens* (Genbank Accession Number X87369), *Arthrobacter ureafaciens*, or *Micromonospora viridifaciens* (Genbank Accession Number D01045) or proteins or peptides that are substantially homologous to those sialidases or their active portions. In other embodiments, the protein or peptide is from other sialidases, such as those encoded by the genes NEU2 (SEQ ID NO:8; Genbank Accession Number Y16535; Monti, E, Preti, Rossi, E., Ballabio, A and Borsani G. (1999) *Genomics* 57:137-143) and NEU4 (SEQ ID NO:9; Genbank Accession Number NM080741; Monti, E, Preti, A, Venerando, B. and Borsani, G. (2002) *Neurochem Res* 27:646-663) (FIG. 2), or active portions of those sialidases.

In another embodiment a pharmaceutical composition includes (a) a naturally occurring sialidase protein or peptide or an active portion thereof, or a recombinant protein substantially homologous to at least a portion of a naturally occurring sialidase, and any combination of one or more of the following: $Na_2SO_4$, $MgSO_4$, $CaCl_2$, Histidine, Histidine-HCl, and Trehalose. In one embodiment, the protein or peptide is a sialidase with substantial homology to the *A. viscosus* sialidase (SEQ ID NO:12) or substantial homology to an active portion thereof, such as amino acids 274-666, 274-667, 270-667, 274-681, or 290-681 of SEQ ID NO:12, or any other catalytic domain of *Actinomyces viscosis* sialidase. In other embodiments, the protein or peptide is from one of the large bacterial sialidases that can degrade the receptor sialic acids Neu5Ac alpha(2,6)-Gal and Neu5Ac alpha(2,3)-Gal. For example, the bacterial sialidase enzymes from *Clostridium perfringens* (Genbank Accession Number X87369), *Arthrobacter ureafaciens*, or *Micromonospora viridifaciens* (Genbank Accession Number D01045) or proteins or peptides that are substantially homologous to those sialidases or their active portions. In other embodiments, the protein or peptide is from other sialidases, such as those encoded by the genes NEU2 (SEQ ID NO:8; Genbank Accession Number Y16535; Monti, E, Preti, Rossi, E., Ballabio, A and Borsani G. (1999) *Genomics* 57:137-143) and NEU4 (SEQ ID NO:9; Genbank Accession Number NM080741; Monti, E, Preti, A, Venerando, B. and Borsani, G. (2002) *Neurochem Res* 27:646-663) (FIG. 2), or active portions of those sialidases.

In another embodiment a pharmaceutical composition includes (a) a fusion protein that has at least one catalytic domain of a sialidase, wherein the catalytic domain of the sialidase includes the sequence of amino acids extending from amino acid 274 to amino acid 666 of SEQ ID NO:12 (alternatively, 274 to 666, 270-667, 274-681, 290-681 of SEQ ID NO:12, or any other catalytic domain of *Actinomyces viscosis*), inclusive, and at least one anchoring domain, wherein the anchoring domain is a glycosaminoglycan (GAG) binding domain of human amphiregulin including the amino acid sequence of SEQ ID NO:7, (b) $MgSO_4$ 1.446 mg/ml, (c) $CaCl_2$ 0.059 mg/ml, (d) Histidine 1.427 mg/ml, (e) Histidine-HCl 1.943 mg/ml, and (f) Trehalose 3.000 mg/ml.

In another embodiment a pharmaceutical composition includes (a) a fusion protein that has at least one catalytic domain of a sialidase, wherein the catalytic domain of the sialidase includes the sequence of amino acids extending from amino acid 274 to amino acid 666 of SEQ ID NO:12 (alternatively, 274 to 666, 270-667, 274-681, 290-681 of SEQ ID NO:12, or any other catalytic domain of *Actinomyces viscosis*), inclusive, and at least one anchoring domain, wherein the anchoring domain is a glycosaminoglycan (GAG) binding domain of human amphiregulin including the amino acid sequence of SEQ ID NO:7, (b) $MgSO_4$, (c) $CaCl_2$, (d) Histidine, (e) Histidine-HCl, and (f) Trehalose.

In another embodiment a pharmaceutical composition includes (a) a fusion protein that has at least one catalytic domain of a sialidase, wherein the catalytic domain of the sialidase includes the sequence of amino acids extending from amino acid 274 to amino acid 666 of SEQ ID NO:12 (alternatively, 274 to 666, 270-667, 274-681, 290-681 of SEQ ID NO:12, or any other catalytic domain of *Actinomyces viscosis*), inclusive, and at least one anchoring domain, wherein the anchoring domain is a glycosaminoglycan (GAG) binding domain of human amphiregulin including the amino acid sequence of SEQ ID NO:7, (b) $Na_2SO_4$, and (c) $CaCl_2$.

In another embodiment a pharmaceutical composition includes (a) a fusion protein that has at least one catalytic domain of a sialidase, wherein the catalytic domain of the sialidase includes the sequence of amino acids extending from amino acid 274 to amino acid 666 of SEQ ID NO:12 (alternatively, 274 to 666, 270-667, 274-681, 290-681 of SEQ ID NO:12, or any other catalytic domain of *Actinomyces viscosis*), inclusive, and at least one anchoring domain, wherein the anchoring domain is a glycosaminoglycan (GAG) binding domain of human amphiregulin including the amino acid sequence of SEQ ID NO:7, and (b) any combination of one or more of the following: $Na_2SO_4$, $MgSO_4$, $CaCl_2$, Histidine, Histidine-HCl, and Trehalose.

In another embodiment a pharmaceutical composition includes (a) a fusion protein having a sialidase or an active portion thereof and an anchoring domain, (b) $MgSO_4$ 1.446 mg/ml, (c) $CaCl_2$ 0.059 mg/ml, (d) Histidine 1.427 mg/ml, (e) Histidine-HCl 1.943 mg/ml, and (f) Trehalose 3.000 mg/ml.

In another embodiment a pharmaceutical composition includes (a) a fusion protein having a sialidase or an active portion thereof and an anchoring domain, (b) $MgSO_4$, (c) $CaCl_2$, (d) Histidine, (e) Histidine-HCl, and (f) Trehalose.

In another embodiment a pharmaceutical composition includes (a) a fusion protein having a sialidase or an active portion thereof and an anchoring domain, (b) $Na_4SO_4$, and (c) $CaCl_2$.

In another embodiment a pharmaceutical composition includes (a) a fusion protein having a sialidase or an active portion thereof and an anchoring domain, and (b) any combination of one or more of the following: $Na_2SO_4$, $MgSO_4$, $CaCl_2$, Histidine, Histidine-HCl, and Trehalose.

Another representative example of a pharmaceutical composition of the present invention and that can be used in the methods described herein includes the following: DAS181, histidine, magnesium sulfate (or citrate salt), calcium chloride, trehalose, water, Na-Acetate, and acetic acid.

Yet another representative example of a pharmaceutical composition of the present invention and that can be used in the methods described herein includes DAS181 (in any concentration between about 0.01% and about 100% w/w, between about 1.00% and about 90.0% w/w, between about 5.00% and about 80.0% w/w, between about 10.0% and about 70.0% w/w, between about 20.0% and about 70% w/w, between about 30.0% and about 70.0% w/w, between about 40.0% and about 70.0% w/w, between about 50.0% and about 70% w/w, between about 60.0% and about 70.0% w/w) in combination with any of the following: histidine or histidine-HCl (in any concentration between about 0.00% and about 90.0% w/w, between about 0.01% and about 80.0% w/w, between about 1.00% and about 75.0% w/w, between about 2.00% and about 70.0% w/w, between about 3.00% and about 60% w/w, between about 4.00% and about 50.0% w/w, between about 5.00% and about 40.0% w/w, between about 6.00% and about 30% w/w, between about 7.00% and about 20.0% w/w), magnesium sulfate (or citrate salt or sodium sulfate) (in any concentration between about 0.00% and about 90.0% w/w, between about 0.01% and about 80.0% w/w, between about 1.00% and about 75.0% w/w, between about 2.00% and about 70.0% w/w, between about 3.00% and about 60% w/w, between about 4.00% and about 50.0% w/w, between about 5.00% and about 40.0% w/w, between about 6.00% and about 30% w/w, between about 7.00% and about 20.0% w/w), calcium chloride (in any concentration between about 0.00% and about 90.0% w/w, between about 0.01% and about 80.0% w/w, between about 0.01% and about 75.0% w/w, between about 0.01% and about 70.0% w/w, between about 0.01% and about 60% w/w, between about 0.01% and about 50.0% w/w, between about 0.01% and about 40.0% w/w, between about 0.01% and about 30% w/w, between about 0.10% and about 20.0% w/w), trehalose (in any concentration between about 0.00% and about 90.0% w/w, between about 0.01% and about 80.0% w/w, between about 1.00% and about 75.0% w/w, between about 2.00% and about 70.0% w/w, between about 3.00% and about 60% w/w, between about 4.00% and about 50.0% w/w, between about 5.00% and about 40.0% w/w, between about 6.00% and about 30% w/w, between about 7.00% and about 20.0% w/w), water (in any concentration between about 0.00% and about 90.0% w/w, between about 0.01% and about 80.0% w/w, between about 1.00% and about 75.0% w/w, between about 2.00% and about 70.0% w/w, between about 3.00% and about 60% w/w, between about 4.00% and about 50.0% w/w, between about 5.00% and about 40.0% w/w, between about 6.00% and about 30% w/w, between about 7.00% and about 20.0% w/w), Na-Acetate (in any concentration between about 0.00% and about 90.0% w/w, between about 0.01% and about 80.0% w/w, between about 0.01% and about 75.0% w/w, between about 0.01% and about 70.0% w/w, between about 0.01% and about 60% w/w, between about 0.01% and about 50.0% w/w, between about 0.01% and about 40.0% w/w, between about 0.01% and about 30% w/w, between about 0.10% and about 20.0% w/w), and acetic acid (in any concentration between about 0.00% and about 90.0% w/w, between about 0.01% and about 80.0% w/w, between about 0.01% and about 75.0% w/w, between about 0.01% and about 70.0% w/w, between about 0.01% and about 60% w/w, between about 0.01% and about 50.0% w/w, between about 0.01% and about 40.0% w/w, between about 0.01% and about 30% w/w, between about 0.10% and about 20.0% w/w).

Any of the above pharmaceutical compositions may in addition include $MgCl_2$ in various concentrations ranging from about 0% to about 75% w/w.

Reducing Mucus in the Respiratory Tract and Limiting its Increase

Accumulation or elevated levels of mucus in the respiratory airway tree can be caused by an increased volume of mucus produced, and also by decreased clearance due to defects in the ciliary clearance apparatus in the respiratory tract. Hypersecretion of mucus can be chronic, but increased volumes are produced in exacerbations of COPD, during attacks of asthma, and in bronchiectatic and cystic fibrosis patients (W. D. Kim, Eur Respir. J. 1997, 10:1914-1917). Intraluminal mucus accumulation (i.e., elevated levels of mucus) in the airways associated with hypersecretion of mucus or decreased clearance thereof creates a clinical problem in almost all pulmonary diseases and diseases that have an affect on the respiratory tract, including without limitation chronic obstructive pulmonary disease (COPD), bronchitis, bronchiectasis, cystic fibrosis (CF), vasculitis, mucus plugging, Wegener's granulomatosis, pneumonia, tuberculosis, cancer involving the lungs or the respiratory tract, Kartagener syndrome, Young's syndrome, chronic sinopulmonary infection, alpha 1-antitrypsin deficiency, primary immunodeficiency, acquired immune deficiency syndrome, opportunistic infection, an infectious state, a post infectious state, common cold, exercise induced hypersecretion of mucus, inflammatory bowel disease, ulcerative colitis, Crohn's disease, respiratory infection, respiratory obstruction, inhalation or aspiration of a toxic gas, pulmonary aspiration, or alcoholism. Elevated levels of mucus in the respiratory tract are an important determinant in the prognosis and clinical feastures of various pulmonary diseases, such as chronic bronchitis, bronchiectasis and bronchial asthma, in addition to cystic fibrosis and COPD (W. D. Kim, Eur Respir. J. 1997, 10:1914-1917). Accordingly, in some embodiments, the present disclosure include methods in which a subject with one or more of these conditions or diseases is selected for treatment. In some embodiments, the methods can include selecting a subject with one or more of the conditions or diseases provided herein and that is not infected with one or more of influenza, parainfluenza, and/or respiratory syncytial virus (RSV). Following selection, the subject can be treated by administration of one or more of the compositions disclosed herein.

Provided herein are methods that include the administration of the compounds described herein and in U.S. application Ser. Nos. 10/718,986 and 10/939,262, or compositions containing them, to reduce the quantity of mucus in the respiratory tract of subjects with elevated levels of mucus in their respiratory tracts and to limit increases in the quantity of mucus in the respiratory tract of subjects above a baseline of mucus in their respiratory tracts. Thus, the invention relates to method of using the therapeutic compounds and/or compositions described herein to prevent or treat diseases that are caused by, cause, or are exacerbated by respiratory inflammation or increased mucus production, such as, both allergic and non-allergic asthma, chronic obstructive pulmonary disease (COPD), bronchitis (both acute and non-acute), bronchiectasis, cystic fibrosis (CF), vasculitis, mucuous plugging, Wegener's granulomatosis, and any other disorder that causes inflammation or increased mucus production in the respiratory tract or is caused by or exacerbated by inflammation or increased mucus production in the respiratory tract. The invention also includes methods of using the therapeutic compounds and/or compositions described herein to reduce the quantity of mucus in the respiratory tract of subjects with elevated levels of mucus in their respiratory tracts and limit increases in the quantity of mucus in the respiratory tract of subjects above a baseline of mucus in their respiratory tracts.

In some embodiments, the methods include administering a composition or compound containing a therapeutically effective amount of a protein or peptide having a sialidase or an active portion thereof to a subject. The protein or peptide can be an isolated naturally occurring sialidase protein, or a recombinant protein substantially homologous to at least a portion of a naturally occurring sialidase. In one embodiment, a pharmaceutical composition or compound contains a sialidase with substantial homology to the A. viscosus sialidase (SEQ ID NO:12) or substantial homology to an active portion thereof, such as amino acids 274-666, 274-667, 270-667, 274-681, or 290-681 of SEQ ID NO:12, or any other catalytic domain of Actinomyces viscosis sialidase. The therapeutically effective amount includes an amount of the protein or peptide that results in a reduction of the quantity of mucus in the respiratory tract after administration of the composition or compound when compared to the quantity of mucus present prior to administration of the composition.

In other embodiments, the methods include administering a composition or compound containing a therapeutically effective amount of a fusion protein, wherein the fusion protein has at least one catalytic domain of a sialidase, wherein the catalytic domain of the sialidase includes the sequence of amino acids extending from amino acid 274 to amino acid 666 of SEQ ID NO:12 (alternatively, 274 to 666, 270-667, 274-681, 290-681 of SEQ ID NO:12, or any other catalytic domain of Actinomyces viscosis), inclusive, and at least one anchoring domain, wherein the anchoring domain is a glycosaminoglycan (GAG) binding domain of human amphiregulin including the amino acid sequence of SEQ ID NO:7. The therapeutically effective amount includes an amount of the fusion protein that results in a reduction of the quanitity of mucus in the respiratory tract after administration of the composition or compound when compared to the quantity of mucus present prior to administration of the composition.

In yet other embodiments, the methods include administering a composition containing a therapeutically effective amount of a fusion protein having a sialidase or an active portion thereof and an anchoring domain. The therapeutically effective amount includes an amount of the fusion protein that results in a reduction of the quanitity of mucus in the respiratory tract after administration of the composition or compound when compared to the quantity of mucus present prior to administration of the composition.

Other embodiments include methods of preventing, treating or ameliorating the effects of chronic obstructive pulmonary disease (COPD), bronchitis, bronchiectasis, cystic fibrosis (CF), vasculitis, mucus plugging, Wegener's granulomatosis, pneumonia, tuberculosis, cancer involving the lungs or the respiratory tract, Kartagener syndrome, Young's syndrome, chronic sinopulmonary infection, alpha 1-antitrypsin deficiency, primary immunodeficiency, acquired immune deficiency syndrome, opportunistic infection, an infectious state, a post infectious state, common cold, exercise induced hypersecretion of mucus, inflammatory bowel disease, ulcerative colitis, Crohn's disease, respiratory infection, respiratory obstruction, inhalation or aspiration of a toxic gas, pulmonary aspiration, or alcoholism in a subject with an elevated level of mucus in his or her respiratory tract. The methods include administering (a) a composition containing a therapeutically effective amount of a protein or peptide having a sialidase or an active portion thereof to a subject, (b) a composition containing a therapeutically effective amount of a fusion protein, wherein the fusion protein has at least one catalytic domain of a sialidase, wherein the catalytic domain of the sialidase includes the sequence of amino acids extending from amino acid 274 to amino acid 666 of SEQ ID NO:12 (alternatively, 274 to 666, 270-667, 274-681, 290-681 of SEQ ID NO:12, or any other catalytic domain of Actinomyces viscosis), inclusive, and at least one anchoring domain, wherein the anchoring domain is a glycosaminoglycan (GAG) binding domain of human amphiregulin including the amino acid sequence of SEQ ID NO:7, or (c) a composition or compound containing a therapeutically effective amount of a fusion protein having a sialidase or an active portion thereof and an anchoring domain. The therapeutically effective amount of these compositions or compounds includes an amount that results in a reduction of the quanitity of mucus in the respiratory tract after administration of the composition when compared to the quantity of mucus present prior to administration of the composition or compound.

Yet other embodiments include methods of limiting an increase in the quantity of mucus in the respiratory tract of a subject above a baseline level of mucus in said subject's respiratory tract. The methods include administering (a) a composition or compound containing a therapeutically effective amount of a protein or peptide having a sialidase or an active portion thereof to a subject, (b) a composition or compound containing a therapeutically effective amount of a fusion protein, wherein the fusion protein has at least one catalytic domain of a sialidase, wherein the catalytic domain of the sialidase includes the sequence of amino acids extending from amino acid 274 to amino acid 666 of SEQ ID NO:12 (alternatively, 274 to 666, 270-667, 274-681, 290-681 of SEQ ID NO:12, or any other catalytic domain of Actinomyces viscosis), inclusive, and at least one anchoring domain, wherein the anchoring domain is a glycosaminoglycan (GAG) binding domain of human amphiregulin including the amino acid sequence of SEQ ID NO:7, or (c) a composition or compound containing a therapeutically effective amount of a fusion protein having a sialidase or an active portion thereof and an anchoring domain. The therapeutically effective amount of these compositions or compounds includes an amount that limits an increase in the quanitity of mucus in the respiratory tract of the subject above a baseline level after administration of the composition.

In some embodiments, the compositions or compounds used can include additional compounds, including, without limitation, any one or more of the following either alone or in various combinations: Na$_2$SO$_4$, MgSO$_4$, CaCl$_2$, Histidine, Histine-HCl, and Trehalose or their analogs, Mg salts and/or Ca salts. These additional compounds can be included in the pharmaceutical compositions to act as excipients or as active ingredients that provide additional beneficial effects.

The subjects to be treated with the foregoing methods can be human subjects or non-human animal subjects. The compounds and compositions described herein can be administered to epithelial cells of the subject through various routes of administration, including, without limitation, by using inhalers to introduce the compounds or compositions into the respiratory tract of the subject.

In some preferred embodiments, compounds described herein can be delivered asan inhalant with an inhaler or as a nasal spray. They can also be administered as eye drops, ear drops, or sprays, ointments, lotions, or gels to be applied to the skin. They can also be administered intravenously or as a local injection.

Reducing or Preventing Inflammation in the Respiratory Tract

The present invention involves the unexpected discovery that administration of the compounds described in U.S. application Ser. Nos. 10/718,986 and 10/939,262, or compositions containing them, to reduce the amount of inflammatory cells in the respiratory tract. Thus, the invention relates to therapeutic compositions or compounds that can be used to reduce inflammation in the respiratory tract or prevent worsening of inflammation in the respiratory tract. The invention also includes methods of reducing inflammation in the respiratory tract or preventing worsening of inflammation in the respiratory tract. In addition, the invention relates to therapeutic compositions or compounds that can be used to prevent or treat diseases that are caused by, cause, or are exacerbated by respiratory inflammation, such as, both allergic and non-allergic asthma, allergic rhinitis, eczema, psoriasis, reactions to plant or animal toxins, autoimmune conditions, and any other disorder, disease or condition that causes inflammation in the respiratory tract or is caused by or exacerbated by inflammation in the respiratory tract.

In some preferred embodiments, the methods include administering a composition or compound containing a therapeutically effective amount of a protein or peptide having a sialidase or an active portion thereof to a subject. The protein or peptide can be an isolated naturally occurring sialidase protein, or a recombinant protein substantially homologous to at least a portion of a naturally occurring sialidase. A preferred pharmaceutical composition contains a sialidase with substantial homology to the *A. viscosus* sialidase (SEQ ID NO:12) or substantial homology to an active portion thereof, such as amino acids 274-666, 274-667, 270-667, 274-681, or 290-681 of SEQ ID NO:12, or any other catalytic domain of *Actinomyces viscosis* sialidase. The therapeutically effective amount includes an amount of the protein or peptide that prevents or reduces an allergic or inflammatory response in the respiratory tract the respiratory tract after administration of the composition or compound.

In other embodiments, the methods include administering a composition or compound containing a therapeutically effective amount of a fusion protein, wherein the fusion protein has at least one catalytic domain of a sialidase, wherein the catalytic domain of the sialidase includes the sequence of amino acids extending from amino acid 274 to amino acid 666 of SEQ ID NO:12 (alternatively, 274 to 666, 270-667, 274-681, 290-681 of SEQ ID NO:12, or any other catalytic domain of *Actinomyces viscosis*), inclusive, and at least one anchoring domain, wherein the anchoring domain is a glycosaminoglycan (GAG) binding domain of human amphiregulin including the amino acid sequence of SEQ ID NO:7. The therapeutically effective amount includes an amount of the fusion protein that prevents or reduces an allergic or inflammatory response in the respiratory tract the respiratory tract after administration of the composition or compound.

In yet other embodiments, the methods include administering a composition or compound containing a therapeutically effective amount of a fusion protein having a sialidase or an active portion thereof and an anchoring domain. The therapeutically effective amount includes an amount of the fusion protein that prevents or reduces an allergic or inflammatory response in the respiratory tract the respiratory tract after administration of the composition or compound.

In some embodiments, the compositions or compounds used can include additional compounds, including, without limitation, any one or more of the following either alone or in various combinations: $Na_2SO_4$, $MgSO_4$, $CaCl_2$, Histidine, Histine-HCl, and Trehalose or their analogs. These additional compounds can be included in the pharmaceutical compositions to act as excipients or as active ingredients that provide additional beneficial effects.

The subjects to be treated with the foregoing methods can be human subjects or non-human animal subjects. The compositions and compounds described herein can be administered to epithelial cells of the subject through various routes of administration, including, without limitation, by using inhalers to introduce the compounds or compositions into the respiratory tract of the subject.

In some preferred embodiments, compositions or compounds described herein can be delivered as an inhalant with an inhaler or as a nasal spray. They can also be administered as eye drops, ear drops, or sprays, ointments, lotions, or gels to be applied to the skin. They can also be administered intravenously or as a local injection.

Figure 7B:
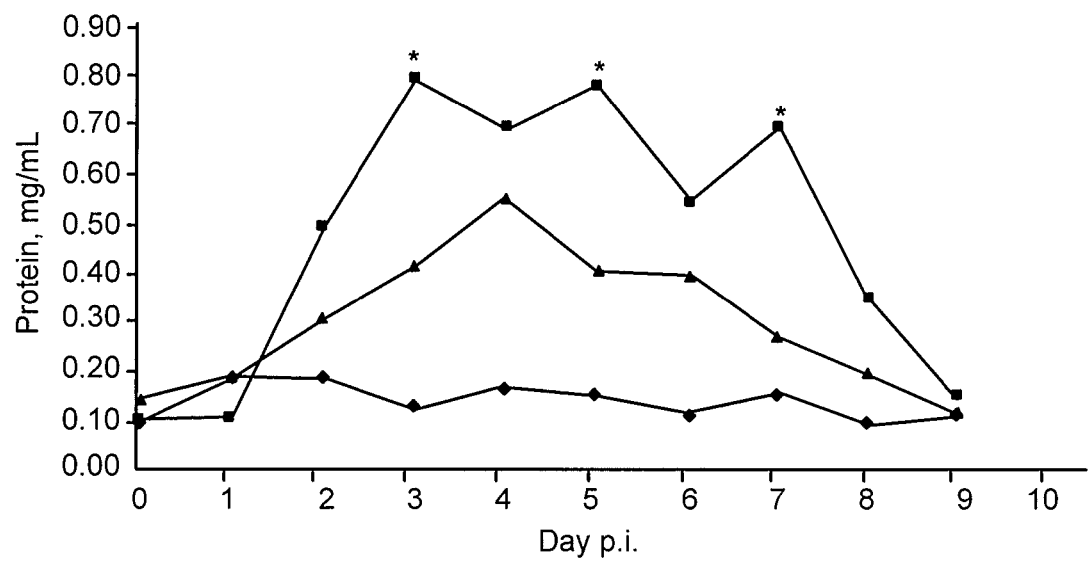

FIGS. 7A-B show the results of the effect of the use of one of the fusion protein construct depicted in FIG. 5 on inflammatory cells of ferrets infected with human unadapted influenza. In ferrets that shed the virus despite treatment with fusion protein (n=8), the inflammatory response was reduced and animals appeared to be more alert and active compared to the untreated ferrets that were invariably lethargic and feverish. For this group of 8 infected, fusion-protein treated animals, the mean AUC (area under the curve) value calculated for the nasal protein concentrations was reduced by approximately 40% (2.68 vs. 4.48, arbitrary units) compared to the vehicle-treated (phosphate buffer saline) infected animals (FIG. 7B). In vehicle-treated infected animals, the number of inflammatory cells in nasal washes was increased to approximately 100-fold above those in uninfected animals on day 2 post challenge. These levels were sustained for 4 additional days. The fusion protein-treated animals exhibited a significant reduction in the number of inflammatory cells in the nasal washes. Specifically, the AUC value for cell counts was reduced by approximately 3-fold in the fusion protein-treated animals compared to the vehicle-treated infected animals (1965 vs. 674, arbitrary units, (FIG. 7B). The observed reduction in the inflammatory response indicates the importance of inhibiting viral replication at the early stage of infection.

Dosage

As will be readily apparent to one skilled in the art, the useful in vivo dosage to be administered and the particular mode of administration will vary depending upon the age, weight and type of patient being treated, the particular pharmaceutical composition employed, and the specific use for which the pharmaceutical composition is employed. The determination of effective dosage levels, that is the dose levels necessary to achieve the desired result, can be accomplished by one skilled in the art using routine methods as discussed above. In non-human animal studies, applications of the pharmaceutical compositions are commenced at higher dose levels, with the dosage being decreased until the desired effect is no longer achieved or adverse side effects are reduced or disappear. The dosage for a compound of the present invention can range broadly depending upon the desired affects, the therapeutic indication, route of administration and purity and activity of the compound. Typically, human clinical applications of products are commenced at lower dosage levels, with dosage level being increased until the desired effect is achieved. Alternatively, acceptable in vitro studies can be used to establish useful doses and routes of administration of the test compound. Typically, dosages can be between about 1 ng/kg and about 10 mg/kg, between about 10 ng/kg and about 1 mg/kg, and between about 100 ng/kg and about 100 micrograms/kg. In various examples described herein, mice were treated with various dosages of the compositions described herein, including dosages of 0.0008 mg/kg, 0.004 mg/kg, 0.02 mg/kg, 0.06 mg/kg, 0.1 mg/kg, 0.3 mg/kg, 0.6 mg/kg, and 1.0 gm/kg. As nonlimiting examples, the compositions described herein can be administered to humans in doses of between about 0.01 mg and about 100 mg, such as about 0.05 mg, 0.06 mg, 0.1 mg, 0.5 mg, 1 mg, 5 mg, 10 mg, 20 mg, 50 mg, or 100 mg, and can be administered one or more times per day, for one day, two days, three days, four days, five days, six days, seven days, eight days, nine days, ten days, eleven days, twelve days, thirteen days, or fourteen or more days. Higher doses or lower doses can also be administered. In one embodiment, as shown in Example 3 below, a dose of 0.06 mg/kg of a sialidase compound is sufficient to desialylate muscarinic receptors resulting in reduced airway responsiveness to muscarinic receptor agonists, and thus potentially resulting in reducing airway constriction, airway hypersensitivity, inflammation, allergies or associated responses, such as bronchoconstriction, asthma, and mucus overproduction. Efficacy in low doses, such as 0.06 mg/kg (translating in adult humans into a dose of about 4 or 5 mg), or 0.02 mg/kg (translating in adult humans into a dose of about 1 or 2 mg), makes the sialidase-based compounds described herein good candidates for use in chronic diseases that require repeated long-term administration.

A treatment regimen can include administration of the compounds and compositions described herein from once per day to ten times per day, from once per day to six times per day, from once per day to five times per day, from once per day to four times per day, from once per day to three times per day, from once per day to twice per day, and just once per day. The treatment can last from just one day to daily, weekly, monthly, or other periodic use for a predetermined period of time or for the remainder of the subject's life.

The exact formulation, route of administration and dosage can be chosen by the individual physician in view of the patient's condition (see, Fingle et al., in The Pharmacological Basis of Therapeutics (1975)). It should be noted that the attending physician would know how to and when to terminate, interrupt or adjust administration due to toxicity, organ dysfunction or other adverse effects. Conversely, the attending physician would also know to adjust treatment to higher levels if the clinical response were not adequate. The magnitude of an administrated does in the management of the disorder of interest will vary with the severity of the condition to be treated and to the route of administration. The severity of the condition may, for example, be evaluated, in part, by standard prognostic evaluation methods. Further, the dose and perhaps dose frequency, will also vary according to the age, body weight and response of the individual patient, including those for veterinary applications.

In some preferred regimens, appropriate dosages are administered to each patient by either inhaler, nasal spray, or by topical application. It will be understood, however, that the specific dose level and frequency of dosage for any particular patient may be varied and will depend upon a variety of factors including the activity of the specific salt or other form employed, the metabolic stability and length of action of that compound, the age, body weight, general health, sex, diet, mode and time of administration, rate of excretion, drug combination, the severity of the particular condition, and the host undergoing therapy.

In some embodiments, the present disclosure provides methods for using any one or more of the compositions (indicated below as 'X') disclosed herein in the following methods:

Substance X for use as a medicament in the treatment of excess mucus or abnormal (e.g., above normal mucus levels as compared to one or more healthy subjects (e.g., of the same ethnicity and/or in the same or similar geographical location) and/or as indicated by a health care practitioner), elevated mucus production, and/or any one or more of the diseases/conditions disclosed herein; (each of which is collectively referred to in the following examples as 'Y.'

Use of substance X for the manufacture of a medicament for the treatment of Y; and Substance X for use in the treatment of Y.

EXAMPLES

The invention is further described in the following examples, which do not limit the scope of the invention described in the claims.

Example 1

Effect of Sialidase Treatment on the Early and Late Asthmatic Reaction in Guinea Pigs 1. Overview In this study Fludase® was tested in a guinea pig model of allergic asthma. Guinea pigs were sensitised with ovabumin (OVA) or saline and after 15 or 20 days they were treated with Fludase® or sodium sulfate. On day 21, all the animals were challenged with OVA to measure the early asthmatic reaction. Airway compliance/resistance were determined and broncho-alveolar lavage (BAL) fluid was taken from the left lung to count the total number of cells and to differentiate them.

2. Introduction

The main purpose of this study was to achieve a characterization of the effect of Fludase® on the early and late reactions in a guinea pig model for asthma. The guinea pigs involved in the study were naïve, and thus not infected with influenza or other infectious agent as part of the experiment. Asthma was induced by sensitising the guinea pigs on day 0 with OVA. After 15 or 20 days the guinea pigs were treated intatracheal with Fludase® (0.3 mg/kg) or sodium sulfate (0.143 mM, pH 5.0). On day 21 the guinea pigs received an OVA aerosol and the airway responsiveness (PenH) was measured. On day 22 the pulmonary resistance and compliance were determined. At time intervals of 2 minutes doses of histamine from 0.2-2 µg/kg were administered by intravenously injection. At the end of the experiment guinea pigs were sacrificed and the left lung was lavaged and the isolated BAL cells were washed, counted and differentiated into macrophages, lymphocytes, neutrophils and eosinophils.

3. Materials & Methods

Animals

Male Hartley-strain guinea pigs (HSD Poc: DH, weighing 400-500) of specific pathogen free quality were obtained from Harlan-CPB (Zeist, The Netherlands). They were used after 1 week of acclimatisation to their housing conditions. Water and commercial chow were allowed ad libitum. The experiments were approved by the Animal Ethics Committee of the Utrecht University (Utrecht, The Netherlands).

Sensitisation, Pre-Treatment & Challenge

Guinea pigs were sensitised with saline (solutions contains 100 mg/ml Al(OH)$_3$) or OVA (solution contains 20 µg/ml OVA and 100 mg/ml Al(OH)$_3$), administered intraperitoneally 0.5 ml and subcutanously 5×0.1 ml, total injection volume 1 ml. After 15 or 20 days animals were treated once with 0.3 mg/kg Fludase® and the control animals were treated with sodium sulfate (0.143 mM, pH 5.0) on day 20 by tracheal instillation. A laryngoscope was used to facilitate the location of the epiglottis. Then the Fludase® or sodium sulfate was given with a liquid aerosol using the IA-1C MicroSprayer™ (Penn Century, Inc, Philadelphia, USA). The guinea pig was in an upright position during the tracheal instillation.

During this tracheal instillation the guinea pigs were anaesthetized with 150 µl of a mixture of Ketamine®, Xylazin®, Atropin and saline (3.5:3:1:3), injected intra muscular in the hind paw.

On day 21 the guinea pigs were challenged by exposure to an aerosol OVA (0.1% wt/vol in sterile saline). The aerosol was generated into a 3 liter perspex chamber in which the guinea pigs were placed. First the basal bronchoconstriction (PenH) was measured. The guinea pigs were provoked with OVA aerosol for 10 seconds. Directly after the challenge the early asthmatic reaction was (PenH) was measured.

Allergen-Induced Early Asthmatic Reaction in Conscious Unrestrained Guinea Pigs

Airway function of the animals was measured directly after exposure to aerosolised OVA in a ventilated bias flow whole body plethysmograph (Buxco Electronics, Sharon Conn., USA). The plethysmograph consists of a reference chamber and an animal chamber. The animal chamber is attached to the outside via a pneumotachograph in the top of the plethysmograph. An aerosol inlet to the animal chamber is centrically located in the roof of the animal chamber. When an animal is placed in the animal chamber and is breathing quietly, it creates pressure between tidal volume and thoracic movement during respiration. The differential pressure transducer measures the changes in pressure between animal chamber and the reference chamber and brings these data to a preamplifier. Thereafter, data is sent to a computer where several parameters are calculated, which represents animal's lung function. All guinea pigs used were measured basal for 5 minutes and after the aerosol for 15 minutes in the whole body plethysmograph. Besides known lung function parameters as peak expiratory flow (PEF) and tidal volume (TV), the enhanced pause (PenH) was also measured. The formula and explanation of the PenH is shown in FIG. 8. During bronchoconstriction peak expiratory flow and peak inspiratory flow are increased, while relaxation time and expiratory time are decreased. This results in an increased PenH. Data from bronchoconstriction in conscious unrestrained guinea pigs are presented in PenH (FIG. 8).

Airway Responsiveness In Vivo

On day 22 the guinea pigs were anaesthetized with urethane 2 g/kg intra peritoneally. The animals were allowed to breathe spontaneously. An anaesthesia-induced fall in body temperature was avoided by placing the animals in a heated chamber, which kept the body temperature at 37° C. The guinea pigs were prepared for the measurement of pulmonary resistance ($R_L$) and compliance (C) as follows. A small polyethylene catheter (PE-50) was placed in the right jugular vein for intra venous administration of increasing doses of histamine (0.2-2 µg/kg). First the basal $R_L$ and C were measured for 5 minutes. Thereafter an increasing dose of histamine was injected and $R_L$ and C were measured for 2 minutes. Airflow and tidal volume were determined by cannulating and connecting the trachea with Fleisch flow head (nr 000; Meijnhart, Bunnik, The Netherlands) to a pneumotachograph. A pressure transducer (model MP45-2; Validyne Engineering Corp., Northridge, Calif.) measured the transpulmonary pressure by determining pressure differences between the tracheal cannula and a cannula filled with saline inserted in the oesophagus. $R_L$ and C were determined breath by breath with a respiratory analyser. $R_L$ was yielded by dividing transpulmonary pressure by airflow at isovolume points. C was determined by dividing volume by transpulmonary pressure at isoflow points. Data are presented as maximal $R_L$ and minimal C in cm $H_2O$/ml*sec$^{-1}$ an ml/cm $H_2O$, respectively.

Collection of Broncho-Alveolar Lung Lavage Cells

Broncho-alveolar lavage cells were obtained as follows. The trachea was trimmed free of connective tissue and blood vessels and a small incision was made for insertion of a cannula into the trachea. The right lung was tied up so only the left lung was lavaged. The left lung was filled with 5 ml saline (0.9% NaCl) of 37° C. in situ. Fluid was withdrawn from the lung after gentle massage and collected in a plastic tube on ice (4° C.). This procedure was repeated 3 times (total 15 ml) and the cell suspensions recovered from each animal were pooled. Thereafter, cells were sedimented by centrifugation at 1500 rpm for 5 minutes at 4° C. The supernatant solution was thrown away and the pellet was resuspended in 1 ml saline.

Only plastic tubes were used throughout the isolation procedure in order to minimize adherence of the cells to the walls of the tubes.

Cell Count and Differentiation

The cells were stained with Türk solution and counted in a Bürker-Türk bright-line counting chamber (microscope, magnification 100×). For differential BAL cell counts cytospin preparations were made and stained with Diff-Quick (Merz & Dade A. G., Düdingen, Switzerland). After coding all cytospin preparations were evaluated by one observer using oil immersion microscopy (magnification 1000×). Cells were differentiated into macrophages, lymphocytes, neutrophils and eosinophils by standard morphology. At least 200 cells per cytospin preparation were counted and the absolute number of each cell type was calculated.

Statistical Analysis

Unless stated otherwise, data are expressed as arithmetic average±standard error of mean and comparisons between groups were made using Student's t-test. A probability value $p<0.05$ was considered significant.

4. Results

Airway Responsiveness in Conscious Unrestrained Guinea Pigs

Figure 9:
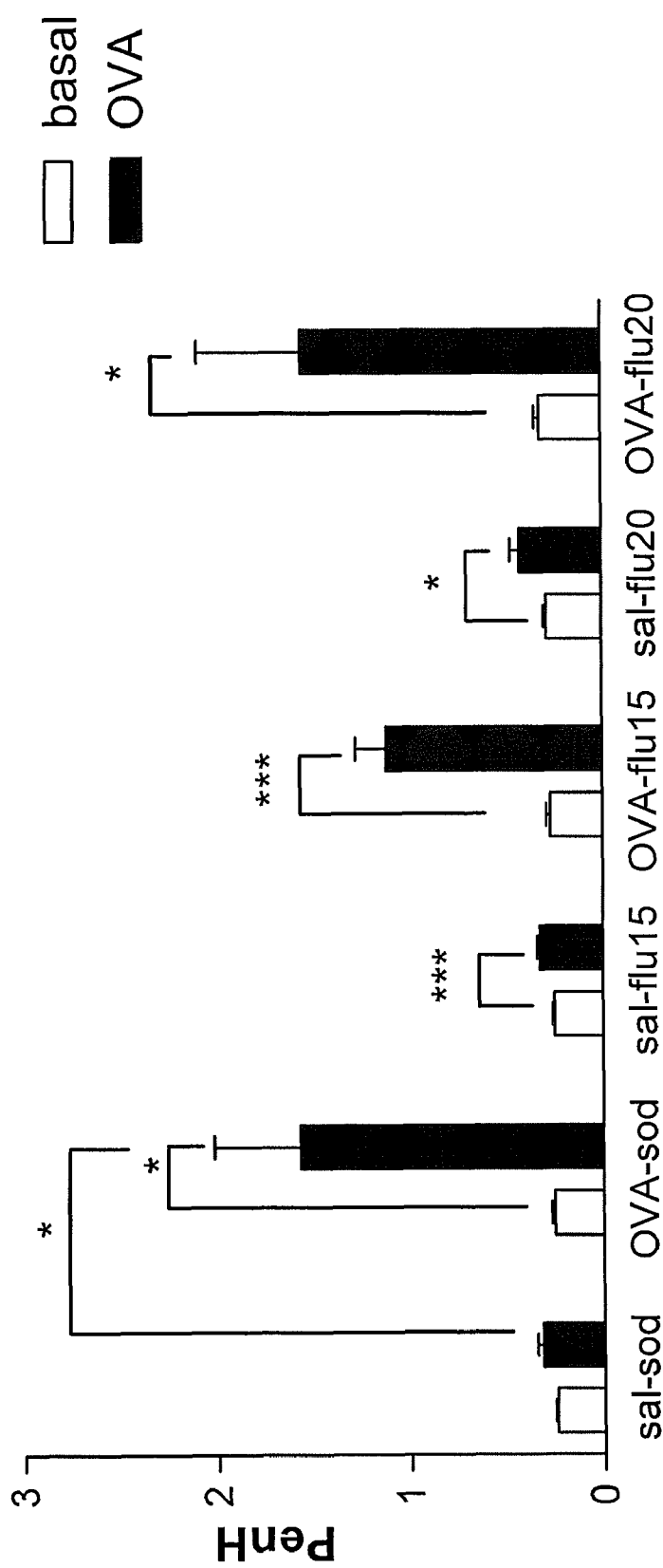

As shown in FIG. 9, basal airway resistance was not different between the saline guinea pigs treated with sodium sulfate or DAS181 on day 15 or day 20 (PenH=0.24±0.009 sal-sodium sulfate, 0.25±0.01 saline-Flu day 15, 0.28±0.01 sal-Flu day 20 treated guinea pigs). There was also no difference between the OVA guinea pigs treated with sodium sulfate or Fludase® on day 15 or day 20 at basal level (PenH=0.25±0.01 OVA-sodium sulfate, 0.27±0.02 OVA-Flu day 15, 0.31±0.03 OVA-Flu day 20 treated guinea pigs).

Ova challenge slightly increased the basal airway resistance in saline sensitized animals (SOD, Flu 15 and 20, FIG. 2). However, the early asthmatic reaction in response to the OVA aerosol was strongly increased in the OVA-sodium sulfate treated guinea pigs (PenH=1.57±0.45). After treatment with Fludase® the early asthmatic reaction was decreased by nearly 30% on day 15, but not on day 20.

Cell Count in Broncho-Alveolar Lavage Fluid

Figure 10:
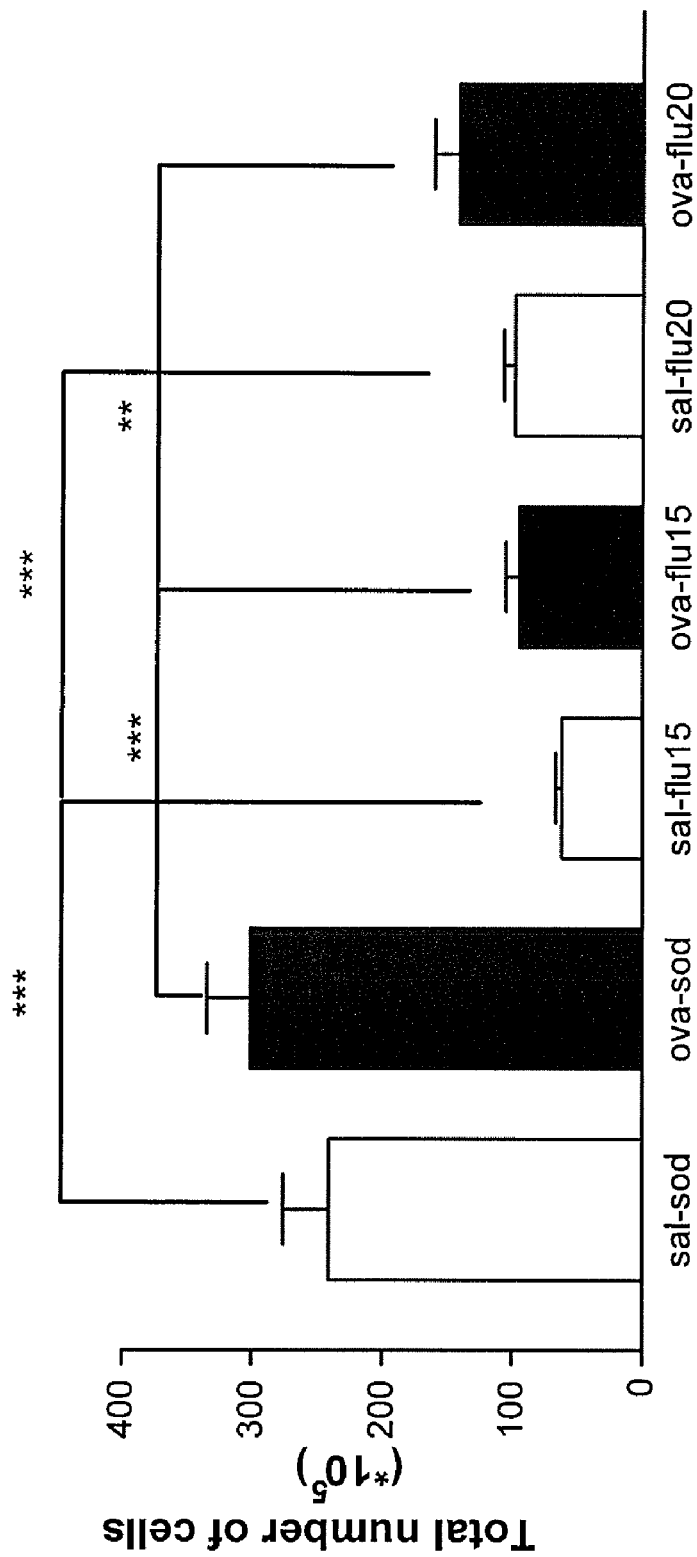

As shown in FIG. 10, Fludase® decreases the total number of cells both in saline and OVA guinea pigs.

Differential Cell Count in the Broncho-Alveolar Lavage Fluid

Figure 11:
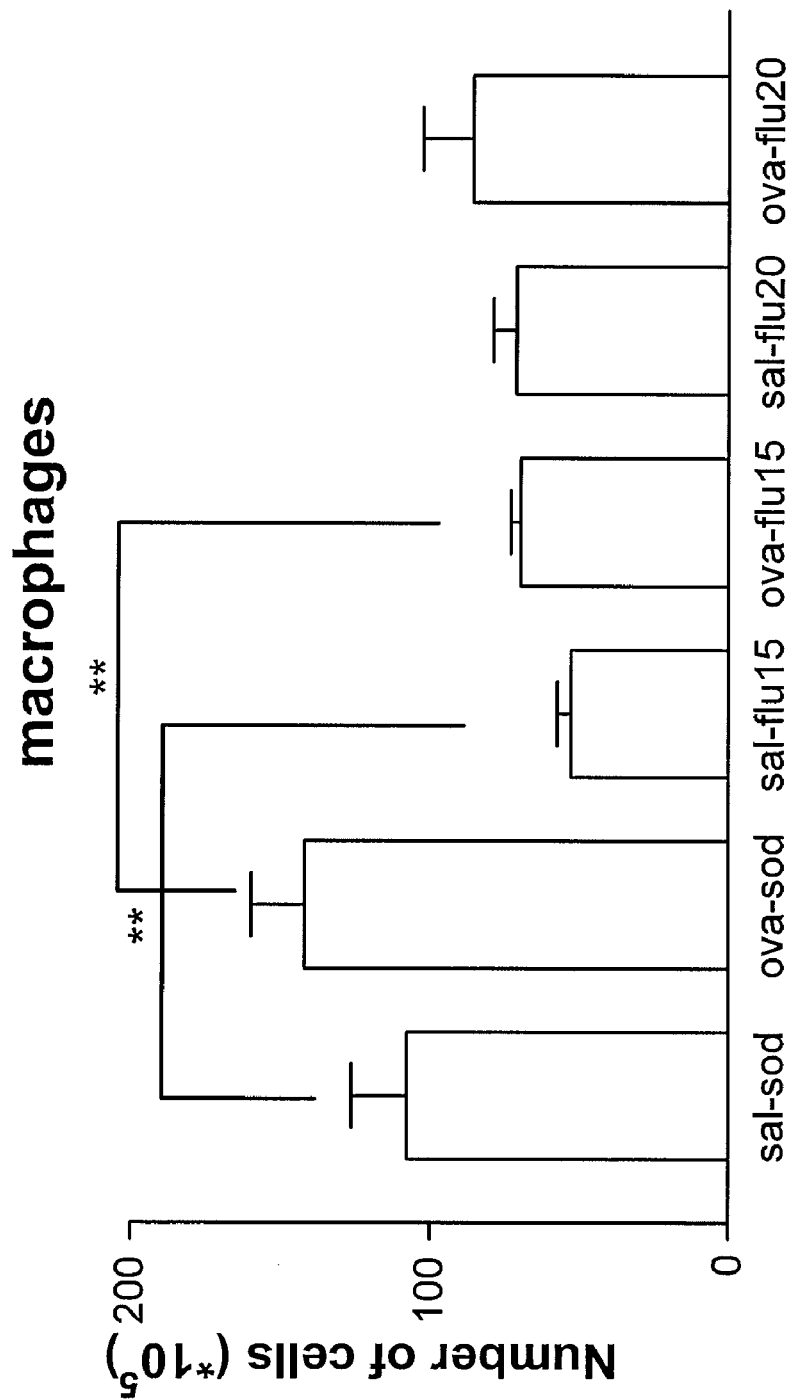

As shown in FIG. 11, the number of macrophages was enhanced by (30%) in the OVA guinea pigs compared to the saline treated group. Total number of macrophages was strongly decreased after treatment with Fludase® on day 15 and 20, both in saline and OVA treated guinea pigs.

Figure 12:
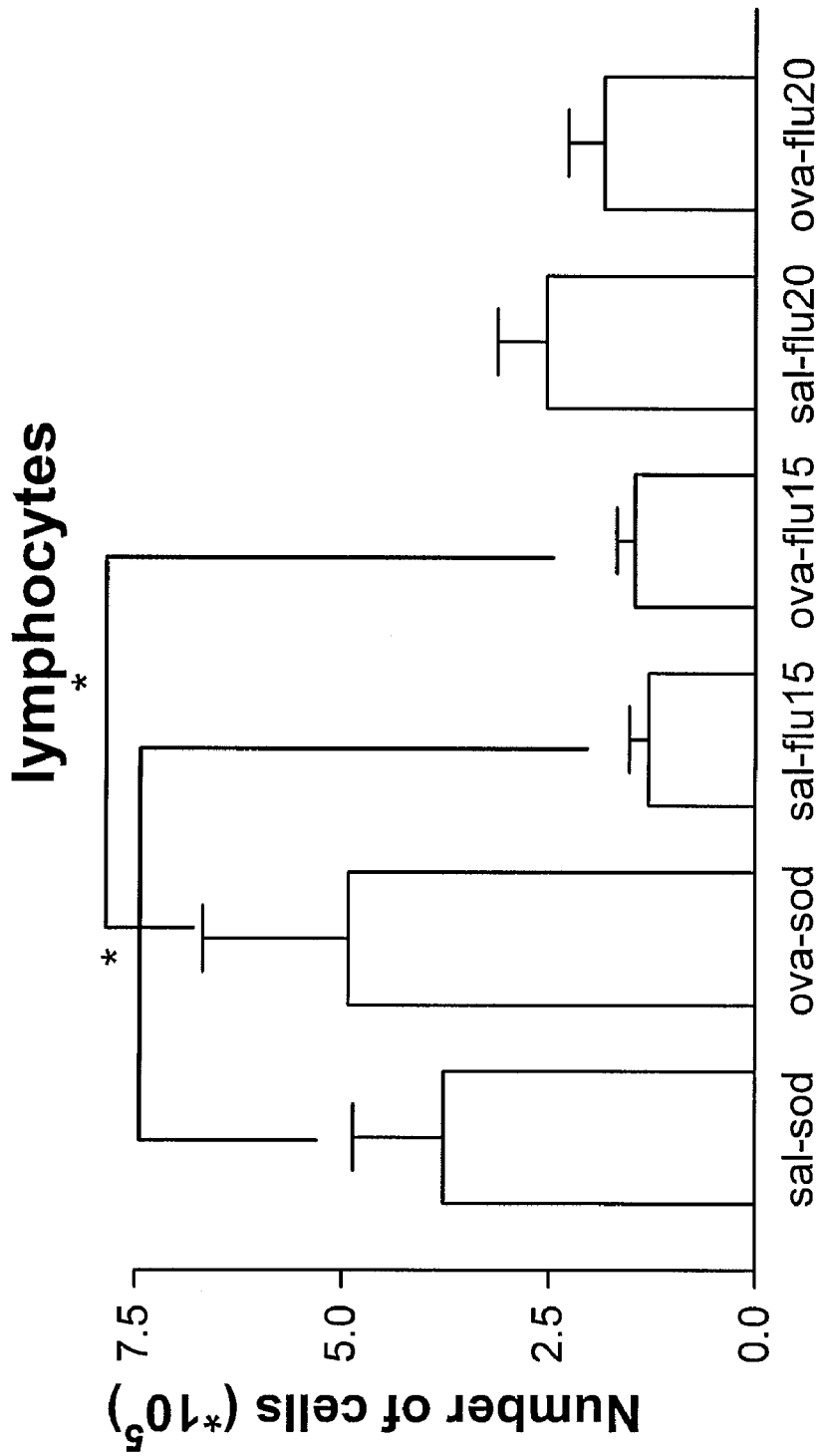

As shown in FIG. 12, a similar pattern was observed with the number of lymphocytes. The number of lymphocytes is decreased after Fludase® treatment.

Figure 13:
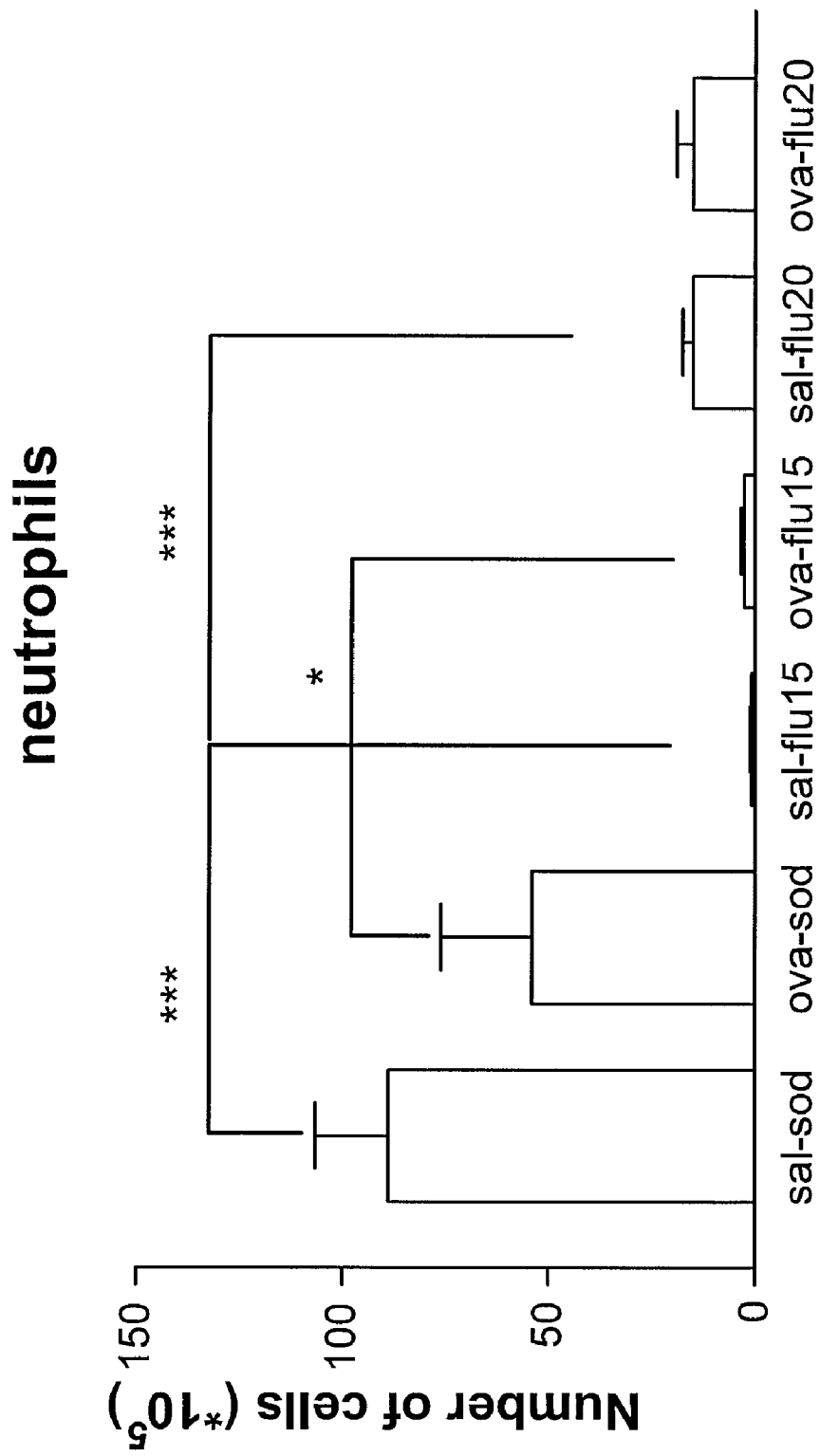

As shown in FIG. 13, compared to historical controls, SOD induces a strong increase in the number of neutrophils into the lungs. Interestingly, Fludase® completely prevented this influx in both the saline and OVA groups.

Figure 14:
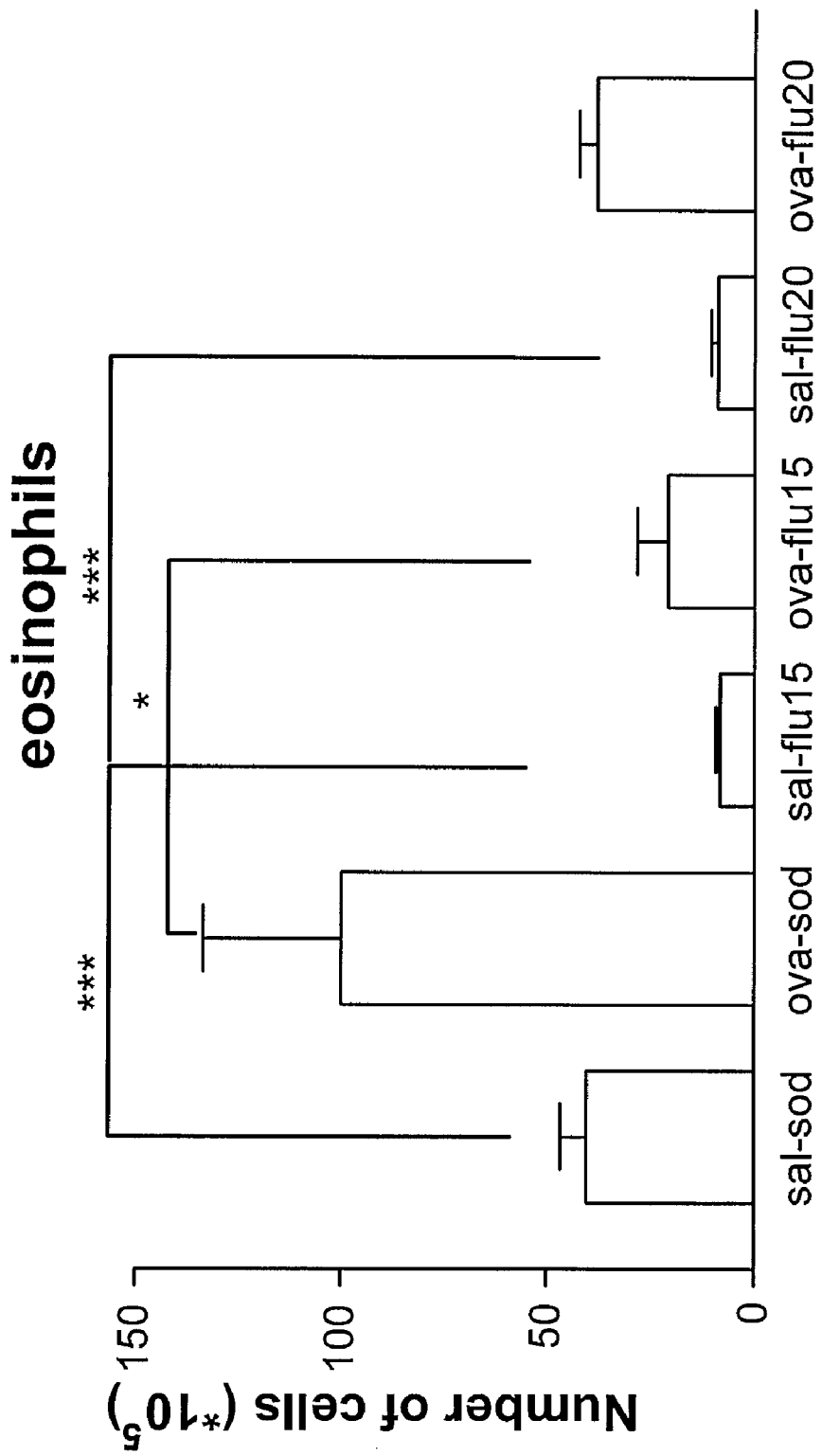

As shown in FIG. 14, compared to historical controls SOD induces also an eosinophil influx into the airways, which is further increased by OVA challenge. Interestingly, Fludase® treatment can restore the number of eosinophils up to historical control levels.

5. Discussion/Conclusion

OVA-sensitised and challenged animals demonstrate an early and late asthmatic reaction as measured by an increase in PENH up on OVA-challenge, and an increase in the number of inflammatory cells in the BAL-fluid.

Interestingly, Fludase® (Flu15) reduced the early asthmatic response by nearly 30% (FIG. 9), suggesting an effect of this compound on mast cell stimulation. Moreover, Fludase® had a tremendous effect on the inflammation caused by SOD or OVA. The number of all inflammatory cells (macrophages, lymphocytes, neutrophils and eosinophils) was significantly decreased by this compound.

In conclusion, Fludase® demonstrated to be effective in both the SOD-induced inflammation and the OVA-induced inflammation.

Example 2

The Effect of Fludase in a Mouse Model of Acute OVA Induced Asthma

1. Introduction

The aim of the study was to investigate whether Fludase® (also referred to as DAS181) (1) inhibits allergen induced airway inflammation and airway hyperreactivity in an acute OVA challenge mouse model of asthma. In addition to studying the effect of DAS181 alone as an intervention, three other interventions in the mouse asthma model were studied including a) DAS181+an excipient (used as the dry powder formulation to deliver DAS181 in vivo), b) the excipient alone, and c) dexamethasone (as a comparator).

2. Materials and Methods

Mice

Female BALB/c mice age 12 weeks were purchased from Charles River and housed in the UCSD vivarium. They were used after approximately one week of acclimatization in the UCSD vivarium.

OVA Sensitization and OVA Challenge

Mice were immunized s.c. on days 0, 7, 14, and 21 with 25 ug of OVA adsorbed to 1 mg of alum in 200 ul normal saline to induce a predominant Th2 immune response. Intranasal OVA challenges (20 ug/50 ul) were started on day 26 and then repeated on day 28 and day 30. In the no OVA group, mice were sensitized to OVA but not challenged intranasally with OVA. Mice had airway responsiveness to methacholine (Mch) measurements performed 24 hours after the final OVA challenge by Penh on day 31. The mice involved in the study were naïve and thus not infected with influenza or other infectious agent as part of the experiment. Mice were then immediately sacrificed. Bronchoalveolar lavage fluid (BAL), blood, and lung tissue were processed for outcomes detailed below.

Administration of Test Compounds to Mice

1. Compounds Tested

The following compounds were studied in the mouse model of asthma a) DAS181 with excipient (0.6 mg/kg intranasal): DAS181-F02 (NexBio, Inc. part #43-071, lot #47-034) was prepared in PBS to 20 mgDAS/ml. Before each dosing, it was freshly diluted in PBS to 0.6 mg DAS181/kg with dosing volume of 50 ul, for mice with an average body weight of 21 g.

b) DAS181 (0.6 mg/kg intranasal)

c) Excipient (50 μL/mouse): Excipient (416TL022A) was supplied by NexBio, Inc. as a solution, and the concentration of each of the excipient component is equivalent to that in 20 mgDAS181/ml ($MgSO_4$ 1.446 mg/ml, $CaCl_2$ 0.059 mg/ml, Histidine 1.427 mg/ml, Histidine-HCl 1.943 mg/ml, and Trehalose 3.000 mg/ml). It was freshly diluted in PBS for dosing as in a). The final concentration of each excipient component is equivalent to that in 0.6 mgDAS181/kg, in 50 ul, for mice with average body weight of 21 g.

d) Dexamethasone (1.0 mg/kg intraperitoneally)

Excipient solution was prepared in the following manner. The target final concentration for each excipient was calculated to reach equivalent concentration when DAS181-F02 bulk dry powder is reconstituted at a 20 mg protein/mL. The 10× stock solutions (100× for Calcium Chloride) for each excipient (10 mL each) were then prepared. Materials used to prepare the stock solutions are listed in Table 1. All materials are USP grade, or equivalent. Appropriate amounts of each excipient were weighed into a 15 mL conical tube according to Table 2, and water was added to bring the total weight to 10 grams and vortex to dissolve the material completely. The final 1× excipient solution was prepared by adding 1 mL of each stock solution, and then bringing the volume to 10 mL using water. All sample preparation was preformed gravimetrically, assuming solution density of 1 gram/mL.

Although referred to as "excipient" or "excipient" solution in these examples, these additional compounds can have additional beneficial effects with respect to reduction of mucus and reduction of inflammation and inflammatory cells. These excpients can also have a synergistic effect with DAS181.

TABLE 1

Material Information

| Description | Manufacturer | Mfg. Part # | Mfg. Lot # | Expiry |
|---|---|---|---|---|
| L-Histidine | Sigma | H6034-100g | 078K0179 | September 2012 |
| L-Histidine monohydrochloride monohydrate | Sigma | H4036-1kg | 068K8310 | January 2012 |
| a,a - Trehalose, Dihydrate | J. T. Baker | 4226-04 | G47596 | November 2010 |
| Magnesium Sulfate Heptahydrate | EMD | 1.05882.0500 | K38528682R | February 2013 |
| Calcium Chloride, Dihydrate | Mallinckrodt | 4616-04 | G24475 | September 2009 |
| WFI | B. Braun | S9200-SS | J8K015 | August 2010 |

TABLE 2

Stock Solution Preparation Sheet (Theoretical)

| Composition | Final conc. (mg/mL) | Dilution Factor | Stock conc. (mg/mL) | Wt. of Salt for 10 mL (mg) |
|---|---|---|---|---|
| $MgSO_4$ | 1.446 | 10 | 14.457 | 296 |
| $CaCl_2$ | 0.059 | 100 | 5.943 | 79 |
| Histidine | 1.427 | 10 | 14.266 | 143 |
| Histidine•HCl | 1.943 | 10 | 19.431 | 213 |
| Trehalose | 3.000 | 10 | 30.000 | 332 |

2. Mouse Model of Asthma

The following groups of Balb/c mice (n=10 female mice/group) were studied.

a) No OVA
b) OVA
c) OVA+DAS181 with excipient
d) OVA+DAS181
e) OVA+excipient
f) OVA+dexamethasone 3. Timing of Administration of Test Compounds The test compounds were administered one hour prior to each of the three intranasal OVA challenges on days 26, 28, and 30.

Timing of End-Points Studied

Mice were sacrificed 24 hours after the final OVA challenge and blood, BAL, and lungs were analyzed (27).

4. End-Points Studied a) Penh

Airway responsiveness was assessed on day 31, twenty four hours after the final OVA inhalation, using a single chamber whole body plethysmograph obtained from Buxco (Troy, N.Y.). In this system, an unrestrained, spontaneously breathing mouse is placed into the main chamber of the plethysmograph, and pressure differences between this chamber and a reference chamber are recorded. The resulting box pressure signal is caused by volume and resultant pressure changes during the respiratory cycle of the mouse. A low pass filter in the wall of the main chamber allows thermal compensation. From these box pressure signals, the phases of the respiratory cycle, tidal volumes, and the enhanced pause (Penh) can be calculated. Penh is a dimensionless value that represents a function of the proportion of maximal expiratory to maximal inspiratory box pressure signals and of the timing of expiration. It correlates closely with pulmonary resistance measured by conventional two-chamber plethysmography in ventilated mice. In the plethysmograph, mice were exposed for 3 min to nebulized PBS and subsequently to increasing concentrations of nebulized metacholine (MCh) (3, 6, 12, 24, 48 mg/ml Mch) (Sigma, St. Louis, Mo.) in PBS using an Aerosonic ultrasonic nebulizer (DeVilbiss). After each nebulization, recordings were taken for 3 min. The Penh values measured during each 3-min sequence were averaged and are expressed for each MCh concentration as the percentage of baseline Penh values following PBS exposure.

b) Blood Eosinophil Counts

Peripheral blood was collected from mice by cardiac puncture into EDTA-containing tubes. Erythrocytes were lysed using a 1:10 solution of 100 mM potassium carbonate-1.5 M ammonium chloride. The remaining cells were resuspended in 1 mL PBS. To perform differential cell counts, 200 μL resuspended peripheral-blood leukocyte suspensions were cytospun onto microscope slides and air-dried. Slides were stained with Wright-Giemsa and the % of eosinophils in the total number of white blood cells were assessed under a light microscope.

c) PAS Staining for Lung Mucus

To quantitate the level of mucus expression in the airway, the number of periodic acid Schiff (PAS)-positive and PAS-negative epithelial cells in individual bronchioles were counted as previously described (Zhang, M., T. Angata, J. Y. Cho, M. Miller, D. H. Broide, A. Varki. 2007 Blood. 109: 4280-4287). At least ten bronchioles were counted in each slide. Results are expressed as the percentage of PAS-positive cells per bronchiole, which is calculated from the number of PAS-positive epithelial cells per bronchus divided by the total number of epithelial cells of each bronchiole. Slides of lung tissue with no OVA, OVA and OVA+DAS181 were also taken and observed.

d) MBP Staining of Lungs for Peribronchial Eosinophils

Lungs from the different experimental groups were processed as a batch for either histologic staining or immunostaining under identical conditions as described in Zhang et al. Stained and immunostained slides were all quantified under identical light microscope conditions, including magnification (20×), gain, camera position, and background illumination. Lung sections were processed for MBP immunohistochemistry as described above, using an anti-mouse MBP (Major Basic Protein) Ab (kindly provided by James Lee PhD, Mayo Clinic, Scottsdale, Ariz.) and the immunoperoxidase method as previously described in Zhang et al. Major Basic Protein is an eosinophil cytoplasmic granule protein which serves as a marker of eosinophils in tissues. The number of individual cells staining positive for MBP in the peribronchial space were counted using a light microscope. Results are expressed as the number of peribronchial cells staining positive for MBP per bronchiole with 150-200 μm of internal diameter. At least ten bronchioles were counted in each slide.

5. Statistical Analysis

Results in the different groups of mice were compared by Mann Whitney non-parametric T test. All results are presented as mean±SEM. A statistical software package (Graph Pad Prism, San Diego, Calif.) was used for the analysis. P values of <0.05 were considered statistically significant.

6. Results a) Penh

Figure 15:
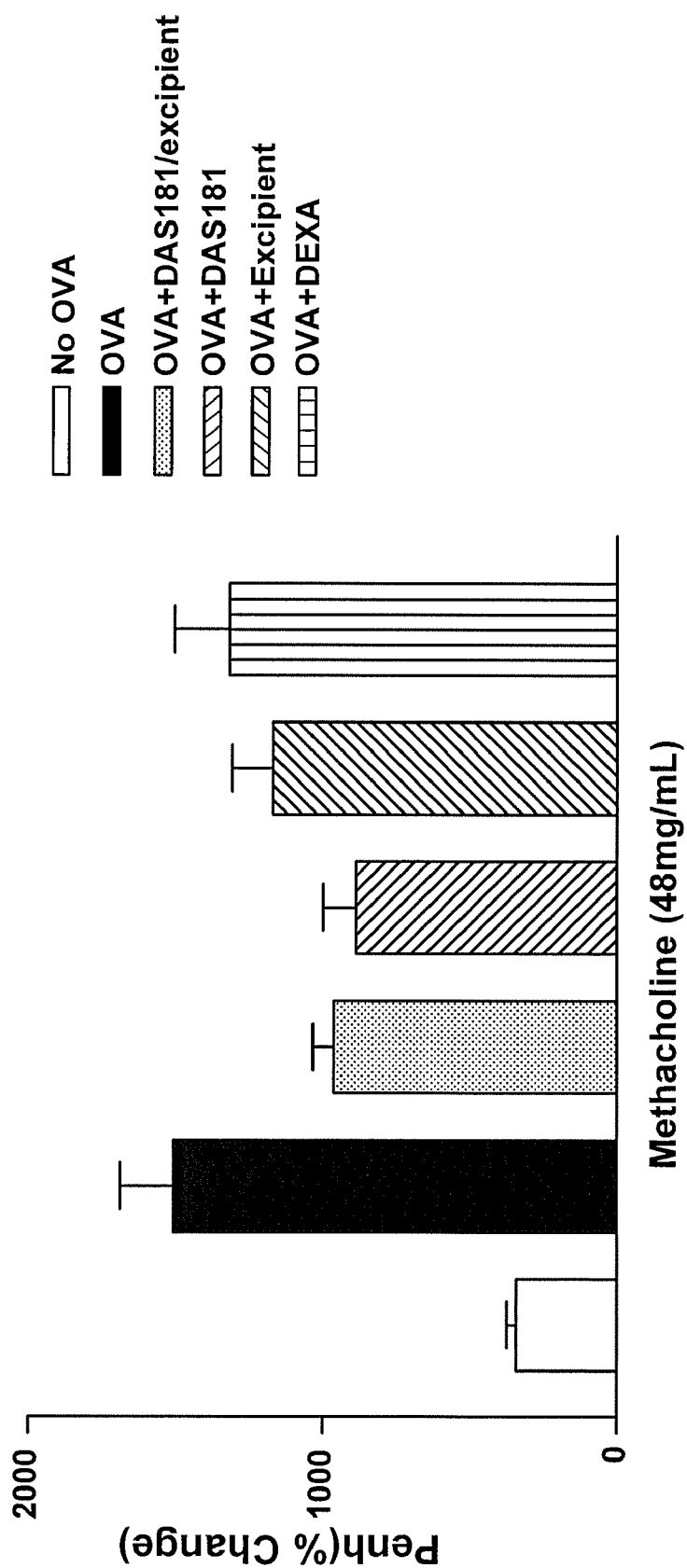

As shown in FIG. 15, OVA challenge induced a significant increase in airway responsiveness as assessed by changes in Penh (OVA vs no OVA; p<0.0001).

OVA challenged mice pre-treated with DAS181+excipient had a significant reduction in Penh compared to OVA challenged mice (OVA vs OVA+DAS181+excipient; p<0.01).

OVA challenged mice pre-treated with DAS181 resulted in a reduction in Penh compared to OVA challenged mice (OVA vs OVA+DAS181; p<0.005).

Figure 16:
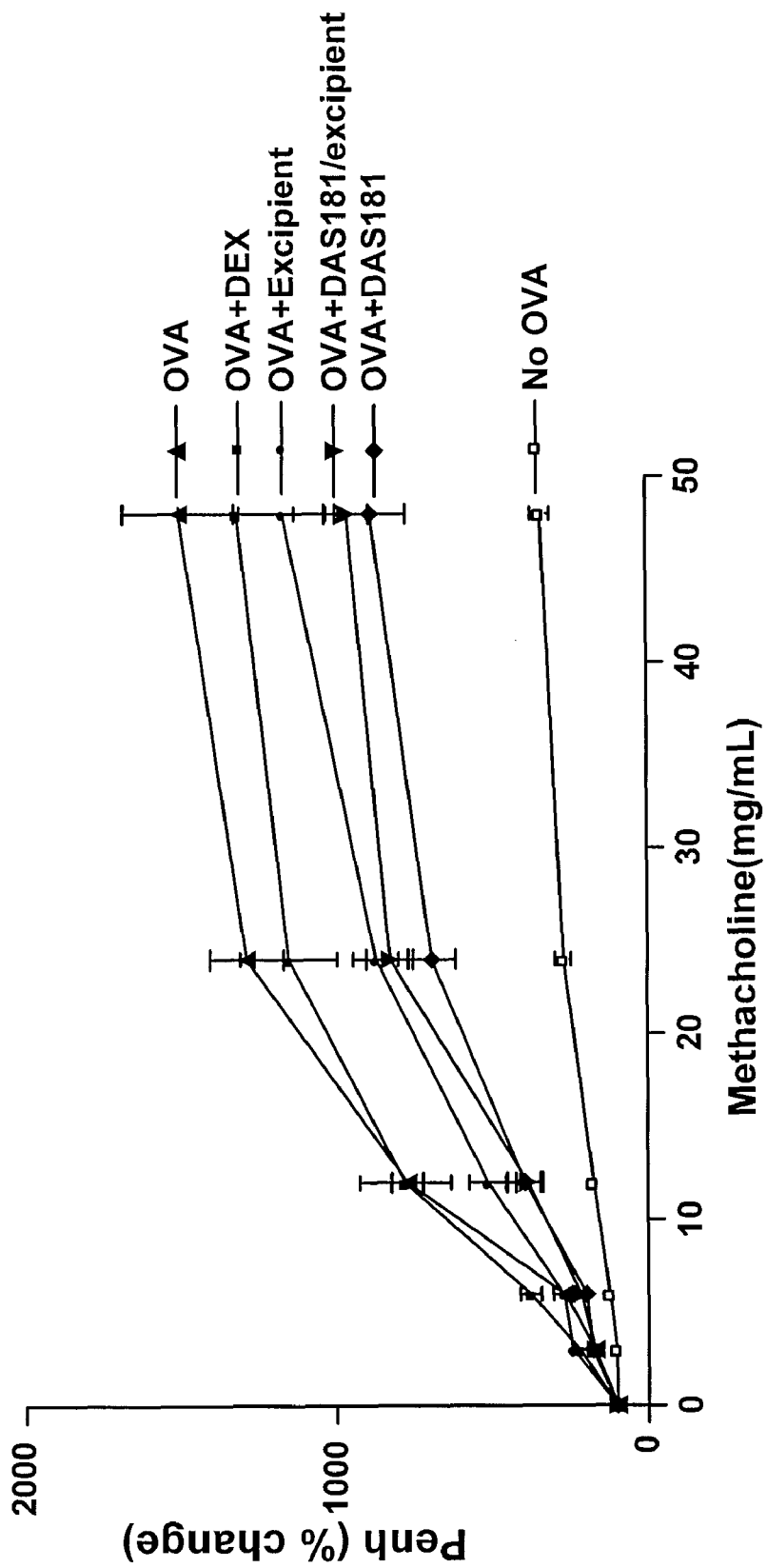

As shown in FIG. 16, measurement of Penh at 48 mg/ml Mch provides the largest difference between positive and negative controls (no OVA vs OVA) and is why this dose of Mch is used to assess the effect of an intervention such as DAS181.

b) Blood Eosinophils

Figure 17:
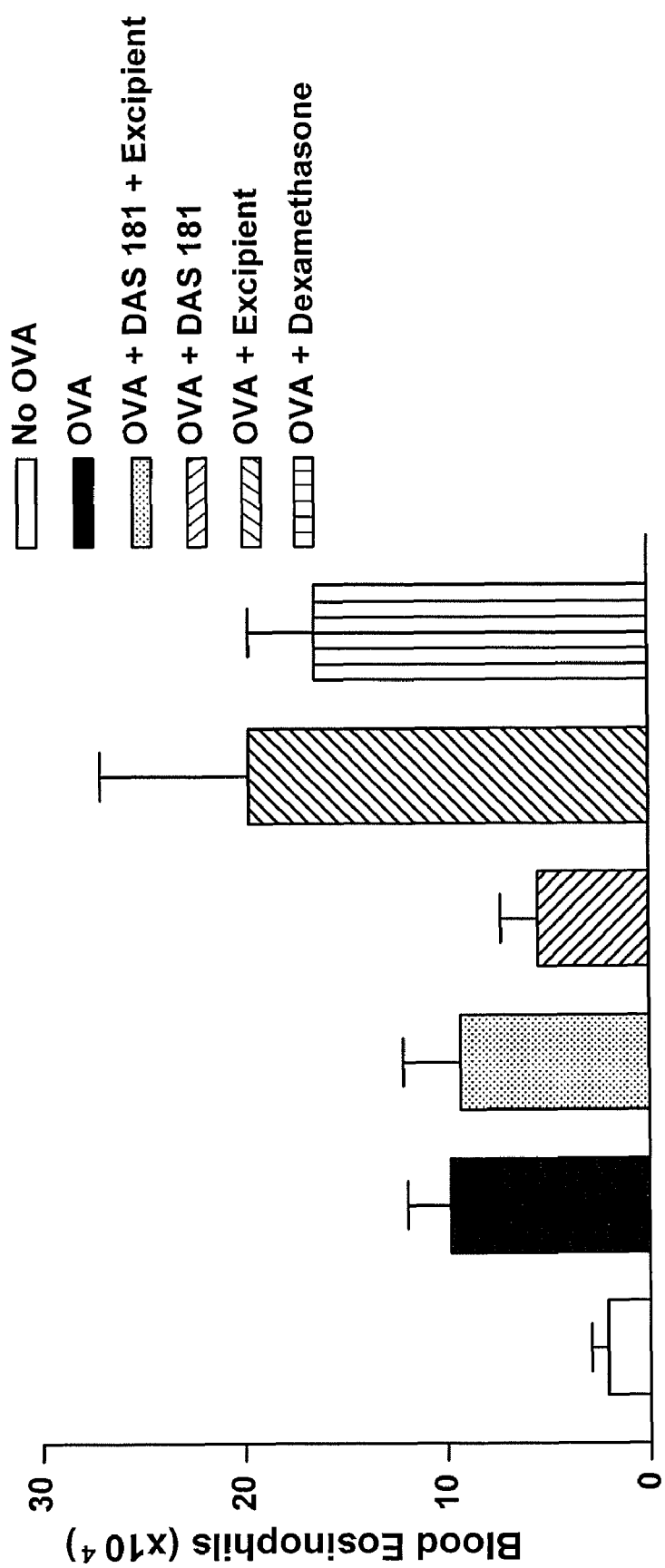

As shown in FIG. 17, OVA challenge induced a significant increase in blood eosinophils (OVA vs no OVA; p<0.0005).

DAS181 significantly reduced blood eosinophils (OVA vs OVA+DAS, p=0.04)

c) PAS Staining for Lung Mucus

Figure 18:
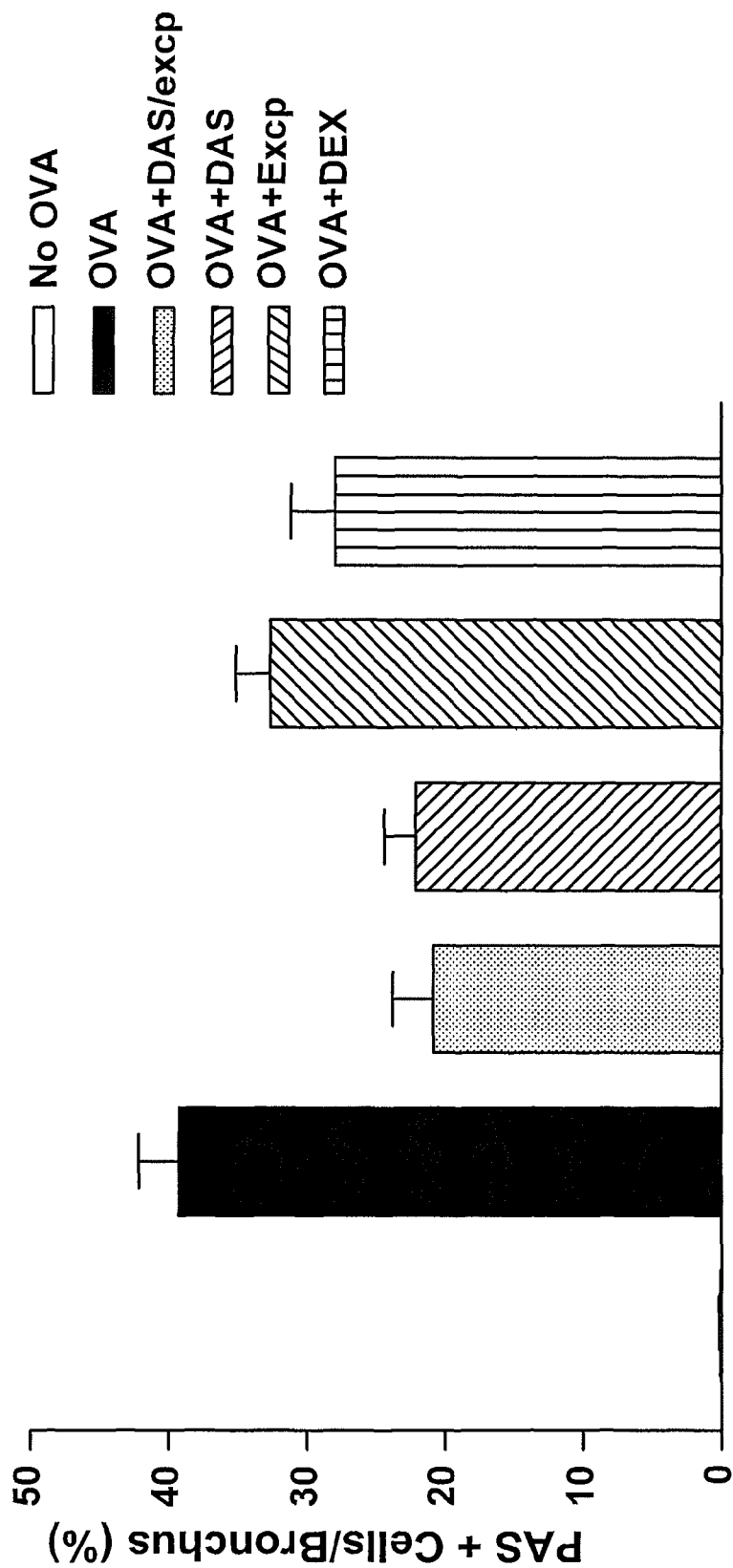
Figure 19:
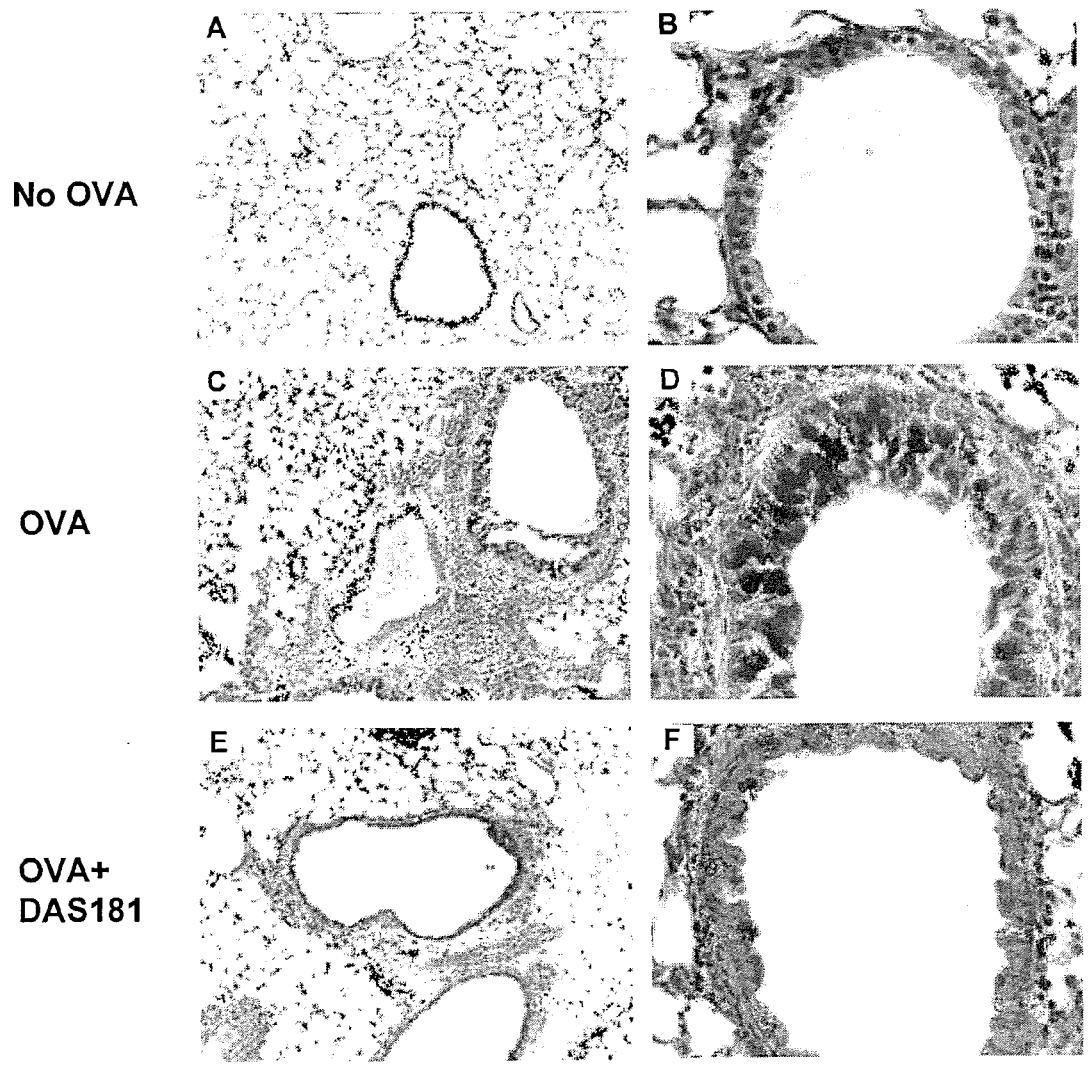

As shown in FIGS. 18-19A-F, OVA challenge induced a significant increase in the % of airway epithelium staining positive for PAS (OVA vs no OVA; p<0.0001).

OVA challenged mice pre-treated with DAS181+excipient had a significant reduction in PAS staining compared to OVA challenged mice (OVA vs OVA+DAS181+excipient; p<0.0001).

OVA challenged mice pre-treated with DAS181 had a statistically significant reduction in PAS staining compared to OVA challenged mice (OVA vs OVA+DAS181; p<0.0001).

Effect on Mucus

DAS181 with excipient as well as DAS181 alone significantly reduced PAS staining showing that there is an inhibitory effect of DAS181 on PAS staining. This shows that DAS181 with excipient or DAS181 alone reduces mucus in the respiratory tract.

d) MBP Immunostaining of Lungs

Figure 20:
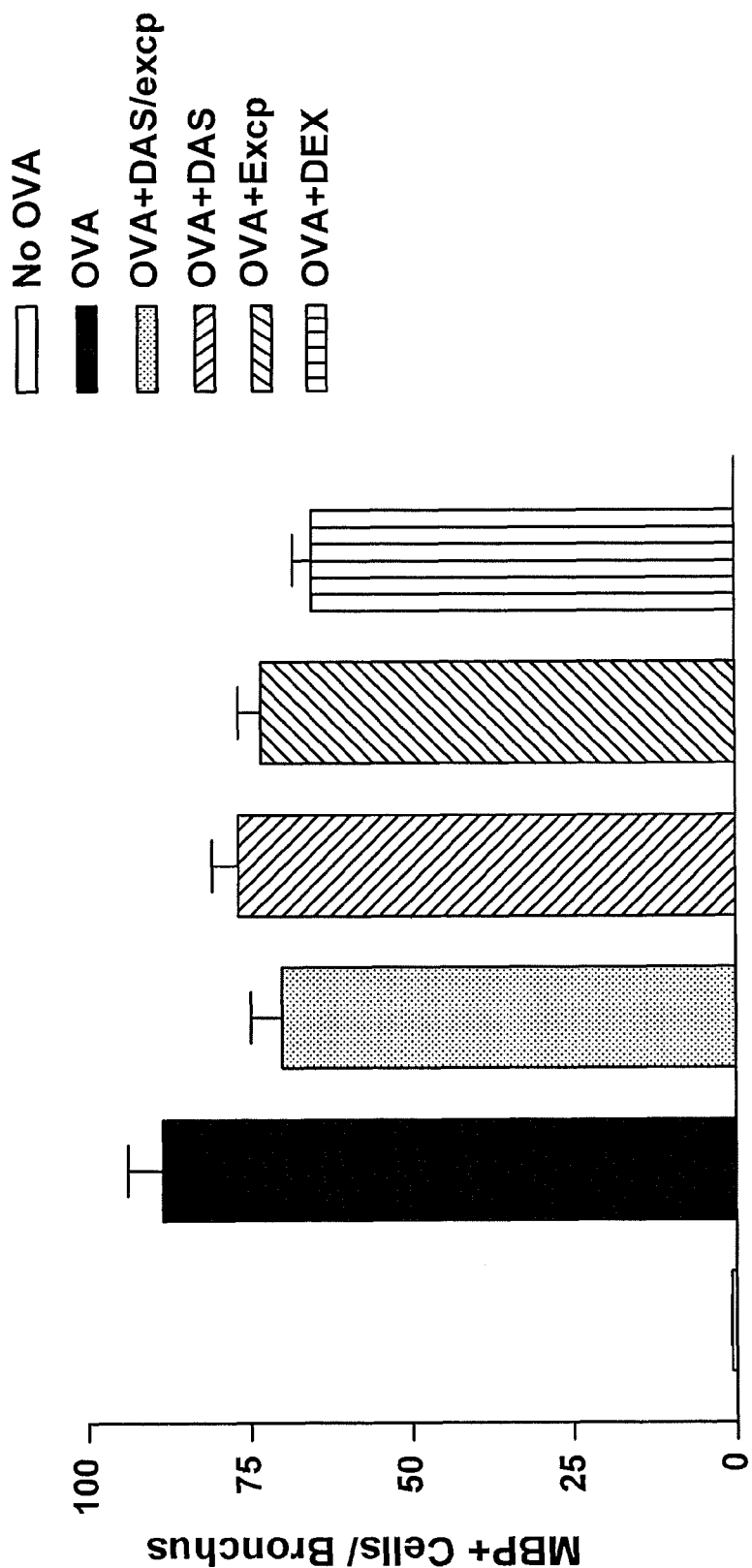

As shown in FIG. 20, OVA challenge induced a significant increase in the number of peribronchial MBP+eosinophils (OVA vs no OVA; p<0.0001).

OVA challenged mice pre-treated with DAS181+excipient had a significant reduction in the number of peribronchial MBP+eosinophils compared to OVA challenged mice (OVA vs OVA+DAS181+excipient; p=0.02).

Example 3

Reduced Airway Resistance in Naïve Mice Treated Intranasally with Low Doses of DAS181 (Methacholine Challenged)

The objective of the study was to test the effect of different dose levels of DAS181 on muscarinic receptor mediated airway resistance in naive mice. BALB/c mice (N=4) were treated intranasally with PBS or DAS181 at 0.06, 0.1 or 0.6 mg/kg once daily for three days. Eight hours post the final treatment animals were challenged with increasing doses of muscarinic receptor agonist Methacholine (Mch). Airway responsiveness was assessed using whole body plethysmography. Changes in airway resistance were expressed as the enhanced pause (Penh), a dimensionless value that represents a function of the proportion of maximal expiratory to maximal inspiratory box pressure signals and of the timing of expiration. Mice were exposed to nebulized PBS and subsequently to increasing concentrations of nebulized MCh (12, 24, 48 mg/ml Mch) for 2 min in PBS. Recordings were performed for 3 min following each exposure. The obtained Penh values were averaged and expressed as the percentage of baseline following PBS exposure.

Results: 24 and 48 mg/ml of the muscarinic receptor agonist methacholine increased airway resistance above baseline. All animals treated with DAS181 had significantly reduced airway resistance at 48 mg/ml of Mch (Fig). No difference was observed between the different dose groups.

Figure 21A:
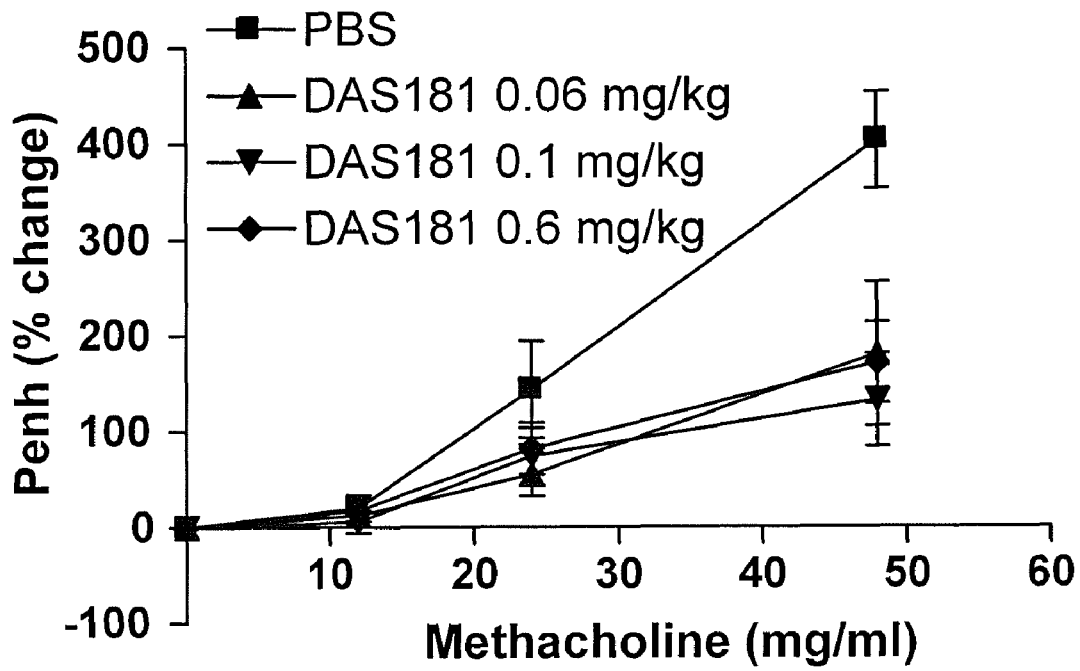
Figure 21B:
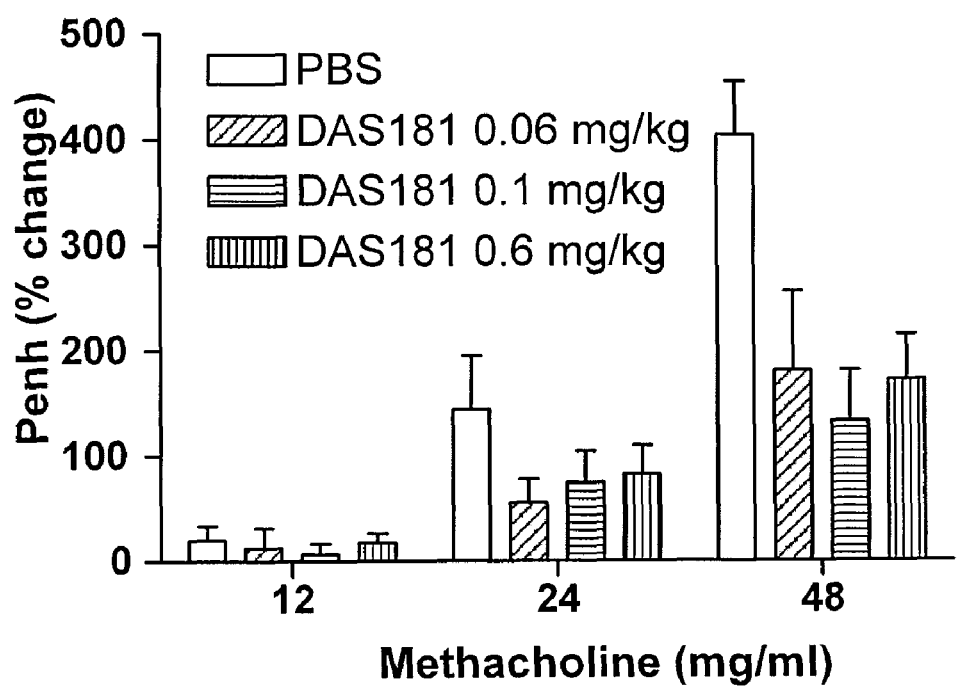

Conclusions: Consistent with previous data, intranasal treatment with DAS181 reduced bronchoconstriction in response to the muscarinic receptor agonist Mch, further supporting the hypothesis that DAS181 dependent desialylation causes a reduction in muscarinic receptor signaling. Surprisingly, the two higher dose levels did not exert any greater effect than the lowest dose, suggesting that a dosage level as low as 0.06 mg/kg of intranasal DAS181 is sufficient to desialylate muscarinic receptors resulting in reduced airway responsiveness to muscarinic receptor agonists, and thus potentially resulting in reducing inflammation, allergies or acetylcholine-associated responses, such as bronchoconstriction, asthma, and mucus overproduction. These results are depicted in FIGS. 21A and 21B.

Example 4

Reduced Airway Resistance in Naïve Mice Treated Intranasally with a Low Dose of DAS181 (Methacholine Challenged)

The objective of the study was to test the effect of a 0.6 mg/kg once daily dose of DAS181 on muscarinic receptor mediated airway resistance in naive mice. BALB/c mice (N=4) were treated intranasally with PBS or DAS181 at 0.6 mg/kg once daily for three days. Eight hours post the final treatment animals were challenged with increasing doses of muscarinic receptor agonist Methacholine (Mch). Airway responsiveness was assessed using whole body plethysmography. Changes in airway resistance were expressed as the enhanced pause (Penh), a dimensionless value that represents a function of the proportion of maximal expiratory to maximal inspiratory box pressure signals and of the timing of expiration. Mice were exposed to nebulized PBS and subsequently to increasing concentrations of nebulized MCh (3, 6, 12, 24, 48 mg/ml Mch) for 2 min in PBS. Recordings were performed for 3 min following each exposure. The obtained Penh values were averaged and expressed as the percentage of baseline following PBS exposure.

Results: 3, 6, 12, 24 and 48 mg/ml of the muscarinic receptor agonist methacholine increased airway resistance above baseline in PBS treated animals, and 12, 24 and 48 mg/ml of methacholine increased airway resistance above baseline in DAS181 treated animals, while 3 and 6 mg/ml of methacholine did not increase airway resistance above baseline in DAS181 treated animals. All animals treated with DAS181 had significantly reduced airway resistance at 6, 12, 24 and 48 mg/ml of Mch compared to the control.

Figure 22:
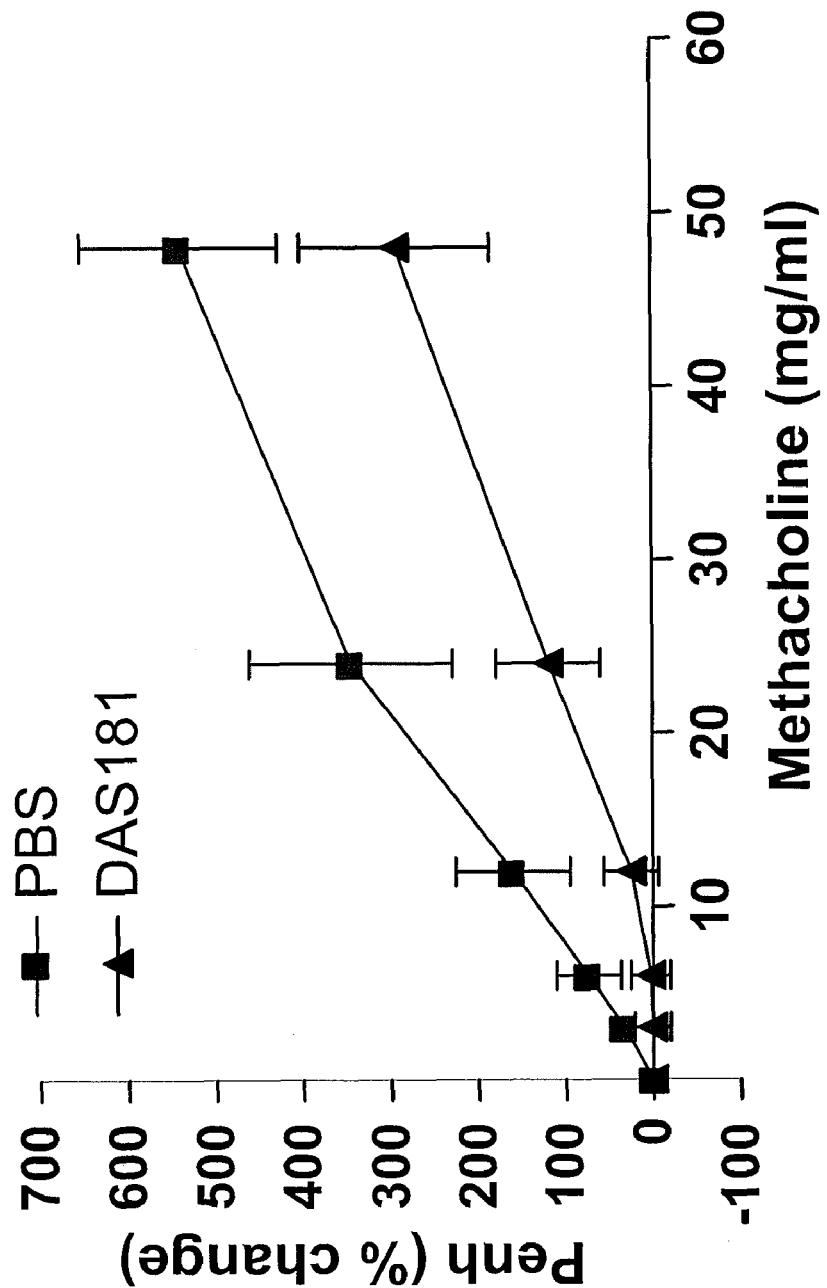

Conclusions: Consistent with previous data, intranasal treatment with DAS181 reduced bronchoconstriction in response to the muscarinic receptor agonist Mch, further supporting the hypothesis that DAS181 dependent desialylation causes a reduction in muscarinic receptor signaling. These results are depicted in FIG. 22.

Example 5

Reduced Airway Resistance in Naïve Mice Treated Intranasally with DAS181 (Carbachol Challenged)

The objective of the study was to test the effect of a 0.6 mg/kg once daily dose of DAS181 on muscarinic receptor mediated airway resistance in naive mice. BALB/c mice (N=4) were treated intranasally with PBS or DAS181 at 0.6 mg/kg once daily for three days. Eight hours post the final treatment animals were challenged with increasing doses of muscarinic receptor agonist carbachol. Airway responsiveness was assessed using whole body plethysmography. Changes in airway resistance were expressed as the enhanced pause (Penh), a dimensionless value that represents a function of the proportion of maximal expiratory to maximal inspiratory box pressure signals and of the timing of expiration. Mice were exposed to nebulized PBS and subsequently to increasing concentrations of nebulized Carbachol (1.25, 2.5, 5, 10, 20 mg/ml carbachol) for 2 min in PBS. Recordings were performed for 3 min following each exposure. The obtained Penh values were averaged and expressed as the percentage of baseline following PBS exposure.

Results: 5, 10, and 20 mg/ml of the muscarinic receptor agonist carbachol increased airway resistance above baseline in both PBS treated and DAS181 animals. All animals treated with DAS181 had significantly reduced airway resistance at 5, 10, and 20 mg/ml of carbachol.

Figure 23:
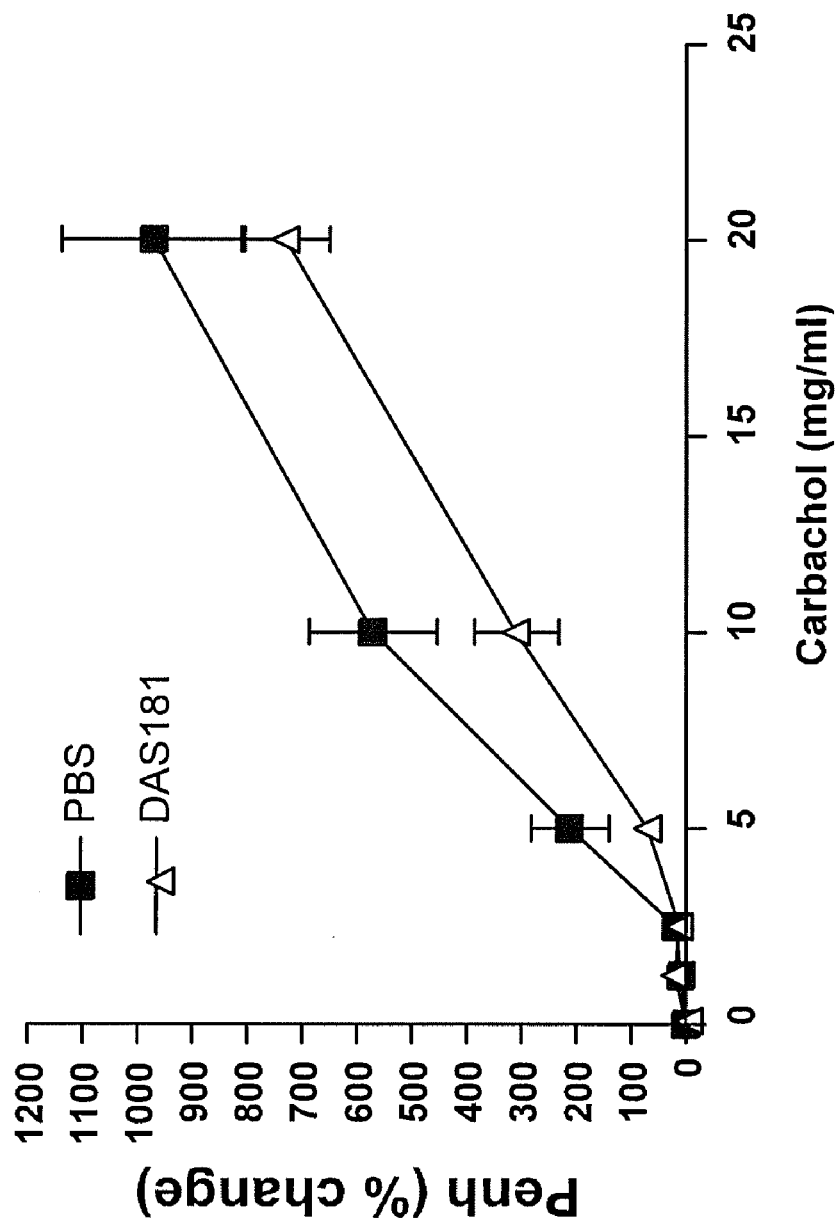

Conclusions: Consistent with previous data, intranasal treatment with DAS181 reduced bronchoconstriction in response to the muscarinic receptor agonist carbachol, further supporting the hypothesis that DAS181 dependent desialylation causes a reduction in muscarinic receptor signaling. These results are depicted in FIG. 23.

Example 6

Airway Resistance in Naïve Mice Treated Intranasally with a Low Dose of DAS185 (Methacholine Challenged)

The objective of the study was to test the effect of a 0.6 mg/kg once daily dose of DAS185 on muscarinic receptor mediated airway resistance in naive mice. DAS185 is an enzymatically inactive version of DAS181, in which a mutation in the sialidase portion renders the sialidase inactive. BALB/c mice (N=4) were treated intranasally with PBS or DAS185 at 0.6 mg/kg once daily for three days. Eight hours post the final treatment animals were challenged with increasing doses of muscarinic receptor agonist Methacholine (Mch). Airway responsiveness was assessed using whole body plethysmography. Changes in airway resistance were expressed as the enhanced pause (Penh), a dimensionless value that represents a function of the proportion of maximal expiratory to maximal inspiratory box pressure signals and of the timing of expiration. Mice were exposed to nebulized PBS and subsequently to increasing concentrations of nebulized MCh (3, 6, 12, 24, 48 mg/ml Mch) for 2 min in PBS. Recordings were performed for 3 min following each exposure. The obtained Penh values were averaged and expressed as the percentage of baseline following PBS exposure.

Results: There was no difference in airway resistance in response to the Mch challenge between the DAS185 treated and PBS treated animals.

Figure 24:
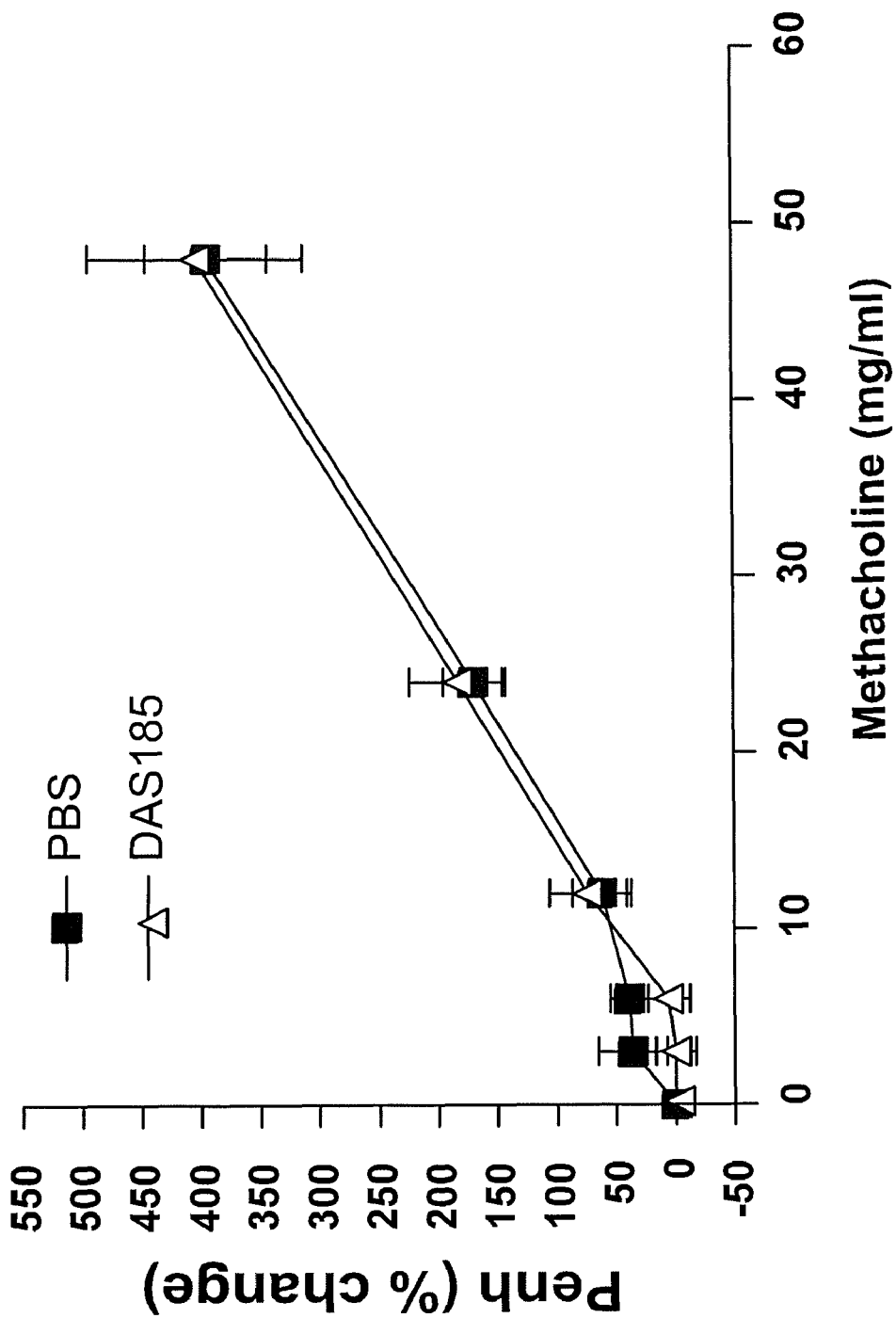
Figure 25:
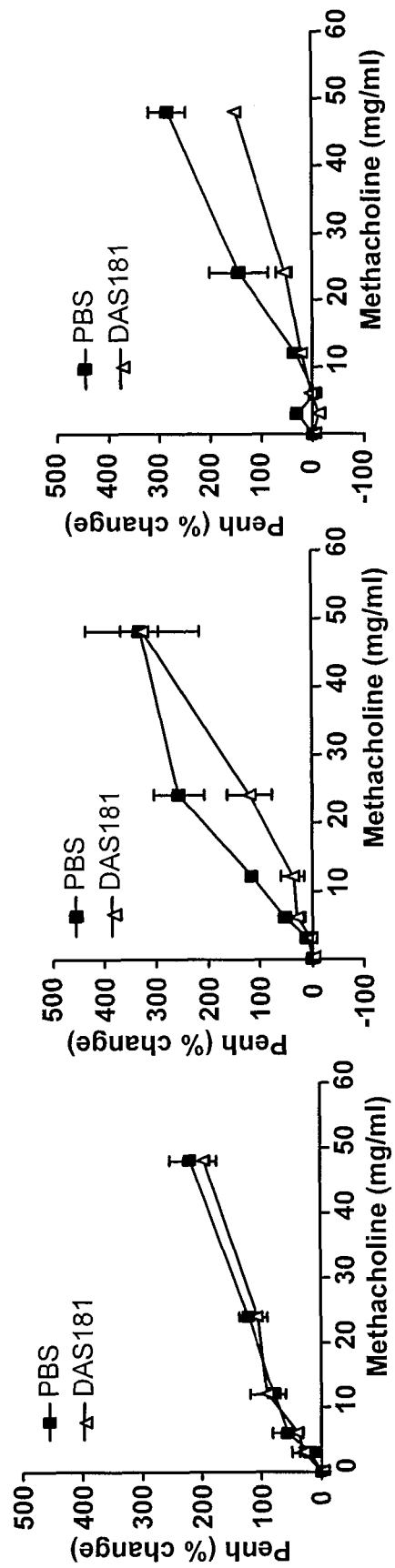
Figure 26:
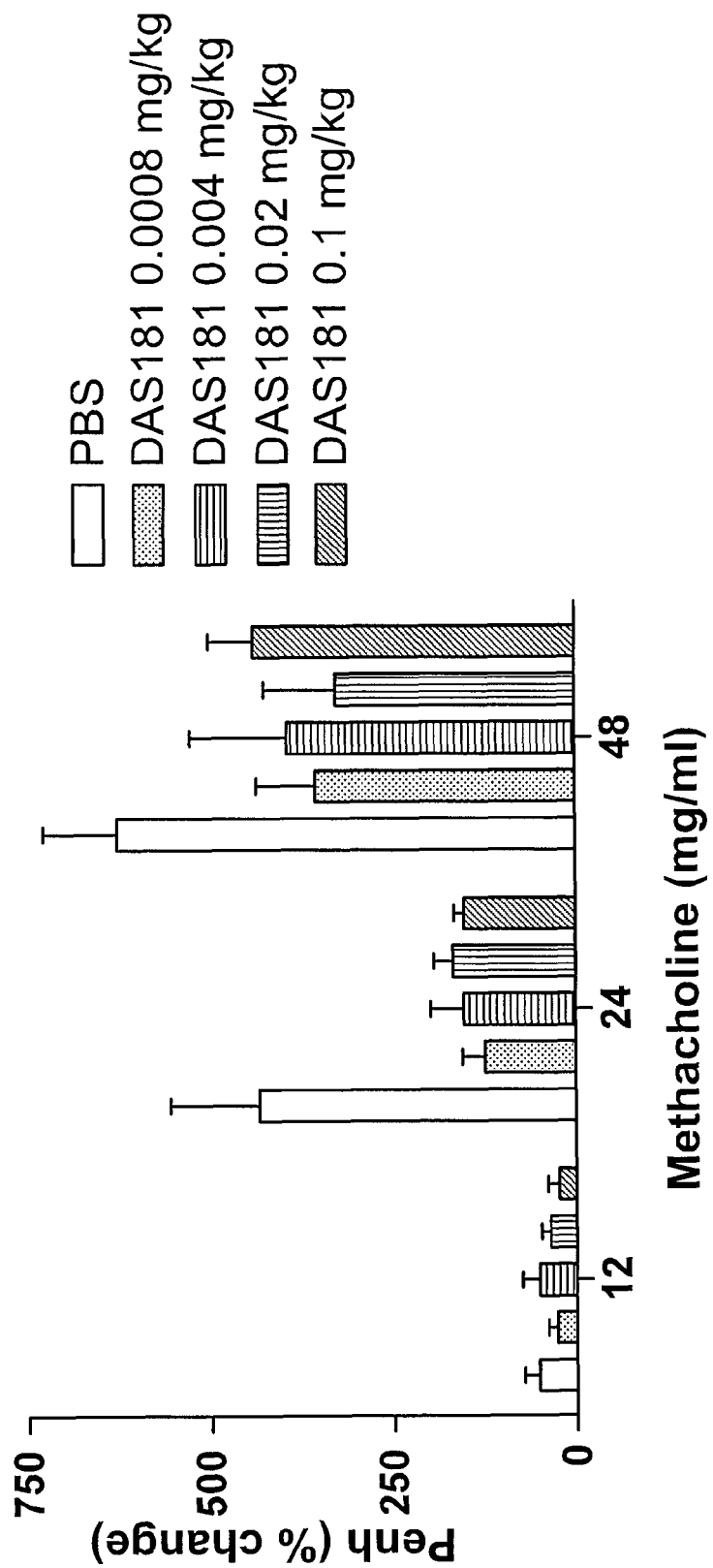

Conclusions: Whereas there was a difference in airway resistance between DAS181 and PBS treated animals in example 4 above, there was no difference when DAS181 was replaced with enzymatically inactive DAS185. This experiment shows that reduction in airway resistance in response to DAS181 is sialidase dependent. These results are depicted in FIG. 24.

Example 7

Time-Course of DAS181 Mediated Reduction of Airway Resistance (Methacholine Challenged)

The objective of the study was to test the effect of a 0.6 mg/kg once daily dose of DAS181 for one, two or three days on muscarinic receptor mediated airway resistance in naive mice. BALB/c mice (N=4) were treated intranasally with PBS or DAS181 at 0.6 mg/kg once daily for one, two or three days. Eight hours post the final treatment animals were challenged with increasing doses of muscarinic receptor agonist Methacholine (Mch). Airway responsiveness was assessed using whole body plethysmography. Changes in airway resistance were expressed as the enhanced pause (Penh), a dimensionless value that represents a function of the proportion of maximal expiratory to maximal inspiratory box pressure signals and of the timing of expiration. Mice were exposed to nebulized PBS and subsequently to increasing concentrations of nebulized MCh (3, 6, 12, 24, 48 mg/ml Mch) for 2 min in PBS. Recordings were performed for 3 min following each exposure. The obtained Penh values were averaged and expressed as the percentage of baseline following PBS exposure.

Results: For one day of treatment, there was no difference in airway resistance in response to the Mch challenge between the DAS181 treated and PBS treated animals. For two days of treatment, DAS181 appears to reduce airway resistance relative to PBS at 12 and 24 mg/ml methacholine, but not at 3, 6 and 48 mg/ml of methacholine. At three days of treatment, DAS181 had significantly reduced airway resistance at 24 and 48 mg/ml of Mch.

Conclusions: Consistent with previous data, there was a difference in airway resistance between DAS181 and PBS treated animals on day 3. There was no difference when following one treatment dose, and partial reduction following two days of treatment with DAS181. This experiment shows that 2-3 days of treatment is optimal to achieve a reduction in airway resistance. These results are depicted in FIG. 25.

Example 8

Reduced Airway Resistance in Naïve Mice Treated Intranasally with Very Low Doses of DAS181 (Methacholine Challenged)

The objective of the study was to test the effect of different low-dose levels of DAS181 on muscarinic receptor mediated airway resistance in naive mice. BALB/c mice (N=4) were treated intranasally with PBS or DAS181 at 0.0008, 0.004, 0.02, or 0.1 mg/kg once daily for three days. Eight hours post the final treatment animals were challenged with increasing doses of muscarinic receptor agonist Methacholine (Mch). Airway responsiveness was assessed using whole body plethysmography. Changes in airway resistance were expressed as the enhanced pause (Penh), a dimensionless value that represents a function of the proportion of maximal expiratory to maximal inspiratory box pressure signals and of the timing of expiration. Mice were exposed to nebulized PBS and subsequently to increasing concentrations of nebulized MCh (12, 24, 48 mg/ml Mch) for 2 min in PBS. Recordings were performed for 3 min following each exposure. The obtained Penh values were averaged and expressed as the percentage of baseline following PBS exposure.

Results: 24 and 48 mg/ml of the muscarinic receptor agonist methacholine increased airway resistance above baseline. All animals treated with DAS181 had significantly reduced airway resistance at 24 and 48 mg/ml of Mch. No difference was observed between the different dose groups of DAS181.

Conclusions: Intranasal treatment with very low doses of DAS181 reduced bronchoconstriction in response to the muscarinic receptor agonist Mch, further supporting the hypothesis that DAS181 dependent desialylation causes a reduction in muscarinic receptor signaling even at very low doses of DAS181. This experiment shows that dosage levels as low as 0.0008 mg/kg of intranasal DAS181 is sufficient to desialylate muscarinic receptors resulting in reduced airway responsiveness to muscarinic receptor agonists, and thus potentially resulting in reducing inflammation, allergies or acetylcholine-associated responses, such as bronchoconstriction, asthma, and mucus overproduction. These results are depicted in FIG. 26.

Example 9

The Reduced Airway Resistance in Naïve Mice Treated Intranasally with DAS181 is Dose-Dependent (Methacholine Challenged)

The objective of the study was to test the effect of different dose levels of DAS181 on muscarinic receptor mediated airway resistance in naive mice. BALB/c mice (N=4) were treated intranasally with PBS or DAS181 at 10 ng/kg, 0.1 μg/kg, 1 μg/kg, 10 μg/kg or 0.1 mg/kg once daily for three days followed by increasing doses of muscarinic receptor agonist methacholine (Mch). Airway responsiveness was assessed using whole body plethysmography. Changes in airway resistance were expressed as the enhanced pause (Penh), a dimensionless value that represents a function of the proportion of maximal expiratory to maximal inspiratory box pressure signals and of the timing of expiration. Mice were exposed to nebulized PBS and subsequently to increasing concentrations of nebulized MCh (12, 24, 48 mg/ml Mch) for 2 min in PBS. Recordings were performed for 3 min following each exposure. The obtained Penh values were averaged and expressed as the percentage of baseline following PBS exposure.

Results: 24 mg/ml and higher concentrations of the muscarinic receptor agonist methacholine increased airway resistance above baseline. The airway responsiveness was assessed 8 hours post-treatment on Day 3. All animals treated with DAS181 showed reduced airway resistance at 24 mg/ml of Mch, with average percentage change Penh values (representing increase in airway resistance over baseline) as follows:

Control (PBS): 550-560%

10 ng/kg DAS181: 525-530%

0.1 μg/kg DAS181: 450%

1 μg/kg DAS181: 525%

10 μg/kg DAS181: 225%

0.1 mg/kg DAS181: 200%

As seen from the above results, dose levels of 0.01 or 0.1 mg/kg of DAS181 significantly reduced airway resistance in response to Mch.

Conclusion: The results demonstrate that reduced airway resistance in response to intranasal treatment with DAS181 is dose-dependent.

Example 10

Effect of DAS181 on M2 and M3 Muscarinic Receptor Signaling In Vitro

The objective of the study was to assess muscarinic receptor desialylation as a potential mechanism for airway protection, using an in vitro model. Human chem-1 cells (Millipore) stably transfected with M2 or M3 muscarinic receptor were treated with 0.4, 2 or 10 μM of DAS181 for 30 min at 37° C. prior to the addition of a receptor agonist (acetylcholine; ACh). Receptor signaling was determined using a fluorescence reporter for intracellular calcium.

Results: At all doses of DAS181 tested, treatment of human chem-1 cells with DAS181 increased the potency of agonist-mediated M2 receptor signaling and decreased the potency of agonist-mediated M3 receptor signaling. The results are shown below:

A. M2 Receptor

| Treatment | Predicted EC50 Potency Value (M) |
|---|---|
| ACh alone (no DAS181) | 390 nM |
| ACh + 10 μM DAS181 | 140 nM |
| ACh + 2 μM DAS181 | 130 nM |
| ACh + 0.4 μM DAS181 | 140 nM |

B. M3 Receptor

| Treatment | Predicted EC50 Potency Value (M) |
|---|---|
| ACh alone (no DAS181) | 6.3 nM |
| ACh + 10 μM DAS181 | 270 nM |
| ACh + 2 μM DAS181 | 51 nM |
| ACh + 0.4 μM DAS181 | 110 nM |

Conclusion: The results demonstrate that DAS181 increases signaling through the M2 muscarinic receptor and decreases signaling through the M3 muscarinic receptor. Thus, the DAS181-mediated responses could be indicative of positive allosteric modulation of the M2, and either antagonist or negative modulation M3. Desialylation may offer airway protection by reducing the stimulatory signal as well as enhancing the inhibitory signal mediated by muscarinic receptors.

Example 11

Therapeutic Efficacy of DAS181 Microparticle Formulations against Parainfluenza

The efficacy of DAS181 was tested against parainfluenza virus (PIV), which is an acute respiratory infection. A 63 year old female patient tested positive for PIV on Jul. 14, 2010 and Jul. 21, 2010; shedding of the PIV antigen in nasal swabs and sputum samples collected from the patient on those days was detected by PCR.

The patient was treated on Jul. 23, 24 and 25, 2010 with one capsule (10 mg delivered dose) a day of a dry powder formulation of DAS181 whose components and wt/wt % in the composition are as follows: DAS181: 64.54-64.69%; Histidine free base: 4.32-4.60%; Histidine HCl: 5.85-6.27%; Trehalose: 9.06-9.68%; Magnesium sulfate: 4.66-5.84%; Calcium chloride: 0.19%; Sodium acetate: 0.04-0.05%; Acetic acid: 0.02%; Water: 10%; Isopropanol: trace amounts. Each capsule contained 13 mg of the dry powder in a type 3 clear HPMC capsule (Capsugel), giving a delivered dose of 10 mg. The patient was administered one capsule a day for three days (Jul. 23, Jul. 24 and Jul. 25, 2010) by inhalation. The patient tested positive for PIV on the day after completion of the treatment (July 26), and tested negative for PIV on the fifth day following treatment (Jul. 30, 2010). The results demonstrate the effectiveness of DAS181 against parainfluenza, i.e., a respiratory infection of the upper respiratory tract.

Example 12

Therapeutic Efficacy of DAS181 Microparticle Formulations Against Asthma

The efficacy of the DAS181 microparticle formulation used in Example 9 above was tested against asthma. A 20 year old male Caucasian asthma patient was tested for changes in airflow prior to and 1 hour after oral administration of a 10 mg delivered dose (13 mg capsule) of Formulation A, as measured by FEV1 (forced expiratory volume of air in 1 second). Prior to administration of the drug, the FEV1 of the patient was at 82% of the predicted normal lung function. One hour after administration of the drug, the FEV1 of the patient indicated a clinically significant improvement in lung function, with a 10% increase in value to 92%. The results demonstrate that a DAS181 formulation can be effective against asthma, i.e., a non-infectious respiratory disorder affecting the central to upper respiratory tract.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method of limiting an increase in the quantity of mucus in the respiratory tract of a subject above a baseline level of mucus in the subject's respiratory tract, comprising:
    determining a baseline level of mucus in the subject's respiratory tract; and
    administering to the subject a compound or composition containing a therapeutically effective amount of a fusion protein, wherein
    the fusion protein comprises at least one catalytic domain of a sialidase, wherein the catalytic domain of the sialidase comprises the sequence of amino acids extending from amino acid 274 to amino acid 666 of SEQ ID NO:12, inclusive, and at least one anchoring domain, wherein the anchoring domain is a glycosaminoglycan (GAG) binding domain of human amphiregulin comprising the amino acid sequence of SEQ ID NO:7, wherein the therapeutically effective amount comprises an amount of the fusion protein that limits an increase in the quantity of mucus in the respiratory tract of the subject above the baseline level.

2. The method of claim 1, wherein the composition further comprises one or more additional compounds.

3. The method of claim 2, wherein the one or more additional compounds comprises $MgSO_4$.

4. The method of claim 2, wherein the one or more additional compounds comprises $CaCl_2$.

5. The method of claim 2, wherein the one or more additional compounds comprises Histidine.

6. The method of claim 2, wherein the one or more additional compounds comprises Histidine-HCl.

7. The method of claim 2, wherein the one or more additional compounds comprises Trehalose.

8. The method of claim 2, wherein the one or more additional compounds comprises $MgSO_4$, $CaCl_2$, Histidine, Histine-HCl and Trehalose.

9. The method of claim 1, wherein the compound or composition is formulated as a spray.

10. The method of claim 1, wherein the compound or composition is formulated as an inhalant.

11. The method of claim 1, wherein the compound or composition is formulated as a solution for injection.

12. The method of claim 1, wherein the compound or composition is formulated as a cream, salve, gel, or ointment.

13. The method of claim 1, wherein the compound or composition is formulated as a pill, tablet, lozenge, suspension, or solution that can be administered orally.

14. The method of claim 1, wherein said administration is by use of a nasal spray.

15. The method of claim 1, wherein said administration is by use of an inhaler.

16. The method of claim 1, wherein said administration is performed from once to four times a day.

17. The method of claim 1, wherein said administration is by topical application.

18. The method of claim 1, wherein said administration is by oral administration.

19. The method of claim 1, wherein said administration is by local or intravenous injection.

20. The method of claim 1, wherein the subject is human.

21. The method of claim 1, wherein the subject is a non-human animal.

22. The method of claim 1, wherein the subject has one or more of the following conditions: chronic obstructive pulmonary disease (COPD), bronchitis, bronchiectasis, cystic fibrosis (CF), vasculitis, mucus plugging, Wegener's granulomatosis, pneumonia, tuberculosis, cancer involving the lungs or the respiratory tract, Kartagener syndrome, Young's syndrome, chronic sinopulmonary infection, alpha 1-antitrypsin deficiency, primary immunodeficiency, acquired immune deficiency syndrome, opportunistic infection, an infectious state, a post infectious state, common cold, exercise induced hypersecretion of mucus, inflammatory bowel disease, ulcerative colitis, Crohn's disease, respiratory infection, respiratory obstruction, inhalation or aspiration of a toxic gas, pulmonary aspiration, or alcoholism.

23. The method of claim 1, wherein the fusion protein has the sequence set forth in SEQ ID NO:21.

24. A method of limiting an increase in the quantity of mucus in the respiratory tract of a subject above a baseline level of mucus in the subject's respiratory tract, comprising:
determining a baseline level of mucus in the subject's respiratory tract; and
administering to the subject a compound or composition containing a therapeutically effective amount of a fusion protein comprising a sialidase or an active portion thereof and an anchoring domain, wherein
the therapeutically effective amount comprises an amount of the fusion protein that limits an increase in the quantity of mucus in the respiratory tract of the subject above the baseline level.

25. The method of claim 24, wherein said sialidase or active portion thereof is substantially homologous to *Actinomyces viscosus* sialidase or its catalytic domain.

26. The method of claim 24, wherein said anchoring domain is a glycosaminoglycan (GAG) binding domain.

27. The method of claim 24, wherein the composition further comprises one or more additional compounds.

28. The method of claim 27, wherein the one or more additional compounds comprises $MgSO_4$.

29. The method of claim 27, wherein the one or more additional compounds comprises $CaCl_2$.

30. The method of claim 27, wherein the one or more additional compounds comprises Histidine.

31. The method of claim 27, wherein the one or more additional compounds comprises Histidine-HCl.

32. The method of claim 27, wherein the one or more additional compounds comprises Trehalose.

33. The method of claim 27, wherein the one or more additional compounds comprises $MgSO_4$, $CaCl_2$, Histidine, Histine-HCl and Trehalose.

34. The method of claim 24, wherein the compound or composition is formulated as a spray.

35. The method of claim 24, wherein the compound or composition is formulated as an inhalant.

36. The method of claim 24, wherein the compound or composition is formulated as a solution for injection.

37. The method of claim 24, wherein the compound or composition is formulated as a cream, salve, gel, or ointment.

38. The method of claim 24, wherein the compound or composition is formulated as a pill, tablet, lozenge, suspension, or solution that can be administered orally.

39. The method of claim 24, wherein said administration is by use of a nasal spray.

40. The method of claim 24, wherein said administration is by use of an inhaler.

41. The method of claim 24, wherein said administration is performed from once to four times a day.

42. The method of claim 24, wherein said administration is by topical application.

43. The method of claim 24, wherein said administration is by oral administration.

44. The method of claim 24, wherein said administration is by local or intravenous injection.

45. The method of claim 24, wherein the subject is a human.

46. The method of claim 24, wherein the subject is a non-human animal.

47. The method of claim 24, wherein the subject has one or more of the following conditions: chronic obstructive pulmonary disease (COPD), bronchitis, bronchiectasis, cystic fibrosis (CF), vasculitis, mucus plugging, Wegener's granulomatosis, pneumonia, tuberculosis, cancer involving the lungs or the respiratory tract, Kartagener syndrome, Young's syndrome, chronic sinopulmonary infection, alpha 1-antitrypsin deficiency, primary immunodeficiency, acquired immune deficiency syndrome, opportunistic infection, an infectious state, a post infectious state, common cold, exercise induced hypersecretion of mucus, inflammatory bowel disease, ulcerative colitis, Crohn's disease, respiratory infection, respiratory obstruction, inhalation or aspiration of a toxic gas, pulmonary aspiration, or alcoholism.

48. The method of claim 24, wherein the fusion protein has the sequence set forth in SEQ ID NO:21.

49. The method of any one of claims 1 and 24, further comprising selecting a subject for treatment.

50. The method of claim 49, wherein the subject is not infected with one or more of influenza virus, parainfluenza virus, and/or respiratory syncytial virus (RSV).

51. The method of claim 49, wherein the subject is infected with one or more of influenza virus, parainfluenza virus, and/or RSV.

52. The method of claim 49, wherein the subject has asthma.

53. The method of claim 50, wherein the subject has asthma.

54. The method of claim 51, wherein the subject further has asthma.

55. The method of claim 51, wherein the compound or composition comprises a protein or peptide having the sequence set forth in SEQ ID NO:21.

56. The method of claim 1 or 24, further comprising determining a second level of mucus in the subject's respiratory tract prior to administering to the subject the compound or composition.

57. The method of claim 56, further comprising continuing treatment until the level or increase in level of mucus in the subject's respiratory tract is decreased or limited in the second level of mucus compared to the baseline level of mucus in the subject's respiratory tract.

* * * * *

UNITED STATES PATENT AND TRADEMARK OFFICE
CERTIFICATE OF CORRECTION

PATENT NO. : 8,398,971 B2  
APPLICATION NO. : 12/940742  
DATED : March 19, 2013  
INVENTOR(S) : Fang Fang et al.

Page 1 of 1

It is certified that error appears in the above-identified patent and that said Letters Patent is hereby corrected as shown below:

On the Title Page

Item (57), Col. 2 (Abstract), line 2, delete "quanitity" and insert -- quantity --

Item (57), Col. 2 (Abstract), line 9, delete "quanitity" and insert -- quantity --

In the Specification

In Column 1, line 13, delete "61/322,063," and insert -- 61/332,063, --

In the Claims

In Column 112, line 55-56, claim 8, delete "Histine-HCl" and insert -- Histidine-HCl --

In Column 113, line 49, claim 26, after "claim 24," insert -- wherein the peptide comprises an anchoring domain, --

In Column 113, line 65, claim 33, delete "Histine-HCl" and insert -- Histidine-HCl --

Signed and Sealed this  
Fourth Day of June, 2013

Teresa Stanek Rea  
*Acting Director of the United States Patent and Trademark Office*

SEQUENCE LISTING

```
<160> NUMBER OF SEQ ID NOS: 39

<210> SEQ ID NO 1
<211> LENGTH: 58
<212> TYPE: PRT
<213> ORGANISM: Bos taurus

<400> SEQUENCE: 1

Arg Pro Asp Phe Cys Leu Glu Pro Pro Tyr Thr Gly Pro Cys Lys Ala
1               5                   10                  15

Arg Ile Ile Arg Tyr Phe Tyr Asn Ala Lys Ala Gly Leu Cys Gln Thr
            20                  25                  30

Phe Val Tyr Gly Gly Cys Arg Ala Lys Arg Asn Asn Phe Lys Ser Ala
        35                  40                  45

Glu Asp Cys Met Arg Thr Cys Gly Gly Ala
    50                  55

<210> SEQ ID NO 2
<211> LENGTH: 24
<212> TYPE: PRT
<213> ORGANISM: Homo sapiens

<400> SEQUENCE: 2

Asn Gly Arg Arg Ile Cys Leu Asp Leu Gln Ala Pro Leu Tyr Lys Lys
1               5                   10                  15

Ile Ile Lys Lys Leu Leu Glu Ser
            20
```

<210> SEQ ID NO 3
<211> LENGTH: 27
<212> TYPE: PRT
<213> ORGANISM: Homo sapiens

<400> SEQUENCE: 3

Gly Arg Glu Leu Cys Leu Asp Pro Lys Glu Asn Trp Val Gln Arg Val
1               5                   10                  15

Val Glu Lys Phe Leu Lys Arg Ala Glu Asn Ser
            20                  25

<210> SEQ ID NO 4
<211> LENGTH: 34
<212> TYPE: PRT
<213> ORGANISM: Homo sapiens

<400> SEQUENCE: 4

Gln Ile His Phe Phe Phe Ala Lys Leu Asn Cys Arg Leu Tyr Arg Lys
1               5                   10                  15

Ala Asn Lys Ser Ser Lys Leu Val Ser Ala Asn Arg Leu Phe Gly Asp
            20                  25                  30

Lys Ser

<210> SEQ ID NO 5
<211> LENGTH: 34
<212> TYPE: PRT
<213> ORGANISM: Homo sapiens

<400> SEQUENCE: 5

Glu Leu Arg Val Arg Leu Ala Ser His Leu Arg Lys Leu Arg Lys Arg
1               5                   10                  15

Leu Leu Arg Asp Ala Asp Asp Leu Gln Lys Arg Leu Ala Val Tyr Gln
            20                  25                  30

Ala Gly

<210> SEQ ID NO 6
<211> LENGTH: 12
<212> TYPE: PRT
<213> ORGANISM: Homo sapiens

<400> SEQUENCE: 6

Arg Arg Leu Arg Arg Met Glu Ser Glu Ser Glu Ser
1               5                   10

<210> SEQ ID NO 7
<211> LENGTH: 21
<212> TYPE: PRT
<213> ORGANISM: Homo sapiens

<400> SEQUENCE: 7

Lys Arg Lys Lys Lys Gly Gly Lys Asn Gly Lys Asn Arg Arg Asn Arg
1               5                   10                  15

Lys Lys Lys Asn Pro
            20

<210> SEQ ID NO 8
<211> LENGTH: 379
<212> TYPE: PRT
<213> ORGANISM: Homo sapiens

<400> SEQUENCE: 8

Met Ala Ser Leu Pro Val Leu Gln Lys Glu Ser Val Phe Gln Ser Gly

```
            1               5                  10                 15
Ala His Ala Tyr Arg Ile Pro Ala Leu Leu Tyr Leu Pro Gly Gln Gln
                    20                 25                 30

Ser Leu Leu Ala Phe Ala Glu Gln Arg Ala Ser Lys Lys Asp Glu His
                    35                 40                 45

Ala Glu Leu Ile Val Leu Arg Arg Gly Asp Tyr Asp Ala Pro Thr His
 50                     55                 60

Gln Val Gln Trp Gln Ala Gln Glu Val Val Ala Gln Ala Arg Leu Asp
 65                     70                 75                 80

Gly His Arg Ser Met Asn Pro Cys Pro Leu Tyr Asp Ala Gln Thr Gly
                    85                 90                 95

Thr Leu Phe Leu Phe Phe Ile Ala Ile Pro Gly Gln Val Thr Glu Gln
                   100                105                110

Gln Gln Leu Gln Thr Arg Ala Asn Val Thr Arg Leu Cys Gln Val Thr
               115                120                125

Ser Thr Asp His Gly Arg Thr Trp Ser Ser Pro Arg Asp Leu Thr Asp
           130                135                140

Ala Ala Ile Gly Pro Ala Tyr Arg Glu Trp Ser Thr Phe Ala Val Gly
145                150                155                160

Pro Gly His Cys Leu Gln Leu Asn Asp Arg Ala Arg Ser Leu Val Val
                   165                170                175

Pro Ala Tyr Ala Tyr Arg Lys Leu His Pro Ile Gln Arg Pro Ile Pro
                   180                185                190

Ser Ala Phe Cys Phe Leu Ser His Asp His Gly Arg Thr Trp Ala Arg
                   195                200                205

Gly His Phe Val Ala Gln Asp Thr Leu Glu Cys Gln Val Ala Glu Val
                   210                215                220

Glu Thr Gly Glu Gln Arg Val Val Thr Leu Asn Ala Arg Ser His Leu
225                230                235                240

Arg Ala Arg Val Gln Ala Gln Ser Thr Asn Asp Gly Leu Asp Phe Gln
                   245                250                255

Glu Ser Gln Leu Val Lys Lys Leu Val Glu Pro Pro Gln Gly Cys
                   260                265                270

Gln Gly Ser Val Ile Ser Phe Pro Ser Pro Arg Ser Gly Pro Gly Ser
                   275                280                285

Pro Gln Trp Leu Leu Tyr Thr His Pro Thr His Ser Trp Gln Arg Ala
       290                295                300

Asp Leu Gly Ala Tyr Leu Asn Pro Arg Pro Pro Ala Pro Glu Ala Trp
305                310                315                320

Ser Glu Pro Val Leu Leu Ala Lys Gly Ser Cys Ala Tyr Ser Asp Leu
                   325                330                335

Gln Ser Met Gly Thr Gly Pro Asp Gly Ser Pro Leu Phe Gly Cys Leu
                   340                345                350

Tyr Glu Ala Asn Asp Tyr Glu Glu Ile Val Phe Leu Met Phe Thr Leu
                   355                360                365

Lys Gln Ala Phe Pro Ala Glu Tyr Leu Pro Gln
    370                375
```

<210> SEQ ID NO 9
<211> LENGTH: 424
<212> TYPE: PRT
<213> ORGANISM: Homo sapiens

<400> SEQUENCE: 9

Leu Ala Gly Gly Ser Val Arg Trp Gly Ala Leu His Val Leu Gly Thr

-continued

```
         1               5                  10                 15
Ala Ala Leu Ala Glu His Arg Ser Met Asn Pro Cys Pro Val His Asp
                20                  25                  30

Ala Gly Thr Gly Thr Val Phe Leu Phe Phe Ile Ala Val Leu Gly His
                35                  40                  45

Thr Pro Glu Ala Val Gln Ile Ala Thr Gly Arg Asn Ala Ala Arg Leu
        50                  55                  60

Cys Cys Val Ala Ser Arg Asp Ala Gly Leu Ser Trp Gly Ser Ala Arg
65                  70                  75                  80

Asp Leu Thr Glu Glu Ala Ile Gly Gly Ala Val Gln Asp Trp Ala Thr
                85                  90                  95

Phe Ala Val Gly Pro Gly His Gly Val Gln Leu Pro Ser Gly Arg Leu
                100                 105                 110

Leu Val Pro Ala Tyr Thr Tyr Arg Val Asp Arg Leu Glu Cys Phe Gly
                115                 120                 125

Lys Ile Cys Arg Thr Ser Pro His Ser Phe Ala Phe Tyr Ser Asp Asp
                130                 135                 140

His Gly Arg Thr Trp Arg Cys Gly Gly Leu Val Pro Asn Leu Arg Ser
145                 150                 155                 160

Gly Glu Cys Gln Leu Ala Ala Val Asp Gly Gln Ala Gly Ser Phe
                165                 170                 175

Leu Tyr Cys Asn Ala Arg Ser Pro Leu Gly Ser Arg Val Gln Ala Leu
                180                 185                 190

Ser Thr Asp Glu Gly Thr Ser Phe Leu Pro Ala Glu Arg Val Ala Ser
                195                 200                 205

Leu Pro Glu Thr Ala Trp Gly Cys Gln Gly Ser Ile Val Gly Phe Pro
        210                 215                 220

Ala Pro Ala Pro Asn Arg Pro Arg Asp Asp Ser Trp Ser Val Gly Pro
225                 230                 235                 240

Arg Ser Pro Leu Gln Pro Pro Leu Leu Gly Pro Gly Val His Glu Pro
                245                 250                 255

Pro Glu Glu Ala Ala Val Asp Pro Arg Gly Gly Gln Val Pro Gly Gly
                260                 265                 270

Pro Phe Ser Arg Leu Gln Pro Arg Gly Asp Gly Pro Arg Gln Pro Gly
                275                 280                 285

Pro Arg Pro Gly Val Ser Gly Asp Val Gly Ser Trp Thr Leu Ala Leu
                290                 295                 300

Pro Met Pro Phe Ala Ala Pro Pro Gln Ser Pro Thr Trp Leu Leu Tyr
305                 310                 315                 320

Ser His Pro Val Gly Arg Arg Ala Arg Leu His Met Gly Ile Arg Leu
                325                 330                 335

Ser Gln Ser Pro Leu Asp Pro Arg Ser Trp Thr Glu Pro Trp Val Ile
                340                 345                 350

Tyr Glu Gly Pro Ser Gly Tyr Ser Asp Leu Ala Ser Ile Gly Pro Ala
                355                 360                 365

Pro Glu Gly Gly Leu Val Phe Ala Cys Leu Tyr Glu Ser Gly Ala Arg
                370                 375                 380

Thr Ser Tyr Asp Glu Ile Ser Phe Cys Thr Phe Ser Leu Arg Glu Val
385                 390                 395                 400

Leu Glu Asn Val Pro Ala Ser Pro Lys Pro Asn Leu Gly Asp Lys
                405                 410                 415

Pro Arg Gly Cys Cys Trp Pro Ser
                420
```

```
<210> SEQ ID NO 10
<211> LENGTH: 5
<212> TYPE: PRT
<213> ORGANISM: Artificial Sequence
<220> FEATURE:
<223> OTHER INFORMATION: Synthetic Construct

<400> SEQUENCE: 10

Gly Gly Gly Gly Ser
 1               5

<210> SEQ ID NO 11
<211> LENGTH: 2706
<212> TYPE: DNA
<213> ORGANISM: Actinomyces viscosus

<400> SEQUENCE: 11
atgacatcgc atagtccttt ctcccggagg cgcctgccgg ccctcctggg ctccctgcca      60
ctggccgcca ccggcctgat cgccgccgca ccccgcgcg acgccgtccc cacgtctgac     120
ggcctggccg acgtcaccat cacgcaggtg aacgcgcccg cggacggcct ctactccgtc     180
ggcgatgtca tgaccttcaa catcaccctg accaacacca cgcgcgaggc ccactcctac     240
gccccggcct cgacgaacct gtccgggaac gtctccaagt gccggtggcg caacgtcccg     300
gccgggacga ccaagaccga ctgcaccggc ctggccacgc acacggtgac cgccgaggac     360
ctcaaggccg gtggcttcac cccgcagatc gcctacgagg tcaaggccgt ggagtacgcc     420
gggaaggccc tgagcacccc ggagacgatc aagggcgcga cgagcccagt caaggccaac     480
tcgctgcggg tcgagtcgat cacgccgtcg tcgagccagg agaactacaa gctgggcgac     540
accgtcagct acacggtgcg cgtgcgctcg gtgtcggaca agacgatcaa cgtcgccgcc     600
accgaatcct ccttcgacga cctgggccgc cagtgccact ggggcggcct caagccgggc     660
aagggcgccg tctacaactg caagccgctc acccacacga tcacgcaagc cgacgtcgac     720
gccggccgct ggacgccatc gatcaccctg acggccaccg aaccgacgg cgccaccctc     780 cagacgctca ccgccaccgg caacccgatc aacgtcgtcg cgaccacccc gcaggccacg     840
cccgcaccgg cgcccgacgc gagcacggag ctgccggcct caatgagcca ggcccagcac     900
ctggccgcca acacgccac cgacaactac cgcatcccgg cgatcaccac cgcccccaat     960
ggggacctgc tcatctccta cgacgagcgc ccgaaggaca acgcaacgg cggcagcgac    1020 gcccccaacc cgaaccacat cgtccagcgc cgctccaccg acggcggcaa gacctggtcg    1080
gcgcccacct acatccacca gggcacggag accggcaaga aggtcggcta ctccgacccg    1140
agctacgtcg tcgatcacca gacgggcacg atcttcaact ccacgtcaa gtcctacgac    1200 cagggctggg gcggctcgcg cggcggcacc gacccggaga accggggcat catccaggcc    1260
gaggtgtcga cctccaccgga caacggctgg acctggacgc accgcacgat caccgcggac    1320
atcacgaagg acaagccgtg gaccgcgcgt ttcgcggcct cgggccaggg catccagatt    1380
cagcacgggc ccacgccgg gcgcctggtg cagcagtaca cgatcaggac cgccggcggc    1440
gcggtgcagg ccgtctcggt ctactccgac gaccacggga agacgtggca ggccggcacg    1500
ccgatcggga ccggcatgga tgagaacaag gtcgttgagc tctccgacgg ctccctcatg    1560
ctcaactcgc gcgcctcgga tggctccggc ttccgcaagg tggcccactc caccgacggt    1620
gggcagacct ggagcgagcc ggtgtccgac aagaacctgc ccgactcggt ggacaacgcc    1680
cagatcatcc gagccttccc gaacgccgcg ccggacgacc gccgcgccaa ggtgctgctg    1740
ctgagccact accgaaccc gcggccgtgg tcgcgtgacc gcggcaccat ctcgatgtcc    1800
```

```
tgcgacgacg gcgcctcctg gacgaccagc aaggtcttcc acgagcccTT cgtcggatac    1860
acgacgatcg cggtgcagtc cgacggcagc atcgggctgc tcagcgagga cgcccacaac    1920
ggcgccgact acggcggcat ctggtaccgc aacttcacga tgaactggct cggcgagcag    1980
tgcggccaga agccggcgga gccgagcccg gcgccgtcgc cgacggcggc accctcagcg    2040
gcaccgacgg agaagccggc cccgtcggcc gcgccgagcg ctgagcccac gcaggcaccg    2100
gcaccatcct ccgcgcccga gccgagcgct gcgcccgagc cgagcagcgc cccggcgccg    2160
gagcccacga ccgctccgag cacggagccc acaccggctc ctgcgcccag ctccgcacct    2220
gagcagaccg atgggccgac cgctgcgccc gcaccggaga cgtcctctgc accggccgcc    2280
gaaccgacgc aggccccgac ggtggcgcct tctgttgagc ccacgcaggc tccgggtgcg    2340
cagccgagct cagcacccaa gccggggcg acgggtcggg ccccgtcggt ggtgaacccg     2400
aaggcgaccg gggcggcgac ggagcctggg acgccgtcat cgagcgcgag cccggcaccg    2460
agccggaacg cggcgccgac gccgaagccg ggcatggagc cgatgagat tgatcggccg     2520 tctgacggca ccatggcgca gccgaccggt ggcgccagcg cgccgagtgc cgcgccgacg    2580
caggcggcga aggccggcag caggctgtct cgcacgggga ccaacgcgct gctgatcctg    2640
ggccttgcgg gtgtcgcggt tgtcggcggg tacctgctgc tgcgggctcg ccgttcgaag    2700
aactga                                                               2706

<210> SEQ ID NO 12
<211> LENGTH: 901
<212> TYPE: PRT
<213> ORGANISM: Actinomyces viscosus

<400> SEQUENCE: 12

Met Thr Ser His Ser Pro Phe Ser Arg Arg Arg Leu Pro Ala Leu Leu
 1               5                  10                  15

Gly Ser Leu Pro Leu Ala Ala Thr Gly Leu Ile Ala Ala Pro Pro
             20                  25                  30

Ala His Ala Val Pro Thr Ser Asp Gly Leu Ala Asp Val Thr Ile Thr
         35                  40                  45

Gln Val Asn Ala Pro Ala Asp Gly Leu Tyr Ser Val Gly Asp Val Met
     50                  55                  60

Thr Phe Asn Ile Thr Leu Thr Asn Thr Ser Gly Glu Ala His Ser Tyr
 65                  70                  75                  80

Ala Pro Ala Ser Thr Asn Leu Ser Gly Asn Val Ser Lys Cys Arg Trp
                 85                  90                  95

Arg Asn Val Pro Ala Gly Thr Thr Lys Thr Asp Cys Thr Gly Leu Ala
            100                 105                 110

Thr His Thr Val Thr Ala Glu Asp Leu Lys Ala Gly Gly Phe Thr Pro
        115                 120                 125

Gln Ile Ala Tyr Glu Val Lys Ala Val Glu Tyr Ala Gly Lys Ala Leu
    130                 135                 140

Ser Thr Pro Glu Thr Ile Lys Gly Ala Thr Ser Pro Val Lys Ala Asn
145                 150                 155                 160

Ser Leu Arg Val Glu Ser Ile Thr Pro Ser Ser Gln Glu Asn Tyr
                165                 170                 175

Lys Leu Gly Asp Thr Val Ser Tyr Thr Val Arg Val Arg Ser Val Ser
            180                 185                 190

Asp Lys Thr Ile Asn Val Ala Ala Thr Glu Ser Ser Phe Asp Asp Leu
        195                 200                 205
```

-continued

```
Gly Arg Gln Cys His Trp Gly Gly Leu Lys Pro Gly Lys Gly Ala Val
    210                 215                 220
Tyr Asn Cys Lys Pro Leu Thr His Thr Ile Thr Gln Ala Asp Val Asp
225                 230                 235                 240
Ala Gly Arg Trp Thr Pro Ser Ile Thr Leu Thr Ala Thr Gly Thr Asp
                245                 250                 255
Gly Ala Thr Leu Gln Thr Leu Thr Ala Thr Gly Asn Pro Ile Asn Val
            260                 265                 270
Val Gly Asp His Pro Gln Ala Thr Pro Ala Pro Asp Ala Ser
        275                 280                 285
Thr Glu Leu Pro Ala Ser Met Ser Gln Ala Gln His Leu Ala Ala Asn
    290                 295                 300
Thr Ala Thr Asp Asn Tyr Arg Ile Pro Ala Ile Thr Thr Ala Pro Asn
305                 310                 315                 320
Gly Asp Leu Leu Ile Ser Tyr Asp Glu Arg Pro Lys Asp Asn Gly Asn
                325                 330                 335
Gly Gly Ser Asp Ala Pro Asn Pro Asn His Ile Val Gln Arg Arg Ser
            340                 345                 350
Thr Asp Gly Gly Lys Thr Trp Ser Ala Pro Thr Tyr Ile His Gln Gly
    355                 360                 365
Thr Glu Thr Gly Lys Lys Val Gly Tyr Ser Asp Pro Ser Tyr Val Val
370                 375                 380
Asp His Gln Thr Gly Thr Ile Phe Asn Phe His Val Lys Ser Tyr Asp
385                 390                 395                 400
Gln Gly Trp Gly Gly Ser Arg Gly Thr Asp Pro Glu Asn Arg Gly
                405                 410                 415
Ile Ile Gln Ala Glu Val Ser Thr Ser Thr Asp Asn Gly Trp Thr Trp
            420                 425                 430
Thr His Arg Thr Ile Thr Ala Asp Ile Thr Lys Asp Lys Pro Trp Thr
    435                 440                 445
Ala Arg Phe Ala Ala Ser Gly Gln Gly Ile Gln Ile Gln His Gly Pro
450                 455                 460
His Ala Gly Arg Leu Val Gln Gln Tyr Thr Ile Arg Thr Ala Gly Gly
465                 470                 475                 480
Ala Val Gln Ala Val Ser Val Tyr Ser Asp Asp His Gly Lys Thr Trp
                485                 490                 495
Gln Ala Gly Thr Pro Ile Gly Thr Gly Met Asp Glu Asn Lys Val Val
            500                 505                 510
Glu Leu Ser Asp Gly Ser Leu Met Leu Asn Ser Arg Ala Ser Asp Gly
    515                 520                 525
Ser Gly Phe Arg Lys Val Ala His Ser Thr Asp Gly Gly Gln Thr Trp
530                 535                 540
Ser Glu Pro Val Ser Asp Lys Asn Leu Pro Asp Ser Val Asp Asn Ala
545                 550                 555                 560
Gln Ile Ile Arg Ala Phe Pro Asn Ala Ala Pro Asp Pro Arg Ala
                565                 570                 575
Lys Val Leu Leu Leu Ser His Ser Pro Asn Pro Arg Pro Trp Ser Arg
            580                 585                 590
Asp Arg Gly Thr Ile Ser Met Ser Cys Asp Asp Gly Ala Ser Trp Thr
    595                 600                 605
Thr Ser Lys Val Phe His Glu Pro Phe Val Gly Tyr Thr Thr Ile Ala
610                 615                 620
Val Gln Ser Asp Gly Ser Ile Gly Leu Leu Ser Glu Asp Ala His Asn
625                 630                 635                 640
```

Gly Ala Asp Tyr Gly Gly Ile Trp Tyr Arg Asn Phe Thr Met Asn Trp
              645                 650                 655

Leu Gly Glu Gln Cys Gly Gln Lys Pro Ala Glu Pro Ser Pro Ala Pro
            660                 665                 670

Ser Pro Thr Ala Ala Pro Ser Ala Pro Thr Glu Lys Pro Ala Pro
            675                 680                 685

Ser Ala Ala Pro Ser Ala Glu Pro Thr Gln Ala Pro Ala Pro Ser Ser
        690                 695                 700

Ala Pro Glu Pro Ser Ala Ala Pro Glu Pro Ser Ser Ala Pro Ala Pro
705                 710                 715                 720

Glu Pro Thr Thr Ala Pro Ser Thr Glu Pro Thr Pro Ala Pro Ala Pro
            725                 730                 735

Ser Ser Ala Pro Glu Gln Thr Asp Gly Pro Thr Ala Ala Pro Ala Pro
            740                 745                 750

Glu Thr Ser Ser Ala Pro Ala Ala Glu Pro Thr Gln Ala Pro Thr Val
            755                 760                 765

Ala Pro Ser Val Glu Pro Thr Gln Ala Pro Gly Ala Gln Pro Ser Ser
        770                 775                 780

Ala Pro Lys Pro Gly Ala Thr Gly Arg Ala Pro Ser Val Val Asn Pro
785                 790                 795                 800

Lys Ala Thr Gly Ala Ala Thr Glu Pro Gly Thr Pro Ser Ser Ser Ala
            805                 810                 815

Ser Pro Ala Pro Ser Arg Asn Ala Ala Pro Thr Pro Lys Pro Gly Met
            820                 825                 830

Glu Pro Asp Glu Ile Asp Arg Pro Ser Asp Gly Thr Met Ala Gln Pro
            835                 840                 845

Thr Gly Gly Ala Ser Ala Pro Ser Ala Ala Pro Thr Gln Ala Ala Lys
        850                 855                 860

Ala Gly Ser Arg Leu Ser Arg Thr Gly Thr Asn Ala Leu Leu Ile Leu
865                 870                 875                 880

Gly Leu Ala Gly Val Ala Val Val Gly Gly Tyr Leu Leu Leu Arg Ala
            885                 890                 895

Arg Arg Ser Lys Asn
            900

<210> SEQ ID NO 13
<211> LENGTH: 1887
<212> TYPE: DNA
<213> ORGANISM: Actinomyces viscosus

<400> SEQUENCE: 13
ggcgaccacc cgcaggccac gcccgcaccg gcgcccgacg cgagcacgga gctgccggcc     60
tcaatgagcc aggcccagca cctggccgcc aacacggcca ccgacaacta ccgcatcccg    120
gcgatcacca ccgcccccaa tgggacctg ctcatctcct acgacgagcg cccgaaggac    180
aacggcaacg gcggcagcga cgcccccaac ccgaaccaca tcgtccagcg ccgctccacc    240
gacggcggca agacctggtc ggcgcccacc tacatccacc agggcacgga gaccggcaag    300
aaggtcggct actccgaccc gagctacgtc gtcgatcacc agacgggcac gatcttcaac    360
ttccacgtca gtcctacga ccagggctgg ggcggctcgc gcggcggcac cgacccggag    420
aaccggggca tcatccaggc cgaggtgtcg acctccacgg acaacggctg gacctggacg    480
caccgcacga tcaccgcgga catcacgaag acaagccgt ggaccgcgcg tttcgcggcc    540
tcgggccagg gcatccagat tcagcacggg ccccacgccg ggcgcctggt gcagcagtac    600

-continued

```
acgatcagga ccgccggcgg cgcggtgcag gccgtctcgg tctactccga cgaccacggg    660
aagacgtggc aggccggcac gccgatcggg accggcatgg atgagaacaa ggtcgttgag    720
ctctccgacg gctccctcat gctcaactcg cgcgcctcgg atggctccgg cttccgcaag    780
gtggcccact ccaccgacgg tgggcagacc tggagcgagc cggtgtccga caagaacctg    840
cccgactcgg tggacaacgc ccagatcatc cgagccttcc cgaacgccgc gccggacgac    900
ccgcgcgcca aggtgctgct gctgagccac tcaccgaacc cgcggccgtg gtcgcgtgac    960
cgcggcacca tctcgatgtc ctgcgacgac ggcgcctcct ggacgaccag caaggtcttc   1020
cacgagccct tcgtcggata cacgacgatc gcggtgcagt ccgacggcag catcgggctg   1080
ctcagcgagg acgcccacaa cggcgccgac tacgcggca tctggtaccg caacttcacg   1140
atgaactggc tcggcgagca gtgcggccag aagccggcgg agccgagccc ggcgccgtcg   1200
ccgacggcgg caccctcagc ggcaccgacg gagaagccgg cccgtcggc cgcgccgagc   1260
gctgagccca gcaggcacc ggcaccatcc tccgcgcccg agccgagcgc tgcgcccgag   1320
ccgagcagcg ccccggcgcc ggagcccacg accgctccga gcacggagcc cacaccggct   1380
cctgcgccca gctccgcacc tgagcagacc gatgggccga ccgctgcgcc cgcaccggag   1440
acgtcctctg caccggccgc cgaaccgacg caggccccga cggtggcgcc ttctgttgag   1500
cccacgcagg ctccgggtgc gcagccgagc tcagcaccca gccggggc gacgggtcgg   1560
gccccgtcgg tggtgaaccc gaaggcgacc ggggcggcga cggagcctgg gacgccgtca   1620
tcgagcgcga gccggcacc gagccggaac gggcgccga cgccgaagcc gggcatggag   1680
cccgatgaga ttgatcggcc gtctgacggc accatggcgc agccgaccgg tggcgccagc   1740
gcgccgagtg ccgcgccgac gcaggcgcg aaggccggca gcaggctgtc tcgcacgggg   1800
accaacgcgc tgctgatcct gggccttgcg ggtgtcgcgg ttgtcggcgg gtacctgctg   1860
ctgcgggctc gccgttcgaa gaactga                                      1887
```

<210> SEQ ID NO 14
<211> LENGTH: 628
<212> TYPE: PRT
<213> ORGANISM: Actinomyces viscosus

<400> SEQUENCE: 14

```
Gly Asp His Pro Gln Ala Thr Pro Ala Pro Ala Pro Asp Ala Ser Thr
 1               5                  10                  15

Glu Leu Pro Ala Ser Met Ser Gln Ala Gln His Leu Ala Ala Asn Thr
            20                  25                  30

Ala Thr Asp Asn Tyr Arg Ile Pro Ala Ile Thr Thr Ala Pro Asn Gly
        35                  40                  45

Asp Leu Leu Ile Ser Tyr Asp Glu Arg Pro Lys Asp Asn Gly Asn Gly
    50                  55                  60

Gly Ser Asp Ala Pro Asn Pro Asn His Ile Val Gln Arg Arg Ser Thr
65                  70                  75                  80

Asp Gly Gly Lys Thr Trp Ser Ala Pro Thr Tyr Ile His Gln Gly Thr
                85                  90                  95

Glu Thr Gly Lys Lys Val Gly Tyr Ser Asp Pro Ser Tyr Val Val Asp
            100                 105                 110

His Gln Thr Gly Thr Ile Phe Asn Phe His Val Lys Ser Tyr Asp Gln
        115                 120                 125

Gly Trp Gly Gly Ser Arg Gly Gly Thr Asp Pro Glu Asn Arg Gly Ile
    130                 135                 140

Ile Gln Ala Glu Val Ser Thr Ser Thr Asp Asn Gly Trp Thr Trp Thr
```

```
              145                 150                 155                 160
His Arg Thr Ile Thr Ala Asp Ile Thr Lys Asp Lys Pro Trp Thr Ala
                    165                 170                 175

Arg Phe Ala Ala Ser Gly Gln Gly Ile Gln Ile Gln His Gly Pro His
            180                 185                 190

Ala Gly Arg Leu Val Gln Gln Tyr Thr Ile Arg Thr Ala Gly Gly Ala
        195                 200                 205

Val Gln Ala Val Ser Val Tyr Ser Asp Asp His Gly Lys Thr Trp Gln
210                 215                 220

Ala Gly Thr Pro Ile Gly Thr Gly Met Asp Glu Asn Lys Val Val Glu
225                 230                 235                 240

Leu Ser Asp Gly Ser Leu Met Leu Asn Ser Arg Ala Ser Asp Gly Ser
                245                 250                 255

Gly Phe Arg Lys Val Ala His Ser Thr Asp Gly Gly Gln Thr Trp Ser
            260                 265                 270

Glu Pro Val Ser Asp Lys Asn Leu Pro Asp Ser Val Asp Asn Ala Gln
        275                 280                 285

Ile Ile Arg Ala Phe Pro Asn Ala Ala Pro Asp Asp Pro Arg Ala Lys
290                 295                 300

Val Leu Leu Leu Ser His Ser Pro Asn Pro Arg Pro Trp Ser Arg Asp
305                 310                 315                 320

Arg Gly Thr Ile Ser Met Ser Cys Asp Asp Gly Ala Ser Trp Thr Thr
                325                 330                 335

Ser Lys Val Phe His Glu Pro Phe Val Gly Tyr Thr Thr Ile Ala Val
            340                 345                 350

Gln Ser Asp Gly Ser Ile Gly Leu Leu Ser Glu Asp Ala His Asn Gly
        355                 360                 365

Ala Asp Tyr Gly Gly Ile Trp Tyr Arg Asn Phe Thr Met Asn Trp Leu
370                 375                 380

Gly Glu Gln Cys Gly Gln Lys Pro Ala Glu Pro Ser Pro Ala Pro Ser
385                 390                 395                 400

Pro Thr Ala Ala Pro Ser Ala Ala Pro Thr Glu Lys Pro Ala Pro Ser
                405                 410                 415

Ala Ala Pro Ser Ala Glu Pro Thr Gln Ala Pro Ala Pro Ser Ser Ala
            420                 425                 430

Pro Glu Pro Ser Ala Ala Pro Glu Pro Ser Ser Ala Pro Ala Pro Glu
        435                 440                 445

Pro Thr Thr Ala Pro Ser Thr Glu Pro Thr Pro Ala Pro Ala Pro Ser
450                 455                 460

Ser Ala Pro Glu Gln Thr Asp Gly Pro Thr Ala Ala Pro Ala Pro Glu
465                 470                 475                 480

Thr Ser Ser Ala Pro Ala Ala Glu Pro Thr Gln Ala Pro Thr Val Ala
                485                 490                 495

Pro Ser Val Glu Pro Thr Gln Ala Pro Gly Ala Gln Pro Ser Ser Ala
            500                 505                 510

Pro Lys Pro Gly Ala Thr Gly Arg Ala Pro Ser Val Val Asn Pro Lys
        515                 520                 525

Ala Thr Gly Ala Ala Thr Glu Pro Gly Thr Pro Ser Ser Ser Ala Ser
530                 535                 540

Pro Ala Pro Ser Arg Asn Ala Ala Pro Thr Pro Lys Pro Gly Met Glu
545                 550                 555                 560

Pro Asp Glu Ile Asp Arg Pro Ser Asp Gly Thr Met Ala Gln Pro Thr
                565                 570                 575
```

```
Gly Gly Ala Ser Ala Pro Ser Ala Pro Thr Gln Ala Ala Lys Ala
            580                 585                 590

Gly Ser Arg Leu Ser Arg Thr Gly Thr Asn Ala Leu Leu Ile Leu Gly
        595                 600                 605

Leu Ala Gly Val Ala Val Val Gly Gly Tyr Leu Leu Leu Arg Ala Arg
    610                 615                 620

Arg Ser Lys Asn
625

<210> SEQ ID NO 15
<211> LENGTH: 1182
<212> TYPE: DNA
<213> ORGANISM: Artificial Sequence
<220> FEATURE:
<223> OTHER INFORMATION: Synthetic Construct

<400> SEQUENCE: 15
ggagatcatc cacaagctac accagcacct gcaccagatg ctagcactga gctgccagca      60
agcatgtctc aggctcagca tcttgcagca aatacggcta ctgataatta tcgcattcca     120
gcgattacaa ccgctccgaa tggtgattta ctgattagct atgatgaacg gccgaaggac     180
aatggaaatg gtggttccga tgcccctaac ccgaatcata ttgttcagcg tcgctccaca     240
gatggcggta aaacttggag cgcgccaacc tatattcatc agggtacgga gactggcaag     300
aaagtgggat attccgaccc ctcttatgtg gtggatcatc aaaccggtac aatcttcaat     360
tttcatgtga atcatacga tcagggctgg ggaggtagcc gtgggggaac agacccggaa     420
aaccgcggga ttattcaggc agaggtgtct acgagcacgg ataatggatg gacgtggaca     480
catcgcacca tcaccgcgga tattacgaaa gataaaccgt ggaccgcgcg ttttgcggcg     540
tccggccaag gcattcagat ccagcatggg ccgcatgccg ccgtctggt gcaacagtat      600 accattcgta cggccggtgg agcggtgcag gctgtatcgg tttattccga tgatcatggg     660
aaaacgtggc aggctggcac cccgattggg acgggtatgg atgaaaacaa agttgtagag     720
ctgtctgacg gctctctgat gctgaacagt cgtgcgtcgg acgggagcgg ctttcgtaag     780
gttgcgcata gcactgatgg tgggcagacc tggtccgaac cggtttcgga caaaaatttg     840
ccggattcgg ttgataatgc ccagataatt cgtgcgtttc ctaatgctgc ccccgatgac     900
ccgcgcgcga agtacttct tctgagtcat tccccaaatc cacgtccgtg gtcccgggat      960
cgtggtacga taagcatgtc atgtgatgac ggggcctcat ggaccacttc caaagttttt    1020
cacgaaccgt tgtgggcta cacgactatt gcagttcaga gtgatggaag catcggtctg    1080
ctgtcggagg acgcgcacaa tggcgctgat tatggtggca tctggtatcg taattttacg    1140
atgaactggc tgggagaaca atgtggacaa aaacccgcgg aa                      1182

<210> SEQ ID NO 16
<211> LENGTH: 394
<212> TYPE: PRT
<213> ORGANISM: Actinomyces viscosus

<400> SEQUENCE: 16

Gly Asp His Pro Gln Ala Thr Pro Ala Pro Ala Pro Asp Ala Ser Thr
1               5                   10                  15

Glu Leu Pro Ala Ser Met Ser Gln Ala Gln His Leu Ala Ala Asn Thr
            20                  25                  30

Ala Thr Asp Asn Tyr Arg Ile Pro Ala Ile Thr Thr Ala Pro Asn Gly
        35                  40                  45

Asp Leu Leu Ile Ser Tyr Asp Glu Arg Pro Lys Asp Asn Gly Asn Gly
```

```
                50                  55                  60
Gly Ser Asp Ala Pro Asn Pro Asn His Ile Val Gln Arg Arg Ser Thr
 65                  70                  75                  80

Asp Gly Gly Lys Thr Trp Ser Ala Pro Thr Tyr Ile His Gln Gly Thr
                 85                  90                  95

Glu Thr Gly Lys Lys Val Gly Tyr Ser Asp Pro Ser Tyr Val Val Asp
                100                 105                 110

His Gln Thr Gly Thr Ile Phe Asn Phe His Val Lys Ser Tyr Asp Gln
                115                 120                 125

Gly Trp Gly Gly Ser Arg Gly Gly Thr Asp Pro Glu Asn Arg Gly Ile
            130                 135                 140

Ile Gln Ala Glu Val Ser Thr Ser Thr Asp Asn Gly Trp Thr Trp Thr
145                 150                 155                 160

His Arg Thr Ile Thr Ala Asp Ile Thr Lys Asp Lys Pro Trp Thr Ala
                165                 170                 175

Arg Phe Ala Ala Ser Gly Gln Gly Ile Gln Ile Gln His Gly Pro His
                180                 185                 190

Ala Gly Arg Leu Val Gln Gln Tyr Thr Ile Arg Thr Ala Gly Gly Ala
            195                 200                 205

Val Gln Ala Val Ser Val Tyr Ser Asp Asp His Gly Lys Thr Trp Gln
210                 215                 220

Ala Gly Thr Pro Ile Gly Thr Gly Met Asp Glu Asn Lys Val Val Glu
225                 230                 235                 240

Leu Ser Asp Gly Ser Leu Met Leu Asn Ser Arg Ala Ser Asp Gly Ser
                245                 250                 255

Gly Phe Arg Lys Val Ala His Ser Thr Asp Gly Gly Gln Thr Trp Ser
            260                 265                 270

Glu Pro Val Ser Asp Lys Asn Leu Pro Asp Ser Val Asp Asn Ala Gln
            275                 280                 285

Ile Ile Arg Ala Phe Pro Asn Ala Ala Pro Asp Pro Arg Ala Lys
                290                 295                 300

Val Leu Leu Leu Ser His Ser Pro Asn Pro Arg Pro Trp Ser Arg Asp
305                 310                 315                 320

Arg Gly Thr Ile Ser Met Ser Cys Asp Asp Gly Ala Ser Trp Thr Thr
                325                 330                 335

Ser Lys Val Phe His Glu Pro Phe Val Gly Tyr Thr Thr Ile Ala Val
                340                 345                 350

Gln Ser Asp Gly Ser Ile Gly Leu Leu Ser Glu Asp Ala His Asn Gly
                355                 360                 365

Ala Asp Tyr Gly Gly Ile Trp Tyr Arg Asn Phe Thr Met Asn Trp Leu
            370                 375                 380

Gly Glu Gln Cys Gly Gln Lys Pro Ala Glu
385                 390

<210> SEQ ID NO 17
<211> LENGTH: 6
<212> TYPE: PRT
<213> ORGANISM: Artificial Sequence
<220> FEATURE:
<223> OTHER INFORMATION: Synthetic Construct

<400> SEQUENCE: 17

Met Val Lys Arg Lys Lys
 1               5

<210> SEQ ID NO 18
```

<210> SEQ ID NO 18
<211> LENGTH: 1281
<212> TYPE: DNA
<213> ORGANISM: Artificial Sequence
<220> FEATURE:
<223> OTHER INFORMATION: Synthetic Construct

<400> SEQUENCE: 18

```
ccatggttaa gcgcaaaaaa aaaggcggca aaaacggtaa aaatcgtcgt aaccgtaaga      60
aaaaaaatcc tggagatcat ccacaagcta caccagcacc tgcaccagat gctagcactg     120
agctgccagc aagcatgtct caggctcagc atcttgcagc aaatacggct actgataatt     180
atcgcattcc agcgattaca accgctccga atggtgattt actgattagc tatgatgaac     240
ggccgaagga caatggaaat ggtggttccg atgcccctaa cccgaatcat attgttcagc     300
gtcgctccac agatggcggt aaaacttgga gcgcgccaac ctatattcat cagggtacgg     360
agactggcaa gaaagtggga tattccgacc cctcttatgt ggtggatcat caaaccggta     420
caatcttcaa ttttcatgtg aaatcatacg atcagggctg gggaggtagc cgtgggggaa     480
cagacccgga aaaccgcggg attattcagg cagaggtgtc tacgagcacg gataatggat     540
ggacgtggac acatcgcacc atcaccgcgg atattacgaa agataaaccg tggaccgcgc     600
gttttgcggc gtccggccaa ggcattcaga tccagcatgg gccgcatgcc ggccgtctgg     660
tgcaacagta taccattcgt acggccggtg gagcggtgca ggctgtatcg gtttattccg     720
atgatcatgg gaaaacgtgg caggctggca ccccgattgg gacgggtatg gatgaaaaca     780
aagttgtaga gctgtctgac ggctctctga tgctgaacag tcgtgcgtcg gacgggagcg     840
gctttcgtaa ggttgcgcat agcactgatg gtgggcagac ctggtccgaa ccggtttcgg     900
acaaaaattt gccggattcg gttgataatg cccagataat tcgtgcgttt cctaatgctg     960
cccccgatga cccgcgcgcg aaagtacttc ttctgagtca ttccccaaat ccacgtccgt    1020
ggtcccggga tcgtggtacg ataagcatgt catgtgatga cggggcctca tggaccactt    1080
ccaaagtttt tcacgaaccg tttgtgggct acacgactat tgcagttcag agtgatggaa    1140
gcatcggtct gctgtcggag gacgcgcaca tggcgctga ttatggtggc atctggtatc    1200
gtaattttac gatgaactgg ctgggagaac aatgtggaca aaaacccgcg gaataagctt    1260
aaaaacccgc ggaataagct t                                             1281
```

<210> SEQ ID NO 19
<211> LENGTH: 444
<212> TYPE: PRT
<213> ORGANISM: Artificial Sequence
<220> FEATURE:
<223> OTHER INFORMATION: Synthetic Construct

<400> SEQUENCE: 19

```
Met Val Lys Arg Lys Lys Lys Gly Gly Lys Asn Gly Lys Asn Arg Arg
 1               5                  10                  15

Asn Arg Lys Lys Lys Asn Pro Gly Asp His Pro Gln Ala Thr Pro Ala
                20                  25                  30

Pro Ala Pro Asp Ala Ser Thr Glu Leu Pro Ala Ser Met Ser Gln Ala
        35                  40                  45

Gln His Leu Ala Ala Asn Thr Ala Thr Asp Asn Tyr Arg Ile Pro Ala
    50                  55                  60

Ile Thr Thr Ala Pro Asn Gly Asp Leu Leu Ile Ser Tyr Asp Glu Arg
65                  70                  75                  80

Pro Lys Asp Asn Gly Asn Gly Gly Ser Asp Ala Pro Asn Pro Asn His
                85                  90                  95
```

```
Ile Val Gln Arg Arg Ser Thr Asp Gly Gly Lys Thr Trp Ser Ala Pro
                100                 105                 110

Thr Tyr Ile His Gln Gly Thr Glu Thr Gly Lys Lys Val Gly Tyr Ser
            115                 120                 125

Asp Pro Ser Tyr Val Val Asp His Gln Thr Gly Thr Ile Phe Asn Phe
        130                 135                 140

His Val Lys Ser Tyr Asp Gln Gly Trp Gly Gly Ser Arg Gly Gly Thr
145                 150                 155                 160

Asp Pro Glu Asn Arg Gly Ile Ile Gln Ala Glu Val Ser Thr Ser Thr
                165                 170                 175

Asp Asn Gly Trp Thr Trp Thr His Arg Thr Ile Thr Ala Asp Ile Thr
            180                 185                 190

Lys Asp Lys Pro Trp Thr Ala Arg Phe Ala Ala Ser Gly Gln Gly Ile
        195                 200                 205

Gln Ile Gln His Gly Pro His Ala Gly Arg Leu Val Gln Gln Tyr Thr
    210                 215                 220

Ile Arg Thr Ala Gly Gly Ala Val Gln Ala Val Ser Val Tyr Ser Asp
225                 230                 235                 240

Asp His Gly Lys Thr Trp Gln Ala Gly Thr Pro Ile Gly Thr Gly Met
                245                 250                 255

Asp Glu Asn Lys Val Val Glu Leu Ser Asp Gly Ser Leu Met Leu Asn
            260                 265                 270

Ser Arg Ala Ser Asp Gly Ser Gly Phe Arg Lys Val Ala His Ser Thr
        275                 280                 285

Asp Gly Gly Gln Thr Trp Ser Glu Pro Val Ser Asp Lys Asn Leu Pro
    290                 295                 300

Asp Ser Val Asp Asn Ala Gln Ile Ile Arg Ala Phe Pro Asn Ala Ala
305                 310                 315                 320

Pro Asp Asp Pro Arg Ala Lys Val Leu Leu Leu Ser His Ser Pro Asn
                325                 330                 335

Pro Arg Pro Trp Ser Arg Asp Arg Gly Thr Ile Ser Met Ser Cys Asp
            340                 345                 350

Asp Gly Ala Ser Trp Thr Thr Ser Lys Val Phe His Glu Pro Phe Val
        355                 360                 365

Gly Tyr Thr Thr Ile Ala Val Gln Ser Asp Gly Ser Ile Gly Leu Leu
    370                 375                 380

Ser Glu Asp Ala His Asn Gly Ala Asp Tyr Gly Gly Ile Trp Tyr Arg
385                 390                 395                 400

Asn Phe Thr Met Asn Trp Leu Gly Glu Gln Cys Gly Gln Lys Pro Ala
                405                 410                 415

Glu Gly Ala Asp Tyr Gly Gly Ile Trp Tyr Arg Asn Phe Thr Met Asn
            420                 425                 430

Trp Leu Gly Glu Gln Cys Gly Gln Lys Pro Ala Glu
        435                 440

<210> SEQ ID NO 20
<211> LENGTH: 1248
<212> TYPE: DNA
<213> ORGANISM: Artificial Sequence
<220> FEATURE:
<223> OTHER INFORMATION: Synthetic Construct

<400> SEQUENCE: 20
atgggagatc atccacaagc tacaccagca cctgcaccag atgctagcac tgagctgcca      60
gcaagcatgt ctcaggctca gcatcttgca gcaaatacgg ctactgataa ttatcgcatt     120
```

```
ccagcgatta caaccgctcc gaatggtgat ttactgatta gctatgatga acggccgaag    180
gacaatggaa atggtggttc cgatgcccct aacccgaatc atattgttca gcgtcgctcc    240
acagatggcg gtaaaacttg gagcgcgcca acctatattc atcagggtac ggagactggc    300
aagaaagtgg gatattccga cccctcttat gtggtggatc atcaaaccgg tacaatcttc    360
aattttcatg tgaaatcata cgatcagggc tggggaggta gccgtggggg aacagacccg    420
gaaaaccgcg ggattattca ggcagaggtg tctacgagca cggataatgg atggacgtgg    480
acacatcgca ccatcaccgc ggatattacg aaagataaac cgtggaccgc gcgttttgcg    540
gcgtccggcc aaggcattca gatccagcat gggccgcatg ccggccgtct ggtgcaacag    600
tataccattc gtacggccgg tggagcggtg caggctgtat cggtttattc cgatgatcat    660
gggaaaacgt ggcaggctgg caccccgatt gggacgggta tggatgaaaa caaagttgta    720
gagctgtctg acggctctct gatgctgaac agtcgtgcgt cggacgggag cggcttttcgt   780
aaggttgcgc atagcactga tggtgggcag acctggtccg aaccggtttc ggacaaaaat    840
ttgccggatt cggttgataa tgcccagata attcgtgcgt ttcctaatgc tgccccgat     900
gacccgcgcg cgaaagtact tcttctgagt cattccccaa atccacgtcc gtggtcccgg    960
gatcgtggta cgataagcat gtcatgtgat gacgggccct catggaccac ttccaaagtt   1020
tttcacgaac cgtttgtggg ctacacgact attgcagttc agagtgatgg aagcatcggt   1080
ctgctgtcgg aggacgcgca caatggcgct gattatggtg gcatctggta cgtaatttt    1140
acgatgaact ggctgggaga acaatgtgga caaaaacccg cgaagcgcaa aaaaaaggc    1200
ggcaaaaacg gtaaaaatcg tcgtaaccgt aagaaaaaaa atccttga                1248
```

<210> SEQ ID NO 21
<211> LENGTH: 415
<212> TYPE: PRT
<213> ORGANISM: Artificial Sequence
<220> FEATURE:
<223> OTHER INFORMATION: Synthetic Construct

<400> SEQUENCE: 21

Met Gly Asp His Pro Gln Ala Thr Pro Ala Pro Asp Ala Ser
1               5                   10                  15

Thr Glu Leu Pro Ala Ser Met Ser Gln Ala Gln His Leu Ala Ala Asn
            20                  25                  30

Thr Ala Thr Asp Asn Tyr Arg Ile Pro Ala Ile Thr Thr Ala Pro Asn
        35                  40                  45

Gly Asp Leu Leu Ile Ser Tyr Asp Glu Arg Pro Lys Asp Asn Gly Asn
    50                  55                  60

Gly Gly Ser Asp Ala Pro Asn Pro Asn His Ile Val Gln Arg Arg Ser
65                  70                  75                  80

Thr Asp Gly Gly Lys Thr Trp Ser Ala Pro Thr Tyr Ile His Gln Gly
                85                  90                  95

Thr Glu Thr Gly Lys Lys Val Gly Tyr Ser Asp Pro Ser Tyr Val Val
            100                 105                 110

Asp His Gln Thr Gly Thr Ile Phe Asn Phe His Val Lys Ser Tyr Asp
        115                 120                 125

Gln Gly Trp Gly Gly Ser Arg Gly Gly Thr Pro Glu Asn Arg Gly
    130                 135                 140

Ile Ile Gln Ala Glu Val Ser Thr Ser Thr Asp Asn Gly Trp Thr Trp
145                 150                 155                 160

Thr His Arg Thr Ile Thr Ala Asp Ile Thr Lys Asp Lys Pro Trp Thr
                165                 170                 175

```
Ala Arg Phe Ala Ala Ser Gly Gln Gly Ile Gln Ile Gln His Gly Pro
            180                 185                 190

His Ala Gly Arg Leu Val Gln Gln Tyr Thr Ile Arg Thr Ala Gly Gly
        195                 200                 205

Ala Val Gln Ala Val Ser Val Tyr Ser Asp Asp His Gly Lys Thr Trp
210                 215                 220

Gln Ala Gly Thr Pro Ile Gly Thr Gly Met Asp Glu Asn Lys Val Val
225                 230                 235                 240

Glu Leu Ser Asp Gly Ser Leu Met Leu Asn Ser Arg Ala Ser Asp Gly
                245                 250                 255

Ser Gly Phe Arg Lys Val Ala His Ser Thr Asp Gly Gly Gln Thr Trp
            260                 265                 270

Ser Glu Pro Val Ser Asp Lys Asn Leu Pro Ser Val Asp Asn Ala
        275                 280                 285

Gln Ile Ile Arg Ala Phe Pro Asn Ala Ala Pro Asp Asp Pro Arg Ala
290                 295                 300

Lys Val Leu Leu Leu Ser His Ser Pro Asn Pro Arg Pro Trp Ser Arg
305                 310                 315                 320

Asp Arg Gly Thr Ile Ser Met Ser Cys Asp Gly Ala Ser Trp Thr
            325                 330                 335

Thr Ser Lys Val Phe His Glu Pro Phe Val Gly Tyr Thr Thr Ile Ala
            340                 345                 350

Val Gln Ser Asp Gly Ser Ile Gly Leu Leu Ser Glu Asp Ala His Asn
                355                 360                 365

Gly Ala Asp Tyr Gly Gly Ile Trp Tyr Arg Asn Phe Thr Met Asn Trp
        370                 375                 380

Leu Gly Glu Gln Cys Gly Gln Lys Pro Ala Lys Arg Lys Lys Lys Gly
385                 390                 395                 400

Gly Lys Asn Gly Lys Asn Arg Arg Asn Arg Lys Lys Lys Asn Pro
                405                 410                 415
```

<210> SEQ ID NO 22
<211> LENGTH: 1293
<212> TYPE: DNA
<213> ORGANISM: Artificial Sequence
<220> FEATURE:
<223> OTHER INFORMATION: Synthetic Construct

<400> SEQUENCE: 22

```
atgggagatc atccacaagc tacaccagca cctgcaccag atgctagcac tgagctgcca      60
gcaagcatgt ctcaggctca gcatcttgca gcaaatacgg ctactgataa ttatcgcatt     120
ccagcgatta caaccgctcc gaatggtgat ttactgatta gctatgatga acggccgaag     180
gacaatggaa atggtggttc cgatgcccct aacccgaatc atattgttca gcgtcgctcc     240
acagatggcg gtaaacttg gagcgcgcca acctatattc atcagggtac ggagactggc     300
aagaaagtgg atattccga ccctcttat gtggtggatc atcaaaccgg tacaatcttc     360
aattttcatg tgaaatcata cgatcaggc tggggaggta gccgtggggg aacagacccg     420
gaaaaccgcg ggattattca ggcagaggtg tctacgagca cggataatgg atggacgtgg     480
acacatcgca ccatcaccgc ggatattacg aaagataaac cgtggaccgc gcgttttgcg     540
gcgtccggcc aaggcattca gatccagcat gggccgcatg ccggccgtct ggtgcaacag     600
tataccattc gtacggccgg tggagcggtg caggctgtat cggtttattc cgatgatcat     660
gggaaaacgt ggcaggctgg caccccgatt gggacgggta tggatgaaaa caaagttgta     720
```

```
gagctgtctg acggctctct gatgctgaac agtcgtgcgt cggacgggag cggctttcgt    780
aaggttgcgc atagcactga tggtgggcag acctggtccg aaccggtttc ggacaaaaat    840
ttgccggatt cggttgataa tgcccagata attcgtgcgt ttcctaatgc tgccccgat    900 gacccgcgcg cgaaagtact tcttctgagt cattccccaa atccacgtcc gtggtcccgg    960
gatcgtggta cgataagcat gtcatgtgat gacggggcct catggaccac ttccaaagtt   1020
tttcacgaac cgtttgtggg ctacacgact attgcagttc agagtgatgg aagcatcggt   1080
ctgctgtcgg aggacgcgca caatggcgct gattatggtg gcatctggta tcgtaatttt   1140
acgatgaact ggctgggaga acaatgtgga caaaaacccg cggaaccgag cccagccccct   1200 agccctactg cagcaccgtc cgctgcaaag cgcaaaaaaa aaggcggcaa aaacggtaaa   1260
aatcgtcgta accgtaagaa aaaaaatcct tga                               1293
```

<210> SEQ ID NO 23
<211> LENGTH: 430
<212> TYPE: PRT
<213> ORGANISM: Artificial Sequence
<220> FEATURE:
<223> OTHER INFORMATION: Synthetic Construct

<400> SEQUENCE: 23

```
Met Gly Asp His Pro Gln Ala Thr Pro Ala Pro Ala Pro Asp Ala Ser
 1               5                   10                  15

Thr Glu Leu Pro Ala Ser Met Ser Gln Ala Gln His Leu Ala Ala Asn
             20                  25                  30

Thr Ala Thr Asp Asn Tyr Arg Ile Pro Ala Ile Thr Thr Ala Pro Asn
         35                  40                  45

Gly Asp Leu Leu Ile Ser Tyr Asp Glu Arg Pro Lys Asp Asn Gly Asn
     50                  55                  60

Gly Gly Ser Asp Ala Pro Asn Pro Asn His Ile Val Gln Arg Arg Ser
 65                  70                  75                  80

Thr Asp Gly Gly Lys Thr Trp Ser Ala Pro Thr Tyr Ile His Gln Gly
                 85                  90                  95

Thr Glu Thr Gly Lys Lys Val Gly Tyr Ser Asp Pro Ser Tyr Val Val
            100                 105                 110

Asp His Gln Thr Gly Thr Ile Phe Asn Phe His Val Lys Ser Tyr Asp
        115                 120                 125

Gln Gly Trp Gly Gly Ser Arg Gly Gly Thr Asp Pro Glu Asn Arg Gly
    130                 135                 140

Ile Ile Gln Ala Glu Val Ser Thr Ser Thr Asp Asn Gly Trp Thr Trp
145                 150                 155                 160

Thr His Arg Thr Ile Thr Ala Asp Ile Thr Lys Asp Lys Pro Trp Thr
                165                 170                 175

Ala Arg Phe Ala Ala Ser Gly Gln Gly Ile Gln Ile Gln His Gly Pro
            180                 185                 190

His Ala Gly Arg Leu Val Gln Gln Tyr Thr Ile Arg Thr Ala Gly Gly
        195                 200                 205

Ala Val Gln Ala Val Ser Val Tyr Ser Asp His Gly Lys Thr Trp
    210                 215                 220

Gln Ala Gly Thr Pro Ile Gly Thr Gly Met Asp Glu Asn Lys Val Val
225                 230                 235                 240

Glu Leu Ser Asp Gly Ser Leu Met Leu Asn Ser Arg Ala Ser Asp Gly
                245                 250                 255

Ser Gly Phe Arg Lys Val Ala His Ser Thr Asp Gly Gly Gln Thr Trp
            260                 265                 270
```

```
Ser Glu Pro Val Ser Asp Lys Asn Leu Pro Asp Ser Val Asp Asn Ala
            275                 280                 285

Gln Ile Ile Arg Ala Phe Pro Asn Ala Ala Pro Asp Asp Pro Arg Ala
        290                 295                 300

Lys Val Leu Leu Leu Ser His Ser Pro Asn Pro Arg Pro Trp Ser Arg
305                 310                 315                 320

Asp Arg Gly Thr Ile Ser Met Ser Cys Asp Asp Gly Ala Ser Trp Thr
                325                 330                 335

Thr Ser Lys Val Phe His Glu Pro Phe Val Gly Tyr Thr Thr Ile Ala
            340                 345                 350

Val Gln Ser Asp Gly Ser Ile Gly Leu Leu Ser Glu Asp Ala His Asn
        355                 360                 365

Gly Ala Asp Tyr Gly Gly Ile Trp Tyr Arg Asn Phe Thr Met Asn Trp
    370                 375                 380

Leu Gly Glu Gln Cys Gly Gln Lys Pro Ala Glu Pro Ser Pro Ala Pro
385                 390                 395                 400

Ser Pro Thr Ala Ala Pro Ser Ala Ala Lys Arg Lys Lys Lys Gly Gly
                405                 410                 415

Lys Asn Gly Lys Asn Arg Arg Asn Arg Lys Lys Lys Asn Pro
            420                 425                 430
```

<210> SEQ ID NO 24
<211> LENGTH: 1203
<212> TYPE: DNA
<213> ORGANISM: Artificial Sequence
<220> FEATURE:
<223> OTHER INFORMATION: Synthetic Construct

<400> SEQUENCE: 24

```
atgggagagc tgccagcaag catgtctcag gctcagcatc ttgcagcaaa tacggctact    60
gataattatc gcattccagc gattacaacc gctccgaatg gtgatttact gattagctat   120
gatgaacggc cgaaggacaa tggaaatggt ggttccgatg cccctaaccc gaatcatatt   180
gttcagcgtc gctccacaga tggcggtaaa acttggagcg cgccaaccta tattcatcag   240
ggtacggaga ctggcaagaa agtgggatat ccgaccccct cttatgtggt ggatcatcaa   300
accggtacaa tcttcaattt tcatgtgaaa tcatacgatc agggctgggg aggtagccgt   360
gggggaacag acccggaaaa ccgcgggatt attcaggcag aggtgtctac gagcacggat   420
aatggatgga cgtggacaca tcgcaccatc accgcggata ttacgaaaga taaaccgtgg   480
accgcgcgtt ttgcggcgtc cggccaaggc attcagatcc agcatgggcc gcatgccggc   540
cgtctggtgc aacagtatac cattcgtacg gccggtggag cggtgcaggc tgtatcggtt   600
tattccgatg atcatgggaa aacgtggcag gctggcaccc cgattgggac gggtatggat   660
gaaaacaaag ttgtagagct gtctgacggc tctctgatgc tgaacagtcg tcgtcggac    720
gggagcggct tcgtaaggt tgcgcatagc actgatggtg gcagacctg gtccgaaccg    780
gtttcggaca aaaatttgcc ggattcggtt gataatgccc agataattcg tgcgtttcct   840
aatgctgccc ccgatgaccc gcgcgcgaaa gtacttcttc tgagtcattc ccaaaatcca   900
cgtccgtggt cccgggatcg tggtacgata agcatgtcat gtgatgacgg ggcctcatgg   960
accacttcca agttttttca cgaaccgttt gtgggctaca cgactattgc agttcagagt  1020
gatggaagca tcggtctgct gtcggaggac gcgcacaatg gcgctgatta tggtggcatc  1080
tggtatcgta attttacgat gaactggctg ggagaacaat gtggacaaaa acccgcgaag  1140
cgcaaaaaaa aaggcggcaa aaacggtaaa aatcgtcgta accgtaagaa aaaaaatcct  1200
``` tga                                                              1203

<210> SEQ ID NO 25
<211> LENGTH: 400
<212> TYPE: PRT
<213> ORGANISM: Artificial Sequence
<220> FEATURE:
<223> OTHER INFORMATION: Synthetic Construct

<400> SEQUENCE: 25

Met Gly Glu Leu Pro Ala Ser Met Ser Gln Ala Gln His Leu Ala Ala
 1               5                  10                  15

Asn Thr Ala Thr Asp Asn Tyr Arg Ile Pro Ala Ile Thr Thr Ala Pro
            20                  25                  30

Asn Gly Asp Leu Leu Ile Ser Tyr Asp Glu Arg Pro Lys Asp Asn Gly
        35                  40                  45

Asn Gly Gly Ser Asp Ala Pro Asn Pro Asn His Ile Val Gln Arg Arg
    50                  55                  60

Ser Thr Asp Gly Gly Lys Thr Trp Ser Ala Pro Thr Tyr Ile His Gln
65                  70                  75                  80

Gly Thr Glu Thr Gly Lys Lys Val Gly Tyr Ser Asp Pro Ser Tyr Val
                85                  90                  95

Val Asp His Gln Thr Gly Thr Ile Phe Asn Phe His Val Lys Ser Tyr
            100                 105                 110

Asp Gln Gly Trp Gly Gly Ser Arg Gly Gly Thr Asp Pro Glu Asn Arg
        115                 120                 125

Gly Ile Ile Gln Ala Glu Val Ser Thr Ser Thr Asp Asn Gly Trp Thr
    130                 135                 140

Trp Thr His Arg Thr Ile Thr Ala Asp Ile Thr Lys Asp Lys Pro Trp
145                 150                 155                 160

Thr Ala Arg Phe Ala Ala Ser Gly Gln Gly Ile Gln Ile Gln His Gly
                165                 170                 175

Pro His Ala Gly Arg Leu Val Gln Gln Tyr Thr Ile Arg Thr Ala Gly
            180                 185                 190

Gly Ala Val Gln Ala Val Ser Val Tyr Ser Asp Asp His Gly Lys Thr
        195                 200                 205

Trp Gln Ala Gly Thr Pro Ile Gly Thr Gly Met Asp Glu Asn Lys Val
    210                 215                 220

Val Glu Leu Ser Asp Gly Ser Leu Met Leu Asn Ser Arg Ala Ser Asp
225                 230                 235                 240

Gly Ser Gly Phe Arg Lys Val Ala His Ser Thr Asp Gly Gly Gln Thr
                245                 250                 255

Trp Ser Glu Pro Val Ser Asp Lys Asn Leu Pro Asp Ser Val Asp Asn
            260                 265                 270

Ala Gln Ile Ile Arg Ala Phe Pro Asn Ala Ala Pro Asp Asp Pro Arg
        275                 280                 285

Ala Lys Val Leu Leu Leu Ser His Ser Pro Asn Pro Arg Pro Trp Ser
    290                 295                 300

Arg Asp Arg Gly Thr Ile Ser Met Ser Cys Asp Asp Gly Ala Ser Trp
305                 310                 315                 320

Thr Thr Ser Lys Val Phe His Glu Pro Phe Val Gly Tyr Thr Thr Ile
                325                 330                 335

Ala Val Gln Ser Asp Gly Ser Ile Gly Leu Leu Ser Glu Asp Ala His
            340                 345                 350

Asn Gly Ala Asp Tyr Gly Gly Ile Trp Tyr Arg Asn Phe Thr Met Asn

```
                    355                 360                 365
Trp Leu Gly Glu Gln Cys Gly Gln Lys Pro Ala Lys Arg Lys Lys
                370                 375                 380

Gly Gly Lys Asn Gly Lys Asn Arg Arg Asn Arg Lys Lys Lys Asn Pro
385                 390                 395                 400
```

<210> SEQ ID NO 26
<211> LENGTH: 1248
<212> TYPE: DNA
<213> ORGANISM: Artificial Sequence
<220> FEATURE:
<223> OTHER INFORMATION: Synthetic Construct

<400> SEQUENCE: 26

```
atgggagagc tgccagcaag catgtctcag gctcagcatc ttgcagcaaa tacggctact    60
gataattatc gcattccagc gattacaacc gctccgaatg gtgatttact gattagctat   120
gatgaacggc cgaaggacaa tggaaatggt ggttccgatg cccctaaccc gaatcatatt   180
gttcagcgtc gctccacaga tggcggtaaa acttggagcg cgccaaccta tattcatcag   240
ggtacggaga ctggcaagaa agtgggatat tccgaccccct cttatgtggt ggatcatcaa   300
accggtacaa tcttcaattt tcatgtgaaa tcatacgatc agggctgggg aggtagccgt   360
gggggaacag acccggaaaa ccgcgggatt attcaggcag aggtgtctac gagcacggat   420
aatggatgga cgtggacaca tcgcaccatc accgcggata ttacgaaaga taaaccgtgg   480
accgcgcgtt ttgcggcgtc cggccaaggc attcagatcc agcatgggcc gcatgccggc   540
cgtctggtgc aacagtatac cattcgtacg gccggtggag cggtgcaggc tgtatcggtt   600
tattccgatg atcatgggaa aacgtggcag gctggcaccc cgattgggac gggtatggat   660
gaaaacaaag ttgtagagct gtctgacggc tctctgatgc tgaacagtcg tgcgtcggac   720
gggagcggct ttcgtaaggt tgcgcatagc actgatggtg ggcagacctg gtccgaaccg   780
gtttcggaca aaaatttgcc ggattcggtt gataatgccc agataattcg tgcgtttcct   840
aatgctgccc cgatgacccc gcgcgcgaaa gtacttcttc tgagtcattc cccaaatcca   900
cgtccgtggt cccgggatcg tggtacgata agcatgtcat gtgatgacgg ggcctcatgg   960
accacttcca agttttttca cgaaccgttt gtgggctaca cgactattgc agttcagagt  1020
gatgaaagca tcggtctgct gtcggaggac gcgcacaatg gcgctgatta tggtggcatc  1080
tggtatcgta attttacgat gaactggctg ggagaacaat gtggacaaaa acccgcggaa  1140
ccgagcccag cccctagccc tactgcagca ccgtccgctg caaagcgcaa aaaaaaggc  1200
ggcaaaaacg gtaaaaatcg tcgtaaccgt aagaaaaaaa atccttga              1248
```

<210> SEQ ID NO 27
<211> LENGTH: 415
<212> TYPE: PRT
<213> ORGANISM: Artificial Sequence
<220> FEATURE:
<223> OTHER INFORMATION: Synthetic Construct

<400> SEQUENCE: 27

```
Met Gly Glu Leu Pro Ala Ser Met Ser Gln Ala Gln His Leu Ala Ala
 1               5                  10                  15

Asn Thr Ala Thr Asp Asn Tyr Arg Ile Pro Ala Ile Thr Thr Ala Pro
                20                  25                  30

Asn Gly Asp Leu Leu Ile Ser Tyr Asp Glu Arg Pro Lys Asp Asn Gly
            35                  40                  45

Asn Gly Gly Ser Asp Ala Pro Asn Pro Asn His Ile Val Gln Arg Arg
```

```
                50                  55                  60
Ser Thr Asp Gly Gly Lys Thr Trp Ser Ala Pro Thr Tyr Ile His Gln
 65                  70                  75                  80

Gly Thr Glu Thr Gly Lys Lys Val Gly Tyr Ser Asp Pro Ser Tyr Val
                 85                  90                  95

Val Asp His Gln Thr Gly Thr Ile Phe Asn Phe His Val Lys Ser Tyr
                100                 105                 110

Asp Gln Gly Trp Gly Gly Ser Arg Gly Gly Thr Asp Pro Glu Asn Arg
                115                 120                 125

Gly Ile Ile Gln Ala Glu Val Ser Thr Ser Thr Asp Asn Gly Trp Thr
                130                 135                 140

Trp Thr His Arg Thr Ile Thr Ala Asp Ile Thr Lys Asp Lys Pro Trp
145                 150                 155                 160

Thr Ala Arg Phe Ala Ala Ser Gly Gln Gly Ile Gln Ile Gln His Gly
                165                 170                 175

Pro His Ala Gly Arg Leu Val Gln Gln Tyr Thr Ile Arg Thr Ala Gly
                180                 185                 190

Gly Ala Val Gln Ala Val Ser Val Tyr Ser Asp Asp His Gly Lys Thr
                195                 200                 205

Trp Gln Ala Gly Thr Pro Ile Gly Thr Gly Met Asp Glu Asn Lys Val
210                 215                 220

Val Glu Leu Ser Asp Gly Ser Leu Met Leu Asn Ser Arg Ala Ser Asp
225                 230                 235                 240

Gly Ser Gly Phe Arg Lys Val Ala His Ser Thr Asp Gly Gly Gln Thr
                245                 250                 255

Trp Ser Glu Pro Val Ser Asp Lys Asn Leu Pro Asp Ser Val Asp Asn
                260                 265                 270

Ala Gln Ile Ile Arg Ala Phe Pro Asn Ala Ala Pro Asp Asp Pro Arg
                275                 280                 285

Ala Lys Val Leu Leu Leu Ser His Ser Pro Asn Pro Arg Pro Trp Ser
290                 295                 300

Arg Asp Arg Gly Thr Ile Ser Met Ser Cys Asp Asp Gly Ala Ser Trp
305                 310                 315                 320

Thr Thr Ser Lys Val Phe His Glu Pro Phe Val Gly Tyr Thr Thr Ile
                325                 330                 335

Ala Val Gln Ser Asp Gly Ser Ile Gly Leu Leu Ser Glu Asp Ala His
                340                 345                 350

Asn Gly Ala Asp Tyr Gly Gly Ile Trp Tyr Arg Asn Phe Thr Met Asn
                355                 360                 365

Trp Leu Gly Glu Gln Cys Gly Gln Lys Pro Ala Glu Pro Ser Pro Ala
370                 375                 380

Pro Ser Pro Thr Ala Ala Pro Ser Ala Ala Lys Arg Lys Lys Lys Gly
385                 390                 395                 400

Gly Lys Asn Gly Lys Asn Arg Arg Asn Arg Lys Lys Asn Pro
                405                 410                 415
```

<210> SEQ ID NO 28
<211> LENGTH: 1221
<212> TYPE: DNA
<213> ORGANISM: Artificial Sequence
<220> FEATURE:
<223> OTHER INFORMATION: Synthetic Construct

<400> SEQUENCE: 28
ccatggggca tcaccatcac catcatctag agggagatca tccacaagct acaccagcac     60

-continued

```
ctgcaccaga tgctagcact gagctgccag caagcatgtc tcaggctcag catcttgcag      120
caaatacggc tactgataat tatcgcattc cagcgattac aaccgctccg aatggtgatt      180
tactgattag ctatgatgaa cggccgaagg acaatggaaa tggtggttcc gatgccccta      240
acccgaatca tattgttcag cgtcgctcca cagatggcgg taaaacttgg agcgcgccaa      300
cctatattca tcagggtacg gagactggca agaaagtggg atattccgac ccctcttatg      360
tggtggatca tcaaaccggt acaatcttca attttcatgt gaaatcatac gatcagggct      420
ggggaggtag ccgtggggga acagacccgg aaaaccgcgg gattattcag gcagaggtgt      480
ctacgagcac ggataatgga tggacgtgga cacatcgcac catcaccgcg gatattacga      540
aagataaacc gtggaccgcg cgttttgcgg cgtccggcca aggcattcag atccagcatg      600
ggccgcatgc cggccgtctg gtgcaacagt ataccattcg tacggccggt ggagcggtgc      660
aggctgtatc ggtttattcc gatgatcatg gaaaacgtg gcaggctggc accccgattg       720
ggacgggtat ggatgaaaac aaagttgtag agctgtctga cggctctctg atgctgaaca      780
gtcgtgcgtc ggacgggagc ggcttcgta aggttgcgca tagcactgat ggtgggcaga       840
cctggtccga accggtttcg gacaaaaatt gccggattc ggttgataat gcccagataa       900
ttcgtgcgtt tcctaatgct gcccccgatg acccgcgcgc gaaagtactt cttctgagtc      960
attccccaaa tccacgtccg tggtcccggg atcgtggtac gataagcatg tcatgtgatg     1020
acggggcctc atggaccact tccaaagttt ttcacgaacc gtttgtgggc tacacgacta     1080
ttgcagttca gagtgatgga agcatcggtc tgctgtcgga ggacgcgcac aatggcgctg     1140
attatggtgg catctggtat cgtaatttta cgatgaactg gctgggagaa caatgtggac     1200
aaaaacccgc ggaataagct t                                               1221
```

<210> SEQ ID NO 29
<211> LENGTH: 404
<212> TYPE: PRT
<213> ORGANISM: Artificial Sequence
<220> FEATURE:
<223> OTHER INFORMATION: Synthetic Construct

<400> SEQUENCE: 29

```
Met Gly His His His His His His Leu Glu Gly Asp His Pro Gln Ala
1               5                   10                  15

Thr Pro Ala Pro Ala Pro Asp Ala Ser Thr Glu Leu Pro Ala Ser Met
            20                  25                  30

Ser Gln Ala Gln His Leu Ala Ala Asn Thr Ala Thr Asp Asn Tyr Arg
        35                  40                  45

Ile Pro Ala Ile Thr Thr Ala Pro Asn Gly Asp Leu Leu Ile Ser Tyr
    50                  55                  60

Asp Glu Arg Pro Lys Asp Asn Gly Asn Gly Gly Ser Asp Ala Pro Asn
65                  70                  75                  80

Pro Asn His Ile Val Gln Arg Arg Ser Thr Asp Gly Gly Lys Thr Trp
                85                  90                  95

Ser Ala Pro Thr Tyr Ile His Gln Gly Thr Glu Thr Gly Lys Lys Val
            100                 105                 110

Gly Tyr Ser Asp Pro Ser Tyr Val Val Asp His Gln Thr Gly Thr Ile
        115                 120                 125

Phe Asn Phe His Val Lys Ser Tyr Asp Gln Gly Trp Gly Gly Ser Arg
    130                 135                 140

Gly Gly Thr Asp Pro Glu Asn Arg Gly Ile Ile Gln Ala Glu Val Ser
145                 150                 155                 160
```

```
Thr Ser Thr Asp Asn Gly Trp Thr Trp Thr His Arg Thr Ile Thr Ala
            165                 170                 175

Asp Ile Thr Lys Asp Lys Pro Trp Thr Ala Arg Phe Ala Ala Ser Gly
        180                 185                 190

Gln Gly Ile Gln Ile Gln His Gly Pro His Ala Gly Arg Leu Val Gln
        195                 200                 205

Gln Tyr Thr Ile Arg Thr Ala Gly Gly Ala Val Gln Ala Val Ser Val
        210                 215                 220

Tyr Ser Asp Asp His Gly Lys Thr Trp Gln Ala Gly Thr Pro Ile Gly
225                 230                 235                 240

Thr Gly Met Asp Glu Asn Lys Val Val Glu Leu Ser Asp Gly Ser Leu
                245                 250                 255

Met Leu Asn Ser Arg Ala Ser Asp Gly Ser Gly Phe Arg Lys Val Ala
            260                 265                 270

His Ser Thr Asp Gly Gly Gln Thr Trp Ser Glu Pro Val Ser Asp Lys
        275                 280                 285

Asn Leu Pro Asp Ser Val Asp Asn Ala Gln Ile Ile Arg Ala Phe Pro
    290                 295                 300

Asn Ala Ala Pro Asp Asp Pro Arg Ala Lys Val Leu Leu Leu Ser His
305                 310                 315                 320

Ser Pro Asn Pro Arg Pro Trp Ser Arg Asp Arg Gly Thr Ile Ser Met
                325                 330                 335

Ser Cys Asp Asp Gly Ala Ser Trp Thr Thr Ser Lys Val Phe His Glu
            340                 345                 350

Pro Phe Val Gly Tyr Thr Thr Ile Ala Val Gln Ser Asp Gly Ser Ile
        355                 360                 365

Gly Leu Leu Ser Glu Asp Ala His Asn Gly Ala Asp Tyr Gly Gly Ile
    370                 375                 380

Trp Tyr Arg Asn Phe Thr Met Asn Trp Leu Gly Glu Gln Cys Gly Gln
385                 390                 395                 400

Lys Pro Ala Glu

<210> SEQ ID NO 30
<211> LENGTH: 1257
<212> TYPE: DNA
<213> ORGANISM: Artificial Sequence
<220> FEATURE:
<223> OTHER INFORMATION: Synthetic Construct

<400> SEQUENCE: 30
ccatgaagcg caaaaaaaaa ggcggcaaaa acggtaaaaa tcgtcgtaac cgtaagaaaa      60
aaaatcctgg agatcatcca caagctacac cagcacctgc accagatgct agcactgagc     120
tgccagcaag catgtctcag gctcagcatc ttgcagcaaa tacggctact gataattatc     180
gcattccagc gattacaacc gctccgaatg gtgatttact gattagctat gatgaacggc     240
cgaaggacaa tggaaatggt ggttccgatg cccctaaccc gaatcatatt gttcagcgtc     300
gctccacaga tggcggtaaa acttggagcg cgccaaccta tattcatcag ggtacggaga     360
ctggcaagaa agtgggatat tccgacccct cttatgtggt ggatcatcaa accggtacaa     420
tcttcaattt tcatgtgaaa tcatacgatc agggctgggg aggtagccgt ggggggaacag     480 acccggaaaa ccgcgggatt attcaggcag aggtgtctac gagcacggat aatggatgga     540
cgtggacaca tcgcaccatc accgcggata ttacgaaaga taaaccgtgg accgcgcgtt     600
ttgcggcgtc cggccaaggc attcagatcc agcatgggcc gcatgccggc cgtctggtgc     660
aacagtatac cattcgtacg gccggtggag cggtgcaggc tgtatcggtt tattccgatg     720
```

```
atcatgggaa acgtggcag gctggcaccc cgattgggac gggtatggat gaaaacaaag    780
ttgtagagct gtctgacggc tctctgatgc tgaacagtcg tgcgtcggac gggagcggct    840
ttcgtaaggt tgcgcatagc actgatggtg ggcagacctg gtccgaaccg gtttcggaca    900
aaaatttgcc ggattcggtt gataatgccc agataattcg tgcgtttcct aatgctgccc    960
ccgatgaccc gcgcgcgaaa gtacttcttc tgagtcattc cccaaatcca cgtccgtggt   1020
cccgggatcg tggtacgata agcatgtcat gtgatgacgg ggcctcatgg accacttcca   1080 aagttttttca cgaaccgttt gtgggctaca cgactattgc agttcagagt gatgaaagca   1140
tcggtctgct gtcggaggac gcgcacaatg gcgctgatta tggtggcatc tggtatcgta   1200
attttacgat gaactggctg ggagaacaat gtggacaaaa accgcggaa  taagctt      1257
```

<210> SEQ ID NO 31
<211> LENGTH: 416
<212> TYPE: PRT
<213> ORGANISM: Artificial Sequence
<220> FEATURE:
<223> OTHER INFORMATION: Synthetic Construct

<400> SEQUENCE: 31

Met Lys Arg Lys Lys Gly Gly Lys Asn Gly Lys Asn Arg Arg Asn
 1               5                  10                  15

Arg Lys Lys Lys Asn Pro Gly Asp His Pro Gln Ala Thr Pro Ala Pro
                20                  25                  30

Ala Pro Asp Ala Ser Thr Glu Leu Pro Ala Ser Met Ser Gln Ala Gln
            35                  40                  45

His Leu Ala Ala Asn Thr Ala Thr Asp Asn Tyr Arg Ile Pro Ala Ile
        50                  55                  60

Thr Thr Ala Pro Asn Gly Asp Leu Leu Ile Ser Tyr Asp Glu Arg Pro
65                  70                  75                  80

Lys Asp Asn Gly Asn Gly Gly Ser Asp Ala Pro Asn Pro Asn His Ile
                85                  90                  95

Val Gln Arg Arg Ser Thr Asp Gly Gly Lys Thr Trp Ser Ala Pro Thr
            100                 105                 110

Tyr Ile His Gln Gly Thr Glu Thr Gly Lys Lys Val Gly Tyr Ser Asp
        115                 120                 125

Pro Ser Tyr Val Val Asp His Gln Thr Gly Thr Ile Phe Asn Phe His
    130                 135                 140

Val Lys Ser Tyr Asp Gln Gly Trp Gly Gly Ser Arg Gly Gly Thr Asp
145                 150                 155                 160

Pro Glu Asn Arg Gly Ile Ile Gln Ala Glu Val Ser Thr Ser Thr Asp
                165                 170                 175

Asn Gly Trp Thr Trp Thr His Arg Thr Ile Thr Ala Asp Ile Thr Lys
            180                 185                 190

Asp Lys Pro Trp Thr Ala Arg Phe Ala Ala Ser Gly Gln Gly Ile Gln
        195                 200                 205

Ile Gln His Gly Pro His Ala Gly Arg Leu Val Gln Gln Tyr Thr Ile
    210                 215                 220

Arg Thr Ala Gly Gly Ala Val Gln Ala Val Ser Val Tyr Ser Asp Asp
225                 230                 235                 240

His Gly Lys Thr Trp Gln Ala Gly Thr Pro Ile Gly Thr Gly Met Asp
                245                 250                 255

Glu Asn Lys Val Val Glu Leu Ser Asp Gly Ser Leu Met Leu Asn Ser
            260                 265                 270

```
Arg Ala Ser Asp Gly Ser Gly Phe Arg Lys Val Ala His Ser Thr Asp
            275                 280                 285

Gly Gly Gln Thr Trp Ser Glu Pro Val Ser Asp Lys Asn Leu Pro Asp
        290                 295                 300

Ser Val Asp Asn Ala Gln Ile Ile Arg Ala Phe Pro Asn Ala Ala Pro
305                 310                 315                 320

Asp Asp Pro Arg Ala Lys Val Leu Leu Leu Ser His Ser Pro Asn Pro
                325                 330                 335

Arg Pro Trp Ser Arg Asp Arg Gly Thr Ile Ser Met Ser Cys Asp Asp
            340                 345                 350

Gly Ala Ser Trp Thr Thr Ser Lys Val Phe His Glu Pro Phe Val Gly
        355                 360                 365

Tyr Thr Thr Ile Ala Val Gln Ser Asp Gly Ser Ile Gly Leu Leu Ser
370                 375                 380

Glu Asp Ala His Asn Gly Ala Asp Tyr Gly Gly Ile Trp Tyr Arg Asn
385                 390                 395                 400

Phe Thr Met Asn Trp Leu Gly Glu Gln Cys Gly Gln Lys Pro Ala Glu
                405                 410                 415

<210> SEQ ID NO 32
<211> LENGTH: 43
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 17, 18, 20, 21
<223> OTHER INFORMATION: n = A,T,C or G

<400> SEQUENCE: 32
ttttcgtctc ccatgvnnvn naagcgcaaa aaaaaggcg gca                 43

<210> SEQ ID NO 33
<211> LENGTH: 10
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 2, 3
<223> OTHER INFORMATION: Xaa = Any Amino Acid

<400> SEQUENCE: 33

Met Xaa Xaa Lys Arg Lys Lys Lys Gly Gly
  1               5                  10

<210> SEQ ID NO 34
<211> LENGTH: 1272
<212> TYPE: DNA
<213> ORGANISM: Artificial Sequence
<220> FEATURE:
<223> OTHER INFORMATION: Synthetic Construct

<400> SEQUENCE: 34
ccatgaagcg caaaaaaaaa ggcggcaaaa acggtaaaaa tcgtcgtaac cgtaagaaaa     60
aaaatcctgg tggtggtggt tctggagatc atccacaagc tacaccagca cctgcaccag    120
atgctagcac tgagctgcca gcaagcatgt ctcaggctca gcatcttgca gcaaatacgg    180
ctactgataa ttatcgcatt ccagcgatta caaccgctcc gaatggtgat ttactgatta    240
gctatgatga acggccgaag gacaatggaa atggtggttc cgatgcccct aacccgaatc    300
```

```
atattgttca gcgtcgctcc acagatggcg gtaaaacttg gagcgcgcca acctatattc    360
atcagggtac ggagactggc aagaaagtgg gatattccga cccctcttat gtggtggatc    420
atcaaaccgg tacaatcttc aattttcatg tgaaatcata cgatcagggc tggggaggta    480
gccgtggggg aacagacccg gaaaaccgcg ggattattca ggcagaggtg tctacgagca    540
cggataatgg atggacgtgg acacatcgca ccatcaccgc ggatattacg aaagataaac    600
cgtggaccgc gcgttttgcg gcgtccggcc aaggcattca gatccagcat gggccgcatg    660
ccggccgtct ggtgcaacag tataccattc gtacggccgg tggagcggtg caggctgtat    720
cggtttattc cgatgatcat gggaaaacgt ggcaggctgg cacccgatt gggacgggta     780
tggatgaaaa caaagttgta gagctgtctg acggctctct gatgctgaac agtcgtgcgt    840
cggacgggag cggctttcgt aaggttgcgc atagcactga tggtgggcag acctggtccg    900
aaccggtttc ggacaaaaat ttgccggatt cggttgataa tgcccagata attcgtgcgt    960
ttcctaatgc tgcccccgat gacccgcgcg cgaaagtact tcttctgagt cattccccaa    1020
atccacgtcc gtggtcccgg gatcgtggta cgataagcat gtcatgtgat gacggggcct    1080
catggaccac ttccaaagtt tttcacgaac cgtttgtggg ctacacgact attgcagttc    1140
agagtgatgg aagcatcggt ctgctgtcgg aggacgcgca caatggcgct gattatggtg    1200
gcatctggta tcgtaatttt acgatgaact ggctgggaga acaatgtgga caaaaacccg    1260
cggaataagc tt                                                         1272
```

<210> SEQ ID NO 35
<211> LENGTH: 421
<212> TYPE: PRT
<213> ORGANISM: Artificial Sequence
<220> FEATURE:
<223> OTHER INFORMATION: Synthetic Construct

<400> SEQUENCE: 35

Met Lys Arg Lys Lys Gly Gly Lys Asn Gly Lys Asn Arg Arg Asn
1               5                   10                  15

Arg Lys Lys Lys Asn Pro Gly Gly Gly Ser Gly Asp His Pro Gln
                20                  25                  30

Ala Thr Pro Ala Pro Ala Pro Asp Ala Ser Thr Glu Leu Pro Ala Ser
            35                  40                  45

Met Ser Gln Ala Gln His Leu Ala Ala Asn Thr Ala Thr Asp Asn Tyr
        50                  55                  60

Arg Ile Pro Ala Ile Thr Thr Ala Pro Asn Gly Asp Leu Leu Ile Ser
65                  70                  75                  80

Tyr Asp Glu Arg Pro Lys Asp Asn Gly Asn Gly Gly Ser Asp Ala Pro
                85                  90                  95

Asn Pro Asn His Ile Val Gln Arg Arg Ser Thr Asp Gly Gly Lys Thr
            100                 105                 110

Trp Ser Ala Pro Thr Tyr Ile His Gln Gly Thr Glu Thr Gly Lys Lys
        115                 120                 125

Val Gly Tyr Ser Asp Pro Ser Tyr Val Val Asp His Gln Thr Gly Thr
    130                 135                 140

Ile Phe Asn Phe His Val Lys Ser Tyr Asp Gln Gly Trp Gly Gly Ser
145                 150                 155                 160

Arg Gly Gly Thr Asp Pro Glu Asn Arg Gly Ile Ile Gln Ala Glu Val
                165                 170                 175

Ser Thr Ser Thr Asp Asn Gly Trp Thr Trp Thr His Arg Thr Ile Thr
            180                 185                 190

```
Ala Asp Ile Thr Lys Asp Lys Pro Trp Thr Ala Arg Phe Ala Ala Ser
    195                 200                 205

Gly Gln Gly Ile Gln Ile Gln His Gly Pro His Ala Gly Arg Leu Val
210                 215                 220

Gln Gln Tyr Thr Ile Arg Thr Ala Gly Gly Ala Val Gln Ala Val Ser
225                 230                 235                 240

Val Tyr Ser Asp Asp His Gly Lys Thr Trp Gln Ala Gly Thr Pro Ile
                245                 250                 255

Gly Thr Gly Met Asp Glu Asn Lys Val Val Glu Leu Ser Asp Gly Ser
                260                 265                 270

Leu Met Leu Asn Ser Arg Ala Ser Asp Gly Ser Gly Phe Arg Lys Val
    275                 280                 285

Ala His Ser Thr Asp Gly Gly Gln Thr Trp Ser Glu Pro Val Ser Asp
    290                 295                 300

Lys Asn Leu Pro Asp Ser Val Asp Asn Ala Gln Ile Ile Arg Ala Phe
305                 310                 315                 320

Pro Asn Ala Ala Pro Asp Asp Pro Arg Ala Lys Val Leu Leu Leu Ser
                325                 330                 335

His Ser Pro Asn Pro Arg Pro Trp Ser Arg Asp Arg Gly Thr Ile Ser
                340                 345                 350

Met Ser Cys Asp Asp Gly Ala Ser Trp Thr Thr Ser Lys Val Phe His
    355                 360                 365

Glu Pro Phe Val Gly Tyr Thr Thr Ile Ala Val Gln Ser Asp Gly Ser
    370                 375                 380

Ile Gly Leu Leu Ser Glu Asp Ala His Asn Gly Ala Asp Tyr Gly Gly
385                 390                 395                 400

Ile Trp Tyr Arg Asn Phe Thr Met Asn Trp Leu Gly Glu Gln Cys Gly
                405                 410                 415

Gln Lys Pro Ala Glu
                420

<210> SEQ ID NO 36
<211> LENGTH: 1275
<212> TYPE: DNA
<213> ORGANISM: Artificial Sequence
<220> FEATURE:
<223> OTHER INFORMATION: Synthetic Construct

<400> SEQUENCE: 36
ccatggttaa gcgcaaaaaa aaaggcggca aaaacggtaa aaatcgtcgt aaccgtaaga      60
aaaaaaatcc tggtggtggt ggttctggag atcatccaca agctacacca gcacctgcac     120
cagatgctag cactgagctg ccagcaagca tgtctcaggc tcagcatctt gcagcaaata     180
cggctactga taattatcgc attccagcga ttacaaccgc tccgaatggt gatttactga     240
ttagctatga tgaacggccg aaggacaatg gaaatggtgg ttccgatgcc ctaacccga     300 atcatattgt tcagcgtcgc tccacagatg gcggtaaaac ttggagcgcg ccaacctata     360
ttcatcaggg tacggagact ggcaagaaag tgggatattc cgaccctct tatgtggtgg     420 atcatcaaac cggtacaatc ttcaattttc atgtgaaatc atacgatcag ggctggggag     480
gtagccgtgg gggaacagac ccggaaaacc gcggattat tcaggcagag gtgtctacga     540
gcacggataa tggatggacg tggacacatc gcaccatcac cgcggatatt acgaaagata     600
aaccgtggac cgcgcgtttt gcggcgtccg gccaaggcat tcagatccag catgggccgc     660
atgccggccg tctggtgcaa cagtatacca ttcgtacggc cggtgagcg gtgcaggctg     720 tatcggttta ttccgatgat catgggaaaa cgtggcaggc tggcaccccg attgggacgg     780
```

```
gtatggatga aaacaaagtt gtagagctgt ctgacggctc tctgatgctg aacagtcgtg      840
cgtcggacgg gagcggcttt cgtaaggttg cgcatagcac tgatggtggg cagacctggt      900
ccgaaccggt ttcggacaaa aatttgccgg attcggttga taatgcccag ataattcgtg      960
cgtttcctaa tgctgccccc gatgacccgc gcgcgaaagt acttcttctg agtcattccc     1020
caaatccacg tccgtggtcc cgggatcgtg gtacgataag catgtcatgt gatgacgggg     1080
cctcatggac cacttccaaa gttttcacg aaccgtttgt gggctacacg actattgcag      1140
ttcagagtga tggaagcatc ggtctgctgt cggaggacgc gcacaatggc gctgattatg     1200
gtggcatctg gtatcgtaat tttacgatga actggctggg agaacaatgt ggacaaaaac     1260
ccgcggaata agctt                                                      1275
```

<210> SEQ ID NO 37
<211> LENGTH: 422
<212> TYPE: PRT
<213> ORGANISM: Artificial Sequence
<220> FEATURE:
<223> OTHER INFORMATION: Synthetic Construct

<400> SEQUENCE: 37

```
Met Val Lys Arg Lys Lys Gly Gly Lys Asn Gly Lys Asn Arg Arg
 1               5                  10                  15

Asn Arg Lys Lys Lys Asn Pro Gly Gly Gly Ser Gly Asp His Pro
                20                  25                  30

Gln Ala Thr Pro Ala Pro Ala Pro Asp Ala Ser Thr Glu Leu Pro Ala
                35                  40                  45

Ser Met Ser Gln Ala Gln His Leu Ala Ala Asn Thr Ala Thr Asp Asn
50                  55                  60

Tyr Arg Ile Pro Ala Ile Thr Thr Ala Pro Asn Gly Asp Leu Leu Ile
65                  70                  75                  80

Ser Tyr Asp Glu Arg Pro Lys Asp Asn Gly Asn Gly Gly Ser Asp Ala
                85                  90                  95

Pro Asn Pro Asn His Ile Val Gln Arg Arg Ser Thr Asp Gly Gly Lys
                100                 105                 110

Thr Trp Ser Ala Pro Thr Tyr Ile His Gln Gly Thr Glu Thr Gly Lys
                115                 120                 125

Lys Val Gly Tyr Ser Asp Pro Ser Tyr Val Val Asp His Gln Thr Gly
                130                 135                 140

Thr Ile Phe Asn Phe His Val Lys Ser Tyr Asp Gln Gly Trp Gly Gly
145                 150                 155                 160

Ser Arg Gly Gly Thr Asp Pro Glu Asn Arg Gly Ile Ile Gln Ala Glu
                165                 170                 175

Val Ser Thr Ser Thr Asp Asn Gly Trp Thr Trp Thr His Arg Thr Ile
                180                 185                 190

Thr Ala Asp Ile Thr Lys Asp Lys Pro Trp Thr Ala Arg Phe Ala Ala
                195                 200                 205

Ser Gly Gln Gly Ile Gln Ile Gln His Gly Pro His Ala Gly Arg Leu
                210                 215                 220

Val Gln Gln Tyr Thr Ile Arg Thr Ala Gly Gly Ala Val Gln Ala Val
225                 230                 235                 240

Ser Val Tyr Ser Asp Asp His Gly Lys Thr Trp Gln Ala Gly Thr Pro
                245                 250                 255

Ile Gly Thr Gly Met Asp Glu Asn Lys Val Val Glu Leu Ser Asp Gly
                260                 265                 270
```

```
Ser Leu Met Leu Asn Ser Arg Ala Ser Asp Gly Ser Gly Phe Arg Lys
        275                 280                 285

Val Ala His Ser Thr Asp Gly Gln Thr Trp Ser Glu Pro Val Ser
    290                 295                 300

Asp Lys Asn Leu Pro Asp Ser Val Asp Asn Ala Gln Ile Ile Arg Ala
305                 310                 315                 320

Phe Pro Asn Ala Ala Pro Asp Pro Arg Ala Lys Val Leu Leu Leu
                325                 330                 335

Ser His Ser Pro Asn Pro Arg Pro Trp Ser Arg Asp Arg Gly Thr Ile
                340                 345                 350

Ser Met Ser Cys Asp Asp Gly Ala Ser Trp Thr Thr Ser Lys Val Phe
            355                 360                 365

His Glu Pro Phe Val Gly Tyr Thr Thr Ile Ala Val Gln Ser Asp Gly
        370                 375                 380

Ser Ile Gly Leu Leu Ser Glu Asp Ala His Asn Gly Ala Asp Tyr Gly
385                 390                 395                 400

Gly Ile Trp Tyr Arg Asn Phe Thr Met Asn Trp Leu Gly Glu Gln Cys
                405                 410                 415

Gly Gln Lys Pro Ala Glu
            420

<210> SEQ ID NO 38
<211> LENGTH: 416
<212> TYPE: PRT
<213> ORGANISM: Artificial Sequence
<220> FEATURE:
<223> OTHER INFORMATION: Synthetic Construct

<400> SEQUENCE: 38

Met Lys Arg Lys Lys Gly Gly Lys Asn Gly Lys Asn Arg Arg Asn
1               5                   10                  15

Arg Lys Lys Lys Asn Pro Gly Asp His Pro Gln Ala Thr Pro Ala Pro
                20                  25                  30

Ala Pro Asp Ala Ser Thr Glu Leu Pro Ala Ser Met Ser Gln Ala Gln
            35                  40                  45

His Leu Ala Ala Asn Thr Ala Thr Asp Asn Tyr Arg Ile Pro Ala Ile
    50                  55                  60

Thr Thr Ala Pro Asn Gly Asp Leu Leu Ile Ser Tyr Asp Glu Arg Pro
65                  70                  75                  80

Lys Asp Asn Gly Asn Gly Gly Ser Asp Ala Pro Asn Pro Asn His Ile
                85                  90                  95

Val Gln Arg Arg Ser Thr Asp Gly Gly Lys Thr Trp Ser Ala Pro Thr
                100                 105                 110

Tyr Ile His Gln Gly Thr Glu Thr Gly Lys Lys Val Gly Tyr Ser Asp
            115                 120                 125

Pro Ser Tyr Val Val Asp His Gln Thr Gly Thr Ile Phe Asn Phe His
    130                 135                 140

Val Lys Ser Tyr Asp Gln Gly Trp Gly Gly Ser Arg Gly Gly Thr Asp
145                 150                 155                 160

Pro Glu Asn Arg Gly Ile Ile Gln Ala Glu Val Ser Thr Ser Thr Asp
                165                 170                 175

Asn Gly Trp Thr Trp Thr His Arg Thr Ile Thr Ala Asp Ile Thr Lys
            180                 185                 190

Asp Lys Pro Trp Thr Ala Arg Phe Ala Ala Ser Gly Gln Gly Ile Gln
    195                 200                 205

Ile Gln His Gly Pro His Ala Gly Arg Leu Val Gln Gln Tyr Thr Ile
```

```
                    210                 215                 220
Arg Thr Ala Gly Gly Ala Val Gln Ala Val Ser Val Tyr Ser Asp Asp
225                 230                 235                 240

His Gly Lys Thr Trp Gln Ala Gly Thr Pro Ile Gly Thr Gly Met Asp
                245                 250                 255

Glu Asn Lys Val Val Glu Leu Ser Asp Gly Ser Leu Met Leu Asn Ser
                260                 265                 270

Arg Ala Ser Asp Gly Ser Phe Arg Lys Val Ala His Ser Thr Asp
                275                 280                 285

Gly Gly Gln Thr Trp Ser Glu Pro Val Ser Asp Lys Asn Leu Pro Asp
        290                 295                 300

Ser Val Asp Asn Ala Gln Ile Ile Arg Ala Phe Pro Asn Ala Ala Pro
305                 310                 315                 320

Asp Asp Pro Arg Ala Lys Val Leu Leu Leu Ser His Ser Pro Asn Pro
                325                 330                 335

Arg Pro Trp Ser Arg Asp Arg Gly Thr Ile Ser Met Ser Cys Asp Asp
                340                 345                 350

Gly Ala Ser Trp Thr Thr Ser Lys Val Phe His Glu Pro Phe Val Gly
                355                 360                 365

Tyr Thr Thr Ile Ala Val Gln Ser Asp Gly Ser Ile Gly Leu Leu Ser
        370                 375                 380

Glu Asp Ala His Asn Gly Ala Asp Tyr Gly Gly Ile Trp Tyr Arg Asn
385                 390                 395                 400

Phe Thr Met Asn Trp Leu Gly Glu Gln Cys Gly Gln Lys Pro Ala Glu
                405                 410                 415

<210> SEQ ID NO 39
<211> LENGTH: 421
<212> TYPE: PRT
<213> ORGANISM: Artificial Sequence
<220> FEATURE:
<223> OTHER INFORMATION: Synthetic Construct

<400> SEQUENCE: 39

Val Lys Arg Lys Lys Gly Gly Lys Asn Gly Lys Asn Arg Arg Asn
 1               5                  10                  15

Arg Lys Lys Lys Asn Pro Gly Gly Gly Ser Gly Asp His Pro Gln
                20                  25                  30

Ala Thr Pro Ala Pro Ala Pro Asp Ala Ser Thr Glu Leu Pro Ala Ser
                35                  40                  45

Met Ser Gln Ala Gln His Leu Ala Ala Asn Thr Ala Thr Asp Asn Tyr
50                  55                  60

Arg Ile Pro Ala Ile Thr Thr Ala Pro Asn Gly Asp Leu Leu Ile Ser
65                  70                  75                  80

Tyr Asp Glu Arg Pro Lys Asp Asn Gly Asn Gly Gly Ser Asp Ala Pro
                85                  90                  95

Asn Pro Asn His Ile Val Gln Arg Arg Ser Thr Asp Gly Gly Lys Thr
                100                 105                 110

Trp Ser Ala Pro Thr Tyr Ile His Gln Gly Thr Glu Thr Gly Lys Lys
                115                 120                 125

Val Gly Tyr Ser Asp Pro Ser Tyr Val Val Asp His Gln Thr Gly Thr
        130                 135                 140

Ile Phe Asn Phe His Val Lys Ser Tyr Asp Gln Gly Trp Gly Ser
145                 150                 155                 160

Arg Gly Gly Thr Asp Pro Glu Asn Arg Gly Ile Ile Gln Ala Glu Val
                165                 170                 175
```

```
Ser Thr Ser Thr Asp Asn Gly Trp Thr Trp Thr His Arg Thr Ile Thr
            180                 185                 190

Ala Asp Ile Thr Lys Asp Lys Pro Trp Thr Ala Arg Phe Ala Ala Ser
            195                 200                 205

Gly Gln Gly Ile Gln Ile Gln His Gly Pro His Ala Gly Arg Leu Val
            210                 215                 220

Gln Gln Tyr Thr Ile Arg Thr Ala Gly Gly Ala Val Gln Ala Val Ser
225                     230                 235                 240

Val Tyr Ser Asp Asp His Gly Lys Thr Trp Gln Ala Gly Thr Pro Ile
                245                 250                 255

Gly Thr Gly Met Asp Glu Asn Lys Val Val Glu Leu Ser Asp Gly Ser
            260                 265                 270

Leu Met Leu Asn Ser Arg Ala Ser Asp Gly Ser Gly Phe Arg Lys Val
            275                 280                 285

Ala His Ser Thr Asp Gly Gly Gln Thr Trp Ser Glu Pro Val Ser Asp
            290                 295                 300

Lys Asn Leu Pro Asp Ser Val Asp Asn Ala Gln Ile Ile Arg Ala Phe
305                     310                 315                 320

Pro Asn Ala Ala Pro Asp Pro Arg Ala Lys Val Leu Leu Leu Ser
                325                 330                 335

His Ser Pro Asn Pro Arg Pro Trp Ser Arg Asp Arg Gly Thr Ile Ser
                340                 345                 350

Met Ser Cys Asp Asp Gly Ala Ser Trp Thr Thr Ser Lys Val Phe His
            355                 360                 365

Glu Pro Phe Val Gly Tyr Thr Thr Ile Ala Val Gln Ser Asp Gly Ser
    370                 375                 380

Ile Gly Leu Leu Ser Glu Asp Ala His Asn Gly Ala Asp Tyr Gly Gly
385                     390                 395                 400

Ile Trp Tyr Arg Asn Phe Thr Met Asn Trp Leu Gly Glu Gln Cys Gly
                405                 410                 415

Gln Lys Pro Ala Glu
                420
```